United States Patent [19]
Yamamoto et al.

[11] Patent Number: 6,034,060
[45] Date of Patent: Mar. 7, 2000

[54] PEPTIDE HAVING AN ABILITY TO PROMOTE THE ACTIVATION OF PROTEIN C BY THROMBIN

[75] Inventors: Shuji Yamamoto, Fuji; Koji Suzuki, Tsu, both of Japan

[73] Assignee: Asahi Kasei Kogyo Kabushiki Kaisha, Japan

[21] Appl. No.: 08/181,458

[22] Filed: Jan. 14, 1994

Related U.S. Application Data

[62] Division of application No. 07/908,887, Jul. 7, 1992, abandoned, which is a continuation of application No. 07/243,297, Aug. 17, 1988, abandoned.

[30] Foreign Application Priority Data

| | | | |
|---|---|---|---|
| Jan. 8, 1987 | [JP] | Japan | 62-1065 |
| Jan. 8, 1987 | [JP] | Japan | 62-1066 |
| Jun. 11, 1987 | [JP] | Japan | 62-144081 |
| Dec. 4, 1987 | [JP] | Japan | 62-305876 |
| Dec. 4, 1987 | [JP] | Japan | 62-305877 |
| Dec. 4, 1987 | [JP] | Japan | 62-305878 |
| Jan. 8, 1988 | [WO] | WIPO | PCT/JP88/00011 |

[51] Int. Cl.$^7$ ............ A61K 38/17; A61K 38/36; C12N 15/12
[52] U.S. Cl. .......... 514/12; 435/69.6; 435/320.1; 435/325; 435/252.3; 530/350; 530/380; 530/381
[58] Field of Search ............... 530/350, 380, 530/381; 514/12; 536/23.5, 23.1; 435/69.6, 320.1, 240.2, 252.3, 325

[56] References Cited

U.S. PATENT DOCUMENTS

| | | | |
|---|---|---|---|
| 4,638,050 | 1/1987 | Aoki | 530/413 |
| 4,748,156 | 5/1988 | Aoki et al. . | |
| 4,912,207 | 3/1990 | Majerus | 536/27 |
| 5,466,668 | 11/1995 | Glaser et al. . | |
| 5,516,659 | 5/1996 | Nii et al. . | |
| 5,583,102 | 12/1996 | Lentz et al. . | |

FOREIGN PATENT DOCUMENTS 0155852  9/1985  European Pat. Off. .

OTHER PUBLICATIONS

Cuatrecasas, P., *J. Biol. Chem.,* 245(12) : 3059–3065, 1970.
Salem et al. "Kolabirn & Characterization of Thrombomodulin from Human Placenta" J. Biol. Chemistry v. 259(19) 12246–12251 (Oct. 10, 1984).
Wen, D "Human Thrombomodulin:Complete cDNA Sequence & Chromosome Localization of the Gene" Biochemistry 26:4350–4357 (Jul. 14, 1987) 1986/1987 IBI Catalog "Life on the Edge" vol. II published by International Biotechnologies, Inc. pp. 78–79.
Suzuki et al, The EMBO Journal, 6, No. 7, pp. 1891–1897 (1987).
Wen et al, Biochemistry, 26, pp. 4350–4357 (1987).
Jackman et al, Proc. Natl. Acad. Sci. USA, 83, pp. 8834–8838 (1986).
Hidemi Ishii et al, "Thrombomodulin Is Present in Human Plasma and Urine", J. Clin. Invest. vol. 76, (1985) pp. 2178–2181.
Shinichiro Kurosawa et al., "Proteolytic Formation and Properties of Functional Domains of Thrombomodulin", The Journal of Biological Chemistry, vol. 262, No. 5, (1987) pp. 2206–2212.
Koji Suzuki et al., "Isolation and charaterization of thrombomodulin from bovine lung", Biochimica et Biophysica Acta 882 (1986) pp. 343–352.
Robert W. Jackman et al., "Human thrombomodulin gene is intron depleted: Nucleic acid sequences of the cDNA and gene predict protein structure and suggest sites of regulatory control", Proc. Natl. Acad. Sci. USA, vol. 84 (1987) pp. 6424–6429.
Hiroshi Kusumoto, "Thrombomodulin, A Cofactor of Protein C Activation: Isolation, Characterization and Application for Laboratory Medicine", Mie Medical Journal, vol. 37 No. 1 (1987) pp. 145–172.
D. Wen et al., "Human Thrombomodulin:CDNA Cloning and Primary Structure", Clinical Research, vol. 35, No. 3 (1987) p. 603A.
N.L. Esmon et al., J. Biol. Chem., vol. 257, p. 859 (1982).
C.T. Esmon et al., Proc. Natl. Acad. Sci. USA, vol. 78, p. 2249 (1981).
C.T. Esmon et al., J. Biol. Chem., vol. 257, p. 7944 (1982).
N.L. Esmon et al., J. Biol. Chem., vol. 258, p. 12238 (1983).
H.H. Salem et al., J. Biol. Chem., vol. 259, p. 12246 (1984).
S.Kurosawa et al., Thromb. Res., vol. 37, p. 353 (1985).
Kusumoto et al., Biochemistry, Japan, vol. 56, p. 890 (1984).
Kusumoto et al., Biochemistry, Japan, vol. 57, p. 1102 (1985).

*Primary Examiner*—Marianne P. Allen
*Attorney, Agent, or Firm*—Birch, Stewart, Kolasch & Birch, LLP

[57] ABSTRACT

The peptide of the present invention comprises a specific amino acid sequence including at least 118 amino acids and has the ability to promote the activation of protein C by thrombin. The peptide of the present invention can be produced efficiently on a large scale by recombinant DNA techniques. The peptide of the present invention has anticoagulant, platelet aggregation-inhibiting and thrombolytic activities, without exhibiting side effects such as bleeding and anaphylactic shock. Therefore, the peptide of the present invention can be effectively used for the treatment of various circulatory organ diseases, toxemia of pregnancy and the like.

17 Claims, 39 Drawing Sheets

FIG. 2 (a)

```
GAGTACCAGT  GCCAGCCCCT  GAACCAAACT
AGCTACCTCT  GCGTCTGCGC  CGAGGGCTTC
    HTM131
GCGCCATTC   CCCACGAGCC  GCACAGGTGC
CAGATGTTTT  GCAACCAGAC  TGCCTGTCCA
    HTM132              HTM133
GCCGACTGCG  ACCCCAACAC  CCAGGCTAGC
TGTGAGTGCC  CTGAAGGCTA  CATCCTGGAC
GACGGTTTCA  TCTGCACGGA  CATCGACGAG
TGCGAAAACG  GCGGCTTCTG  CTCCGGGGTG
TGCCACAACC  TCCCCGGTAC  CTTCGAGTGC
ATCTGCGGC   CCGACTGGC   CCTTGTCCGC
CACATTGGCA  CCGACTGTGA  CTCCGGCAAG
GTGGACGGTG  GCGACAGCGG  CTCTGGCGAG
CCCCGCCCA   GCCCGACGCC  CGGCTCCACC
TTGACTCCTC  CGGCCGTGGG  GCTCGTGCAT
TCGGGCTTGC  TCATAGGCAT  CTCCATCGCG
AGCCTGTGCC  TGGTGGTGGC  GCTTTTGGCG
CTCCTCTGCC  ACCTGCGCAA  GAAGCAGGGC
GCCGCAGGG   CCAAGATGGA  GTACAAGTGC
GCGGCCCTT   CCAAGGAGGT  AGTGCTGCAG
```

FIG. 2 (b)

```
CACGTGCGGA  CCGAGCGGAC  GCCGCAGAGA
CTCTGAGCGG  CCTCCGTCCA  GGAGCCTGGC
TCCGTCCAGG  AGCCTGTGCC  TCCTCACCCC
CAGCTTTGCT  ACCAAAGCAC  CTTAGCTGGC
ATTACAGCTG  GAGAAGACCC  TCCCCGCACC
CCCAAGCTG   TTTTCTTCTA  TTCCATGGCT
AACTGGCGAG  GGGGTGATTA  GAGGGAGGAG
AATGAGCCTC  GGCCTCTTCC  GTGACGTCAC
TGGACCACTG  GGCAATGATG  GCAATTTGT
AACGAAGACA  CAGACTGCGA  TTTGTCCAG
GTCCTCACTA  CCGGGCGCAG  GAGGGTGAGC
GTTATTGGTC  GGCAGCCTTC  TGGGCAGACC
TTGACCTCGT  GGGCTAGGA   TGACTAAAAT
ATTTATTTT   TTTAAGTATT  TAGGTTTTG
TTTGTTTCCT  TTGTTCTTAC  CTGTATGTCT
CCAGTATCCA  CTTTGCACAG  CTCTCCGGTC
TCTCTCTCTC  TACAAACTCC  CACTTGTCAT
GTGACAGGTA  AACTATCTTG  GTGAA
```

FIG. 3 (a)

```
GGGCTCCTAC  TCGTGCATGT  GCGAGACCGG
CTACCGGCTG  GCGGCGACC   AACACCGGTG
CGAGGACGTG  GATGACTGCA  TACTGGAGCC
CAGTCCGTGT  CCGCAGCGCT  GTGTCAACAC
ACAGGGTGGC  TTCGAGTGCC  ACTGCTACCC
TAACTACGAC  CTGGTGGACG  GCGAGTGTGT
GGAGCCCGTG  GACCCGTGCT  TCAGAGCCAA
CTGCGAGTAC  CAGTGCCAGC  CCCTGAACCA
                                  ─
AACTAGCTAC  CTCTGCGTCT  GCGCCGAGGG
─────────                ─
  HTM131
CTTCGCGCCC  ATTCCCACG   AGCCGCACAG
                                ───
GTGCCAGATG  TTTTGCAACC  AGACTGCCTG
─────────              ──────────
  HTM132                   HTM133
TCCAGCCGAC  TGCGACCCCA  ACACCCAGGC
──
TAGCTGTGAG  TGCCCTGAAG  GCTACATCCT
GGACGACGGT  TTCATCTGCA  CGGACATCGA
CGAGTGCGAA  AACGGCGGCT  TCTGCTCCGG
GGTGTGCCAC  AACCTCCCCG  GTACCTTCGA
GTGCATCTGC  GGGCCGACT   CGGCCCTTGT
CCGCCACATT  GGCACCGACT  GTGACTCCGG
CAAGGTGGAC  GGTGGCGACA  GCGGCTCTGG
CGAGCCCCCG  CCCAGCCCGA  CGCCCGGCTC
```

FIG. 3 (b)

```
CACCTTGACT  CCTCCGGCCG  TGGGGCTCGT
GCATTCGGGC  TTGCTCATAG  GCATCTCCAT
CGCGAGCCTG  TGCCTGGTGG  TGGCGTTTT
GGCGCTCCTC  TGCCACCTGC  GCAAGAAGCA
GGGCGCCGCC  AGGGCCAAGA  TGGAGTACAA
GTGCGCGGCC  CCTTCCAAGG  AGGTAGTGCT
GCAGCACGTG  CGGACCGAGC  GGACGCCGCA
GAGACTCTGA  GCGGCCTCCG  TCCAGGAGCC
TGGCTCCGTC  CAGGAGCCTG  TGCCTCCTCA
CCCCAGCTT   TGCTACCAAA  GCACCTTAGC
TGGCATTACA  GCTGGAGAAG  ACCCTCCCCG
CACCCCCAA   GCTGTTTCT   TCTATTCCAT
GGCTAACTGG  CGAGGGGTG   ATTAGAGGA
GGAGAATGAG  CCTCGGCCTC  TTCCGTGACG
TCACTGGACC  ACTGGCAAT   GATGGCAATT
TTGTAACGAA  GACACAGACT  GCGATTTGTC
CCAGGTCCTC  ACTACCGGGC  GCAGGAGGGT
GAGCGTTATT  GGTCGGCAGC  CTTCTGGGCA
GACCTTGACC  TCGTGGGCTA  GGGATGACTA
```

FIG. 3 (c)

```
AAATATTTAT  TTTTTTAAG   TATTTAGGTT
TTTGTTTGTT  TCCTTTGTTC  TTACCTGTAT
GTCTCCAGTA  TCCACTTTGC  ACAGCTCTCC
GGTCTCTCTC  TCTCTACAAA  CTCCCACTTG
TCATGTGACA  GGTAAACTAT  CTTGGTGAAT
TTTTTTTCC   TAGCCCTCTC  ACATTATGA
AGCAAGCCCC  ACTTATTCCC  CATTCTTCCT
AGTTTTCTCC  TCCCAGGAAC  TGGGCCAACT
CACCTGAGTC  ACCCTACCTG  TGCCTGACCC
TACTTCTTTT  GCTCTTAGCT  GTCTGCTCAG
ACAGAACCCC  TACATGAAAC  AGAAACAAAA
ACACTAAAAA  TAAAAATGGC  CATTTGCTTT
TTCACCAGAT  TTGCTAATTT  ATCCTGAAAT
TTCAGATTCC  CAGAGCAAAA  TAATTTTAAA
CAAAGGTTGA  GATGTAAAAG  GTATTAAATT
GATGTTGCTG  GACTGTCATA  GAAATTACAC
CCAAAGAGGT  ATTTATCTTT  ACTTTTAAAC
AGTGAGCCTG  AATTTTGTTG  CTGTTTTGAT
TTGTACTGAA  AAATGGTAAT  TGTTGCTAAT
CTTCTTATGC  AATTTCCTTT  TTTGTTATTA
```

FIG. 3 (d)

```
TTACTTATTT TTGACAGTGT TGAAAATGTT
CAGAAGGTTG CTCTAGATTG AGAGAAGAGA
CAAACACCTC CCAGGAGACA GTTCAAGAAA
GCTTCAAACT GCATGATTCA TGCCAATTAG
CAATTGACTG TCACTGTTCC TTGTCACTGG
TAGACCAAAA TAAACCACT  TAACTGGTCT
TGTGGAATTG GGAGCTTGG  AATGGATCCT
GGAGGATGCC CAATTAGGGC CTAGCCTTAA
TCAGGTCCTC AGAGAATTTC TACCATTTCA
GAGAGGCCTT TTGGAATGTG GCCCCTGAAC
AAGAATTGGA AGCTGCCCTG CCCATGGGAG
CTGGTTAGAA ATGCAGAATC CTAGGCTCCA
CCCCATCCAG TTCATGAGAA TCTATATTTA
ACAAGATCTG CAGGGGTGT  GTCTGCTCAG
TAATTTGAGG ACAACCATTC CAGACTGCTT
CCAATTTCT  GGAATACATG AAATATAGAT
CAGTTATAAG TAGCAGGCCA AGTCAGGCCC
TTATTTTCAA GAAACTGAGG AATTTCTTT
GTGTAGCTTT GCTCTTTGGT AGAAAGGCT
AGGTACACAG CTCTAGACAC TGCCACACAG
GGTCTGCAAG GTCTTTGGTT CAGCTAAGCC
GGAATTC
```

FIG. 4 (a)

```
CGGTGGCTGC   CGATGTCATT   TCCTTGCTAC
TGAACGGCGA   CGGCGGCGTT   GGCCGCCGGC
GCCTCTGGAT   CGGCCTGCAG   CTGCCACCCG
GCTGCGGCGA   CCCCAAGCGC   CTCGGGCCCC
TGCGCGGCTT   CCAGTGGGTT   ACGGGAG ACA
ACAACAGGAG   CTATAGCAGG   TGGGCACGGC
   HTM134
TCGACCTCAA   TGGGGCTCCC   CTCTGCGGCC
CGTTGTGCG T  CGCTGTCTCC   GCTGCTGAG G
               HTM135
CCACTGTGCC   CAGCGAGCCG   ATCTGGGAG G
AGCAGCAGTG   CGAAGTGAAG   GCCGATGGCT
  HTM136
TCCTCTGCGA   GTTCCACTTC   CCAGCCACCT
GCAGGCCACT   GGCTGTGGAG   CCCGGCGCCG
CGGCTGCCGC   CGTCTCGATC   ACCTACGGCA
CCCCGTTCGC   GGCCCGCGGA   GCGGACTTCC
AGGCGCTGCC   GGTGGGCAGC   TCCGCCGCGG
TGGCTCCCCT   CGGCTTACAG   CTAATGTGCA
CCGCGCCGCC   CGGAGCGGTC   CAGGGCACT
GGGCCAGGA    GGCGCCGGC    GCTTGGGACT
GCAGCGTGGA   GAACGGCGGC   TGCGAGCACG
```

FIG. 4 (b)

```
CGTGCAATGC  GATCCCTGGG  GCTCCCCGCT
GCCAGTGCCC  AGCCGGCGCC  GCCCTGCAGG
CAGACGGGCG  CTCCTGCACC  GCATCCGCGA
CGCAGTCCTG  CAACGACCTC  TGCGAGCACT
TCTGCGTTCC  CAACCCCGAC  CAGCCGGGCT
CCTACTCGTG  CATGTGCGAG  ACCGGCTACC
GGCTGGCGGC  CGACCAACAC  CGGTGCGAGG
ACGTGGATGA  CTGCATACTG  GAGCCAGTC
CGTGTCCGCA  GCGCTGTGTC  AACACACAGG
GTGGCTTCGA  GTGCCACTGC  TACCCTAACT
ACGACCTGGT  GGACGGCGAG  TGTGTGGAGC
CCGTGGACCC  GTGCTTCAGA  GCCAACTGCG
AGTACCAGTG  CCAGCCCCTG  AACCAAACTA
GCTACCTCTG  CGTCTGCGCC  GAGGGCTTCG
CGCCCATTCC  CCACGAGCCG  CACAGGTGCC
AGATGTTTTG  CAACCAGACT  GCCTGTC
```

FIG. 5

```
GGCCCTGTCG   CAGTGCCCGC   GCTTTCCCCG
GCGCCTGCAC   GCGGCGCGCC   TGGGTAACAT
GCTTGGGGTC   CTGGTCCTTG   GCGCGCTGGC
CCTGGCCGGC   CTGGGGTTCC   CCGCACCCGC
AGAGCCGCAG   CCGGGTGGCA   GCCAGTGCGT
CGAGCACGAC   TGCTTCGCGC   TCTACCCGGG
CCCCGCGACC   TTCCTCAATG   CCAGTCAGAT
CTGCGACGGA   CTGCGGGCC    ACCTAATGAC
AGTGCGCTCC   TCGGTGGCTG   CCGATGTCAT
TTCCTTGCTA   CTGAACGGCG   ACGGCGGCGT
TGGCCGCCGG   CGCCTCTGGA   TCGGCCTGCA
GCTGCCACCC   GGCTGCGGCG   ACCCCAAGCG
CCTCGGGCCC   CTGCGGCT     TCCAGTGGGT
TACGGGAGAC   AACAACACCA   GCTATAGCAG
GTGGGCACGG   CTCGACCTCA   ATGGGCTCC
CCTCTGCGGC   CCGTTGTGCG   TCGCTGTCTC
CGCTGCTGAG   GCCACTGTGC   CCAGCGAGCC
GATCTGGGAG   GAGCAGCAGT   GCGAAGTGAA
```

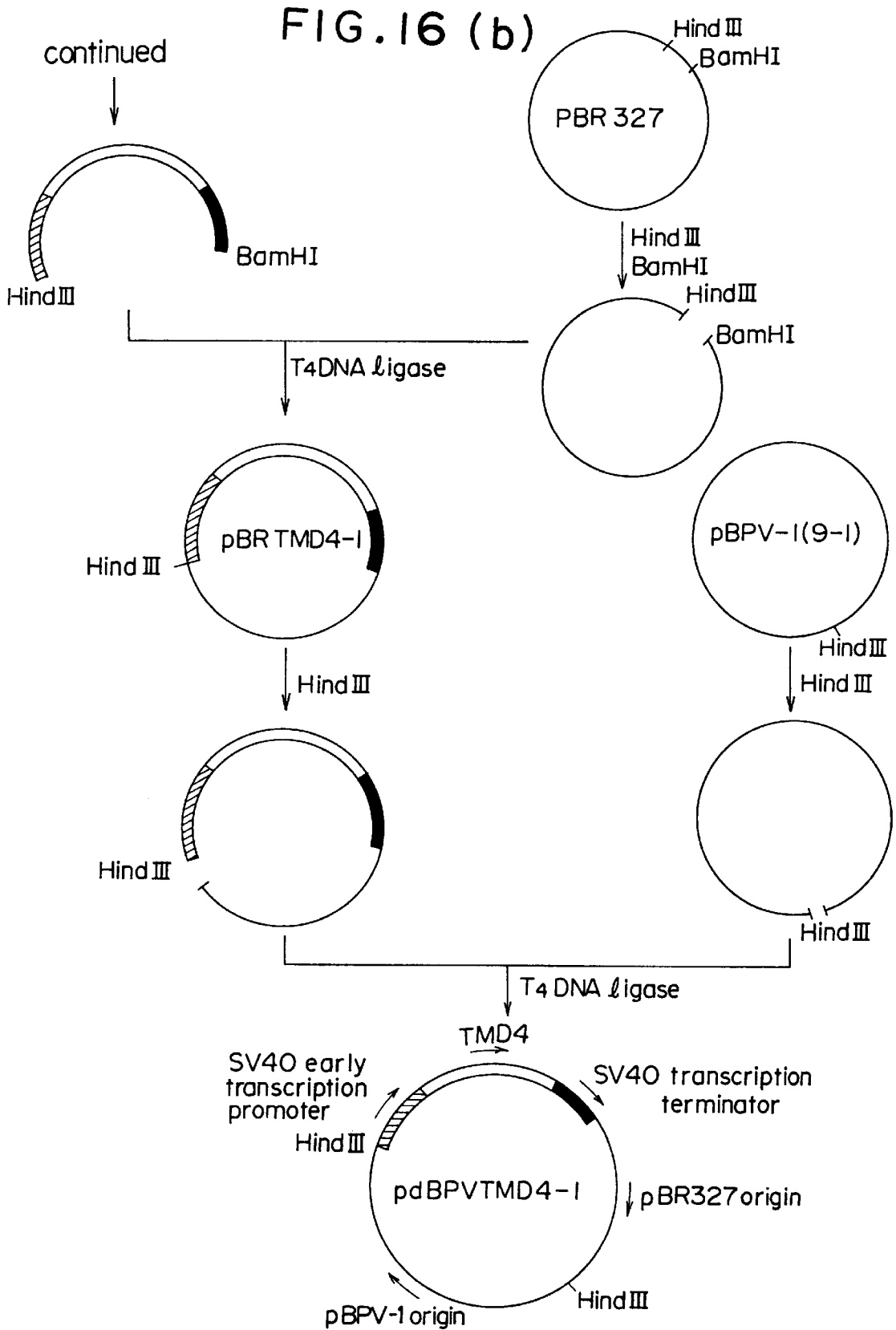

PEPTIDE HAVING AN ABILITY TO PROMOTE THE ACTIVATION OF PROTEIN C BY THROMBIN

This application is a divisional, of application Ser. No. 07/908,887 filed on Jul. 7, 1992, now abandoned which is a Rule 62 continuation of Ser. No. 07/243,297 filed Aug. 17, 1988, now abandoned.

FIELD OF THE INVENTION

The present invention relates to a novel peptide having an ability to promote the activation of protein C by thrombin. More particularly, the present invention is concerned with a peptide which has thrombolytic, anticoagulant and platelet aggregation-inhibiting activities and is useful for the treatment of circulatory organ diseases. The present invention also relates to a deoxyribonucleic acid (hereinafter referred to as "DNA") coding for the novel peptide, a replicable recombinant DNA containing the DNA, a microorganism or cell transformed with the replicable recombinant DNA, and a process for producing the peptide by recombinant DNA techniques.

In the present specification, amino acids and peptides are represented using abbreviations, as indicated below, approved by the IUPAC-IUB Commission on Biochemical Nomenclature (CBN). With respect to amino acids and the like having isomers, those represented by the following abbreviations are of the L-configuration unless otherwise specified. Further, unless otherwise specified, the left end and right end of the amino acid sequences of peptides are the N-terminus and C-terminus, respectively.

Gln: glutamine residue
Asp: Aspartic acid residue
Pro: proline residue
Tyr: tyrosine residue
Val: valine residue
Lys: lysine residue
Glu: glutamic acid residue
Ala: alanine residue
Asn: asparagine residue
Leu: leucine residue
Phe: phenylalanine residue
Gly: glycine residue
His: histidine residue
Ser: serine residue
Thr: threonine residue
Ile: isoleucine residue
Trp: tryptophan residue
Arg: arginine residue
Met: methionine residue
Cys: cysteine residue Polydeoxyribonucleotides and oligodeoxyribonucleotides are represented by sequences of deoxynucleotide residues which are abbreviated as follows:

A: 2'-deoxyadenylic acid residue
C: 2'-deoxycytidylic acid residue
G: 2'-deoxyguanylic acid residue
T: thymidylic acid residue Unless otherwise specified, the left end and the right end of the sequence of deoxynucleotides are the 5' end and 3' end, respectively.

PRIOR ART

Thrombolytic drugs presently in use include streptokinase and urokinase. As anticoagulants, heparin and warfarin are in use. As drugs for inhibiting the aggregation of blood platelets, aspirin, sulfinpyrazone, dipyridamole and the like are used.

Nowadays, these thrombolytic drugs, anticoagulant drugs and drugs for inhibiting the aggregation of blood platelets are used, alone or in combination, for the treatment and prevention of diseases such as myocardial infarction, thrombosis, embolism, obstruction of peripheral blood vessels, arteriosclerosis obliterans, disseminated intravascular coagulation (DIC) syndrome, angina pectoris, transient ischemic attack and toxemia of pregnancy. However, the above-mentioned thrombolytic drugs, anticoagulants and drugs for inhibiting the aggregation of blood platelets can act on only a limited part of the complicated blood coagulation-fibrinolysis system. Therefore, it has been earnestly desired to develop a drug which acts on various parts of the blood coagulation-fibrinolysis system and has an excellent effect on the control of blood coagulation.

On the other hand, protein C is known as a protein which is dependent on vitamin K and plays an important role in the blood coagulation mechanism. In recent years, it has been reported that a substance which accelerates the activation of protein C and represses platelet activation and fibrin formation by the action of thrombin is present in rabbit lung, bovine lung, human lung, human placenta and the like and such a substance has an excellent effect on the control of blood coagulation as compared to the above-mentioned drugs. With respect to the substance present in rabbit lung, reference may be made to, for example, C. T. Esmon et al., Proc. Natl. Acad. Sci. USA, Vol. 78, p.2249 (1981); N. L. Esmon et al., J. Biol. Chem., Vol. 257, p.859 (1982); C. T. Esmon et al., J. Biol. Chem., Vol. 257, p.7944 (1982); and N. L. Esmon et al., J. Biol. Chem., Vol. 258, 12238 (1982)]. With respect to the substance present in bovine lung, reference may be made to, for example Kusumoto et al., Biochemistry, Japan, Vol. 56, p.890 (1984). Further, with respect to the substance present in human placenta, reference may be made to, for example Examined Japanese Patent Application Publication No. 5-45600; S. Kurosawa et al., Journal of Japanese Society of Hematology, Vol. 47, p.632 (1984); H. H. Salem et al., J. Biol. Chem., Vol. 259, p.12246 (1984); and S. Kurosawa et al., Thrombosis Research, Vol. 37, p.353 (1985). Moreover, with respect to the substance present in human lung, reference may be made to, for example Kusumoto et al., Biochemistry, Japan, Vol. 57, p.1102 (1985).

The above-mentioned prior art references disclose the general properties of the above-mentioned substances. However, the structures of the substances, such as amino acid sequence, have not yet been elucidated and the substances have not yet been identified. Therefore, it is unclear whether or not the substances reported in the above-mentioned prior art references are the same single substances and whether or not the substances can be reproduced according to the description of the prior art references.

DISCLOSURE OF THE PRESENT INVENTION

The present inventors have made extensive and intensive studies with a view toward developing a substance which not only can activate protein C which is one of the factors relating to the blood coagulation-fibrinolysis system and is therefore capable of substantially inhibiting blood coagulation, but also can promote fibrinolysis. As a result, it has unexpectedly been found that a novel peptide comprising a specific amino acid sequence as mentioned later is capable of not only promoting the activation of protein C by thrombin, thereby inhibiting blood coagulation, but also promoting fibrinolysis, and that such a peptide is useful as a drug for controlling blood coagulation. Further, it has also been found that the peptide can be easily produced on a large scale by recombinant DNA techniques. The present invention has been completed based on such novel findings.

Accordingly, an object of the present invention is to provide a novel peptide having an ability to promote the activation of protein C by thrombin.

Another object of the present invention is to provide a DNA coding for the above-mentioned peptide.

Still another object of the present invention is to provide a replicable recombinant DNA comprising a DNA coding for the peptide.

A further object of the present invention is to provide a microorganism or cell transformed with a recombinant DNA of the kind as mentioned above.

Still a further object of the present invention is to provide a process for producing a peptide of the kind as mentioned above.

Essentially, according to the present invention, there is provided a peptide having an ability to promote the activation of protein C by thrombin, which comprises an amino acid sequence represented by the formula (I):

Val Glu Pro Val Asp Pro Cys Phe Arg Ala    (I)

Asn Cys Glu Tyr Gln Cys Gln Pro Leu Asn

Gln Thr Ser Tyr Leu Cys Val Cys Ala Glu

Gly Phe Ala Pro Ile Pro His Glu Pro His

Arg Cys Gln Met Phe Cys Asn Gln Thr Ala

Cys Pro Ala Asp Cys Asp Pro Asn Thr Gln

Ala Ser Cys Glu Cys Pro Glu Gly Tyr Ile

Leu Asp Asp Gly Phe Ile Cys Thr Asp Ile

Asp Glu Cys Glu Asn Gly Gly Phe Cys Ser

Gly Val Cys His Asn Leu Pro Gly Thr Phe

Glu Cys Ile Cys Gly Pro Asp Ser Ala Leu

Val Arg His Ile Gly Thr Asp Cys, or homologous variants of said peptide.

The peptide of the present invention comprises an amino acid sequence represented by the above-mentioned formula (I). The peptide of the present invention may consist essentially of the amino acid sequence represented by the formula (I). Alternatively, the peptide of the present invention may be in the form of a peptide comprising the amino acid sequence of the formula (I) and, attached thereto at its N-terminus and/or C-terminus, at least one amino acid sequence of other peptides. Examples of peptides comprising the amino acid sequence of the formula (I) and at least one amino acid sequence of other peptides include the following peptides (1) to (4).

(1) A peptide comprising an amino acid sequence of the formula (I) and, attached thereto at its N-terminus, an amino acid sequence represented by the following formula:

Cys Ser Val Glu Asn Gly Gly Cys Glu His

Ala Cys Asn Ala Ile Pro Gly Ala Pro Arg

Cys Gln Cys Pro Ala Gly Ala Ala Leu Gln

Ala Asp Gly Arg Ser Cys Thr Ala Ser Ala

Thr Gln Ser Cys Asn Asp Leu Cys Glu His

Phe Cys Val Pro Asn Pro Asp Gln Pro Gly

Ser Tyr Ser Cys Met Cys Glu Thr Gly Tyr

Arg Leu Ala Ala Asp Gln His Arg Cys Glu

Asp Val Asp Asp Cys Ile Leu Glu Pro Ser

Pro Cys Pro Gln Arg Cys Val Asn Thr Gln

Gly Gly Phe Glu Cys His Cys Tyr Pro Asn

Tyr Asp Leu Val Asp Gly Glu Cys (2) A peptide comprising an amino acid sequence of the formula (I) and, attached thereto at its N-terminus and C-terminus, amino acid sequences represented by the following formulae:

Cys Ser Val Glu Asn Gly Gly Cys Glu His

Ala Cys Asn Ala Ile Pro Gly Ala Pro Arg

Cys Gln Cys Pro Ala Gly Ala Ala Leu Gln

Ala Asp Gly Arg Ser Cys Thr Ala Ser Ala

Thr Gln Ser Cys Asn Asp Leu Cys Glu His

Phe Cys Val Pro Asn Pro Asp Gln Pro Gly

Ser Tyr Ser Cys Met Cys Glu Thr Gly Tyr

Arg Leu Ala Ala Asp Gln His Arg Cys Glu

Asp Val Asp Asp Cys Ile Leu Glu Pro Ser

Pro Cys Pro Gln Arg Cys Val Asn Thr Gln

Gly Gly Phe Glu Cys His Cys Tyr Pro Asn

Tyr Asp Leu Val Asp Gly Glu Cys, and

Asp Ser Gly Lys Val Asp Gly Gly Asp Ser

Pro Gly Ser Gly Glu Pro Pro Ala Val

Gly Leu Val His Ser Gly, respectively.

(3) A peptide comprising an amino acid sequence of the formula (I) and, attached thereto at its N-terminus and C-terminus, amino acid sequences represented by the following formulae:

Ala Pro Ala Glu Pro Gln Pro Gly Gly Ser

Gln Cys Val Glu His Asp Cys Phe Ala Leu

Tyr Pro Gly Pro Ala Thr Phe Leu Asn Ala

Ser Gln Ile Cys Asp Gly Leu Arg Gly His

Leu Met Thr Val Arg Ser Ser Val Ala Ala

Asp Val Ile Ser Leu Leu Leu Asn Gly Asp

Gly Gly Val Gly Arg Arg Arg Leu Trp Ile

Gly Leu Gln Leu Pro Pro Gly Cys Gly Asp

Pro Lys Arg Leu Gly Pro Leu Arg Gly Phe

-continued

```
Gln Trp Val Thr Gly Asp Asn Asn Thr Ser
Tyr Ser Arg Trp Ala Arg Leu Asp Leu Asn
Gly Ala Pro Leu Cys Gly Pro Leu Cys Val
Ala Val Ser Ala Ala Glu Ala Thr Val Pro
Ser Glu Pro Ile Trp Glu Glu Gln Gln Cys
Glu Val Lys Ala Asp Gly Phe Leu Cys Glu
Phe His Phe Pro Ala Thr Cys Arg Pro Leu
Ala Val Glu Pro Gly Ala Ala Ala Ala Ala
Val Ser Ile thr Tyr Gly Thr Pro Phe Ala
Ala Arg Gly Ala Asp Phe Gln Ala Leu Pro
Val Gly Ser Ser Ala Ala Val Ala Pro Leu
Gly Leu Gln Leu Met Cys Thr Ala Pro Pro
Gly Ala Val Gln Gly His Trp Ala Arg Glu
Ala Pro Gly Ala Trp Asp Cys Ser Val Glu
Asn Gly Gly Cys Glu His Ala Cys Asn Ala
Ile Pro Gly Ala Pro Arg Cys Gln Cys Pro
Ala Gly Ala Ala Leu Gln Ala Asp Gly Arg
Ser Cys Thr Ala Ser Ala Thr Gln Ser Cys
Asn Asp Leu Cys Glu His Phe Cys Val Pro
Asn Pro Asp Gln Pro Gly Ser Tyr Ser Cys
Met Cys Glu Thr Gly Tyr Arg Leu Ala Ala
Asp Gln His Arg Cys Glu Asp Val Asp Asp
Cys Ile Leu Glu Pro Ser Pro Cys Pro Gln
Arg Cys Val Asn Thr Gln Gly Gly Phe Glu
Cys His Cys Tyr Pro Asn Tyr Asp Leu Val
Asp Gly Glu Cys, and
Asp Ser Gly Lys Val Asp Gly Gly Asp Ser
Gly Ser Gly Glu Pro Pro Pro Ser Pro Thr
Pro Gly Ser Thr Leu Thr Pro Pro Ala Val
Gly Leu Val His Ser Gly, respectively.
```

(4) A peptide comprising an amino acid sequence of the formula (I) and, attached thereto at its N-terminus and C-terminus, amino acid sequences represented by the following formulae:

```
Ala Pro Ala Glu Pro Gln Pro Gly Gly Ser
Gln Cys Val Glu His Asp Cys Phe Ala Leu
Tyr Pro Gly Pro Ala Thr Phe Leu Asn Ala
Ser Gln Ile Cys Asp Gly Leu Arg Gly His
Leu Met Thr Val Arg Ser Ser Val Ala Ala
Asp Val Ile Ser Leu Leu Leu Asn Gly Asp
Gly Gly Val Gly Arg Arg Arg Leu Trp Ile
Gly Leu Gln Leu Pro Pro Gly Cys Gly Asp
Pro Lys Arg Leu Gly Pro Leu Arg Gly Phe
Gln Trp Val Thr Gly Asp Asn Asn Thr Ser
Tyr Ser Arg Trp Ala Arg Leu Asp Leu Asn
Gly Ala Pro Leu Cys Gly Pro Leu Cys Val
Ala Val Ser Ala Ala Glu Ala Thr Val Pro
Ser Glu Pro Ile Trp Glu Glu Gln Gln Cys
Glu Val Lys Ala Asp Gly Phe Leu Cys Glu
Phe His Phe Pro Ala Thr Cys Arg Pro Leu
Ala Val Glu Pro Gly Ala Ala Ala Ala Ala
Val Ser Ile thr Tyr Gly Thr Pro Phe Ala
Ala Arg Gly Ala Asp Phe Gln Ala Leu Pro
Val Gly Ser Ser Ala Ala Val Ala Pro Leu
Gly Leu Gln Leu Met Cys Thr Ala Pro Pro
Gly Ala Val Gln Gly His Trp Ala Arg Glu
Ala Pro Gly Ala Trp Asp Cys Ser Val Glu
Asn Gly Gly Cys Glu His Ala Cys Asn Ala
Ile Pro Gly Ala Pro Arg Cys Gln Cys Pro
Ala Gly Ala Ala Leu Gln Ala Asp Gly Arg
Ser Cys Thr Ala Ser Ala Thr Gln Ser Cys
Asn Asp Leu Cys Glu His Phe Cys Val Pro
Asn Pro Asp Gln Pro Gly Ser Tyr Ser Cys
Met Cys Glu Thr Gly Tyr Arg Leu Ala Ala
Asp Gln His Arg Cys Glu Asp Val Asp Asp
Cys Ile Leu Glu Pro Ser Pro Cys Pro Gln
Arg Cys Val Asn Thr Gln Gly Gly Phe Glu
Cys His Cys Tyr Pro Asn Tyr Asp Leu Val
Asp Gly Glu Cys, and
Asp Ser Gly Lys Val Asp Gly Gly Asp Ser
Gly Ser Gly Glu Pro Pro Pro Ser Pro Thr
Pro Gly Ser Thr Leu Thr Pro Pro Ala Val
Gly Leu Val His Ser Gly Leu Leu Ile Gly
Ile Ser Ile Ala Ser Leu Cys Leu Val Val
Ala Leu Leu Ala Leu Leu Cys His Leu Arg
Lys Lys Gln Gly Ala Ala Arg Ala Lys Met
Glu Tyr Lys Cys Ala Ala Pro Ser Lys Glu
Val Val Leu Gln His Val Arg Thr Glu Arg
Thr Pro Gln Arg Leu, respectively.
```

The peptide of the present invention may contain the amino acid methionine as the N-terminal amino acid residue.

Further, the peptide of the present invention may also comprise a leader sequence having, for example, an amino acid sequence represented by the following formula as an N-terminal amino acid sequence:

Met Leu Gly Val Leu Val Leu Gly Ala Leu Ala Leu Ala Gly Leu Gly Phe Pro.

It is possible to change part of the structure of the peptide by natural or artificial mutation without significant change of the activity of the peptide. The peptide of the present invention includes peptides having a structure corresponding to homologous variants of the peptide having the above-mentioned amino acid sequence.

The peptide of the present invention may or may not contain at least one sugar residue.

In another aspect of the present invention, there is provided a deoxyribonucleic acid comprising a base sequence represented by the following formula (II):

GTGGAGCC CGTGGACCCG TGCTTCAGAG CCAACTGCGA    (II)

GTACCAGTCG CAGCCCCTGA ACCAAACTAG CTACCTCTGC

GTCTGCGCCG AGGGCTTCGC GCCCATTCCC CACGAGCCGC

ACAGGTGCCA GATGTTTTGC AACCAGACTG CCTGTCCAGC

CGACTGCGAC CCCAACACCC AGGCTAGCTG TGAGTGCCCT

GAAGGCTACA TCCTGGACGA CGGTTTCATC TGCACGGACA

TCGACGAGTG CGAAAACGGC GGCTTCTGCT CCGGGGTGTG

CCACAACCTC CCCGGTACCT TCGAGTGCAT CTGCGGGCCC

GACTCGGCCC TTGTCCGCCA CATTGGCACC GACTGT..., said base sequence being unsubstituted or substituted at least at its one base in accordance with the degeneracy of the Genetic Code.

The deoxyribonucleic acid (DNA) of the present invention comprises a base sequence of the above-mentioned formula (II). The base sequence of the formula (II) codes for the amino acid sequence represented by the formula (I) mentioned above. The DNA of the present invention may comprise the base sequence represented by the formula (II) and, attached thereto at its 5' and/or 3' end, at least one base sequence other than that of the formula (II). Examples of DNA's comprising a base sequence of the formula (II) and at least one base sequence other than that of the formula (II) include the following DNA's (1) to (4).

(1) a DNA comprising a base sequence of the formula (II) and, attached thereto at its 5' end, a base sequence represented by the following formula:

TG CAGCGTGGAG AACGGCGGCT GCGAGCACGC

GTGCAATGCG ATCCCTGGGG CTCCCCGCTG CCAGTGCCCA

GCCGGCGCCG CCCTGCAGGC AGACGGGCGC TCCTGCACCG

CATCCGCGAC GCAGTCCTGC AACGACCTCT GCGAGCACTT

CTGCGTTCCC AACCCCGACC AGCCGGGCTC CTACTCGTGC

ATGTGCGAGA CCGGCTACCG GCTGGCGGCC GACCAACACC

GGTGCGAGGA CGTGGATGAC TGCATACTGG AGCCCAGTCC

GTGTCCGCAG CGCTGTGTCA ACACACAGGG TGGCTTCGAG

TGCCACTGCT ACCCTAACTA CGACCTGGTG GACGGCGAGT

GT (2) a DNA comprising a base sequence of the formula (II) and, attached thereto at its 5' end and 3' end, base sequences represented by the following formulae:

TG CAGCGTGGAG AACGGCGGCT GCGAGCACGC

GTGCAATGCG ATCCCTGGGG CTCCCCGCTG CCAGTGCCCA

GCCGGCGCCG CCCTGCAGGC AGACGGGCGC TCCTGCACCG

CATCCGCGAC GCAGTCCTGC AACGACCTCT GCGAGCACTT

CTGCGTTCCC AACCCCGACC AGCCGGGCTC CTACTCGTGC

ATGTGCGAGA CCGGCTACCG GCTGGCGGCC GACCAACACC

GGTGCGAGGA CGTGGATGAC TGCATACTGG AGCCCAGTCC

GTGTCCGCAG CGCTGTGTCA ACACACAGGG TGGCTTCGAG

TGCCACTGCT ACCCTAACTA CGACCTGGTG GACGGCGAGT

GT, and

GACT CCGGCAAGGT GGACGGTGGC GACAGCGGCT

CTGGCGAGCC CCCGCCCAGC CCGACGCCCG GCTCCACCTT

GACTCCTCCG GCCGTGGGGC TCGTGCATTC GGGC, respectively.

(3) a DNA comprising a base sequence of the formula (II) and, attached thereto at its 5' end and 3' end, base sequences represented by the following formulae:

GCACCCGCAG AGCCGCAGCC GGGTGGCAGC CAGTGCGTCG

AGCACGACTG CTTCGCGCTC TACCCGGGCC CCGCGACCTT

CCTCAATGCC AGTCAGATCT GCGACGGACT GCGGGGCCAC

CTAATGACAG TGCGCTCCTC GGTGGCTGCC GATGTCATTT

CCTTGCTACT GAACGGCGAC GGCGGCGTTG GCCGCCGGCG

CCTCTGGATC GGCCTGCAGC TGCCACCCGG CTGCGGCGAC

CCCAAGCGCC TCGGGCCCCT GCGCGGCTTC CAGTGGGTTA

CGGGAGACAA CAACACCAGC TATAGCAGGT GGGCACGGCT

CGACCTCAAT GGGGCTCCCC TCTGCGGCCC GTTGTGCGTC

GCTGTCTCCG CTGCTGAGGC CACTGTGCCC AGCGAGCCGA

TCTGGGAGGA GCAGCAGTGC GAAGTGAAGG CCGATGGCTT

CCTCTGCGAG TTCCACTTCC CAGCCACCTG CAGGCCACTG

GCTGTGGAGC CCGGCGCCGC GGCTGCCGCC GTCTCGATCA

CCTACGGCAC CCCGTTCGCG GCCCGCGGAG CGGACTTCCA

GGCGCTGCCG GTGGGCAGCT CCGCCGCGGT GGCTCCCCTC

GGCTTACAGC TAATGTGCAC CGCGCCGCCC GGAGCGGTCC

AGGGGCACTG GGCCAGGGAG GCGCCGGGCG CTTGGGACTG

CAGCGTGGAG AACGGCGGCT GCGAGCACGC GTGCAATGCG

ATCCCTGGGG CTCCCCGCTG CCAGTGCCCA GCCGGCGCCG

CCCTGCAGGC AGACGGGCGC TCCTGCACCG CATCCGCGAC

GCAGTCCTGC AACGACCTCT GCGAGCACTT CTGCGTTCCC

AACCCCGACC AGCCGGGCTC CTACTCGTGC ATGTGCGAGA

CCGGCTACCG GCTGGCGGCC GACCAACACC GGTGCGAGGA

CGTGGATGAC TGCATACTGG AGCCCAGTCC GTGTCCGCAG

-continued

```
CGCTGTGTCA ACACACAGGG TGGCTTCGAG TGCCACTGCT

ACCCTAACTA CGACCTGGTG GACGGCGAGT GT, and

GACT CCGGCAAGGT GGACGGTGGC GACAGCGGCT

CTGGCGAGCC CCCGCCCAGC CCGACGCCCG GCTCCACCTT

GACTCCTCCG GCCGTGGGGC TCGTGCATTC GGGC,
``` respectively.

(4) a DNA comprising a base sequence of the formula (II) and, attached thereto at its 5' end and 3' end, base sequences represented by the following formulae:

```
GCACCCGCAG AGCCGCAGCC GGGTGGCAGC CAGTGCGTCG

AGCACGACTG CTTCGCGCTC TACCCGGGCC CCGCGACCTT

CCTCAATGCC AGTCAGATCT GCGACGGACT GCGGGGCCAC

CTAATGACAG TGCGCTCCTC GGTGGCTGCC GATGTCATTT

CCTTGCTACT GAACGGCGAC GGCGGCGTTG GCCGCCGGCG

CCTCTGGATC GGCCTGCAGC TGCCACCCGG CTGCGGCGAC

CCCAAGCGCC TCGGGCCCCT GCGCGGCTTC CAGTGGGTTA

CGGGAGACAA CAACACCAGC TATAGCAGGT GGGCACGGCT

CGACCTCAAT GGGGCTCCCC TCTGCGGCCC GTTGTGCGTC

GCTGTCTCCG CTGCTGAGGC CACTGTGCCC AGCGAGCCGA

TCTGGGAGGA GCAGCAGTGC GAAGTGAAGG CCGATGGCTT

CCTCTGCGAG TTCCACTTCC CAGCCACCTG CAGGCCACTG

GCTGTGGAGC CCGGCGCCGC GGCTGCCGCC GTCTCGATCA

CCTACGGCAC CCCGTTCGCG GCCCGCGGAG CGGACTTCCA

GGCGCTGCCG GTGGGCAGCT CCGCCGCGGT GGCTCCCCTC

GGCTTACAGC TAATGTGCAC CGCGCCGCCC GGAGCGGTCC

AGGGGCACTG GGCCAGGGAG GCGCCGGGCG CTTGGGACTG

CAGCGTGGAG AACGGCGGCT GCGAGCACGC GTGCAATGCG

ATCCCTGGGG CTCCCCGCTG CCAGTGCCCA GCCGGCGCCG

CCCTGCAGGC AGACGGGCGC TCCTGCACCG CATCCGCGAC

GCAGTCCTGC AACGACCTCT GCGAGCACTT CTGCGTTCCC

AACCCCGACC AGCCGGGCTC CTACTCGTGC ATGTGCGAGA

CCGGCTACCG GCTGGCGGCC GACCAACACC GGTGCGAGGA

CGTGGATGAC TGCATACTGG AGCCCAGTCC GTGTCCGCAG

CGCTGTGTCA ACACACAGGG TGGCTTCGAG TGCCACTGCT

ACCCTAACTA CGACCTGGTG GACGGCGAGT GT, and

GACT CCGGCAAGGT GGACGGTGGC GACAGCGGCT

CTGGCGAGCC CCCGCCCAGC CCGACGCCCG GCTCCACCTT

GACTCCTCCG GCCGTGGGGC TCGTGCATTC GGGCTTGCTC

ATAGGCATCT CCATCGCGAG CCTGTGCCTG GTGGTGGCGC

TTTTGGCGCT CCTCTGCCAC CTGCGCAAGA AGCAGGGCGC

CGCCAGGGCC AAGATGGAGT ACAAGTGCGC GGCCCCTTCC
```

-continued
```
AAGGAGGTAG TGCTGCAGCA CGTGCGGACC GAGCGGACGC

CGCAGAGACT C, respectively.
```

The above-mentioned DNA of the present invention may be used for producing the peptides as mentioned above by recombinant DNA techniques. The DNA of the present invention may be obtained as follows.

[1] Using an antibody specific for a human lung-derived peptide capable of promoting the activation of protein C by thrombin, which antibody is obtained from a rabbit, a DNA fragment which codes for a peptide capable of bonding to the antibody is isolated from a cDNA library prepared from a human lung, and the isolated cDNA fragment is analyzed with respect to its base sequence. The thus obtained cDNA fragment codes for part of a human lung-derived peptide capable of promoting the activation of protein C by thrombin, which part does not include the N-terminus of the peptide but includes the C-terminus of the peptide.

[2] As mentioned above, the thus obtained cDNA fragment does not code for the entire amino acid sequence of the human lung-derived peptide and lacks the base sequence corresponding to the N-terminal amino acid sequence of the peptide. Therefore, a cDNA fragment coding for the N-terminal amino acid sequence is obtained according to a customary primer extension method utilizing the cDNA fragment obtained in the above step [1] as follows. First, a DNA corresponding to a part of the cDNA fragment obtained in step [1] is organo-chemically synthesized, which part codes for an amino acid sequence on the N-terminal side. Second, according to a customary primer extension method using the synthesized DNA as a primer, another cDNA fragment having a base sequence upstream of the 5' end of the cDNA fragment obtained in step [1] is obtained from a poly(A)+RNA which has been prepared from an endothelial cell of a human umbilical cord. Repeating the primer extension as mentioned above, a cDNA fragment coding for the N-terminal amino acid sequence of the human lung-derived peptide is obtained.

[3] Then, the cDNA fragments obtained in steps [1] to [2] are ligated so that the resulting cDNA fragment can code for an entire amino acid sequence of the desired peptide. Thus, there is obtained a cDNA (hereinafter referred to as "cDNA-A") comprising an open reading frame of 1671 base pairs (hereinafter referred to as "bp") beginning from the codon of the N-terminal amino acid. The base sequence of the open reading frame is the same as that of DNA (4) mentioned above. From the cDNA-A, cDNA's respectively comprising the same base sequences as that of the formula (II) and those of DNA's (1) to (3) mentioned above can be prepared as follows.

(i) A cDNA comprising the same base sequence as that of DNA (3) is obtained by deleting, from the cDNA-A, a part downstream from the 1495th base counted from the 5' end of the cDNA-A by the technique of site-directed mutagenesis. The thus obtained cDNA is of 1494 bp including the codon of the N-terminal amino acid at its 5' end.

(ii) A cDNA comprising the same base sequence as that of DNA (2) is obtained by deleting, from the cDNA of 1494 bp as obtained in item (i) above, a part comprised of 678 bp corresponding to the N-terminal amino acid sequence by the technique of site-directed mutagenesis. The thus obtained cDNA is of 816 bp.

(iii) A cDNA comprising the same base sequence as that of DNA (1) is obtained as follows. First, a part downstream from the 1387th base counted from the 5' end of the cDNA-A is deleted from the cDNA-A by the technique of site-directed mutagenesis to thereby obtain a cDNA of 1386 bp including the codon of the N-terminal amino acid as the 5'end base sequence. Next, from the thus obtained cDNA of 1386 bp, a part comprised of 678 bp corresponding to the N-terminal amino acid sequence is deleted by the technique of site-directed mutagenesis. Thus, there is obtained a cDNA of 708 bp.

(iv) A cDNA comprising the same base sequence as that represented by formula (II) is obtained as follows. First, a cDNA of 1386 bp is obtained in the same manner as in item (iii) mentioned above. Then, from the thus obtained cDNA of 1386 bp, a part comprised of 1032 bp corresponding to the N-terminal amino acid sequence is deleted by the technique of site-directed mutagenesis. Thus, there is obtained a cDNA of 354 bp.

The base sequence of each of the cDNA's obtained above is analyzed by a customary method to confirm that the cDNA's have the same base sequences as those of DNA's (1) to (4) and that of formula (II), respectively.

The above-mentioned DNA's of the present invention may also be prepared by organo-chemical synthesis. Further, the DNA's of the present invention may be prepared from a precursor DNA without carrying out the above-mentioned primer extension. The precursor DNA may be obtained from a human chromosomal DNA library by a customary hybridization method in which as a probe, use is made of a DNA fragment obtained in the above-mentioned step [1], or a synthetic DNA prepared based on the base sequence of the DNA fragment.

The above-mentioned DNA of the present invention comprising the base sequence of formula (II) may further comprise a base sequence coding for a leader sequence represented by, for example, the following formula:
  Met Leu Gly Val Leu Val Leu Gly Ala Leu Ala Leu Ala
    Gly Leu Gly Phe Pro,
as the 5' end base sequence.

According to the present invention, a complementary DNA to the above-mentioned DNA is also provided. According to the present invention, the above-mentioned DNA and the complementary DNA may be complementarily bonded to each other to form a double-stranded DNA.

The structure of the DNA and the structure of the peptide deduced therefrom may be partially changed by natural or artificial mutation without causing the main activity of the peptide to be changed. Hence, the DNA of the present invention may alternatively have a base sequence that codes for a peptide having a structure corresponding to that of a homologous variant of any of the aforementioned peptides.

In accordance with the degeneracy of the Genetic Code, it is possible to substitute at least one base of the base sequence of a gene by another type of base without causing the amino acid sequence of the peptide produced from the gene to be changed. Hence, the DNA of the present invention may also have any base sequence that has been changed by substitution in accordance with the degeneracy of the Genetic Code. In this instance, the amino acid sequence deduced from the base sequence obtained by the above-mentioned substitution is identical with the amino acid sequence as defined before.

In a further aspect of the present invention, there is provided a replicable recombinant DNA which comprises the above-mentioned deoxyribonucleic acid according to the present invention and a replicable expression vector. The recombinant DNA is capable, in a transformed microorganism or cell, of expressing a peptide of the present invention. Examples of suitable expression vectors include plasmids pBR322, pBR327, YRp7, pSV2-dhfr (ATCC 37146), pBPV-1(9-1) (ATCC 37111) and the like. In this connection, it is necessary to select an expression vector suitable for a microorganism or cell to be used as a host.

Further, the present invention is also directed to a microorganism or cell transformed with the above-mentioned replicable recombinant DNA. Examples of microorganisms include $Escherichia\ coli$ strains such as $E.\ coli$ K12 strain 294 (ATCC 31446), $E.\ coli\ \chi 1776$ (ATCC 31537), $E.\ coli$ B, $E.\ coli$ C600, $E.\ coli$ C600hf1 and $E.\ coli$ W3110 (F$^-$, $\lambda^-$, prototrophic, ATCC 27325); bacteria belonging to the genus Bacillus such as $Bacillus\ subtilis$; Enterobacteria other than $E.\ coli$ strains, such as $Salmonella\ typhimurium$ and $Serratia\ marcesans$; bacteria belonging to the genus Pseudomonas; and $Saccharomyces\ cerevisiae$. Examples of cells include cells of animal cell lines such as cell lines VERO (ATCC CCL-81) and HeLa, Chinese hamster ovary (CHO) cell strains, and cell lines WI38, BHK, COS-7, MDCK and the like.

In still a further aspect of the present invention, there is provided a process for producing the peptide of the present invention which comprises:

(a) ligating a deoxyribonucleic acid comprising a base sequence coding for the peptide to a replicable expression vector to obtain a replicable recombinant DNA comprising said deoxyribonucleic acid and said replicable expression vector;

(b) transforming cells of a microorganism or cell culture with said replicable recombinant DNA to form transformants;

(c) selecting said transformants from parent cells;

(d) culturing said transformants, causing said transformants to express said deoxyribonucleic acid and produce a peptide; and (e) isolating said peptide from the culture of said transformants.

According to the method of the present invention, the above-mentioned DNA of the present invention is ligated to a replicable expression vector at its portion downstream of the DNA region of the vector including a promoter etc. so that the DNA of the present invention can be transcribed properly into mRNA and the proper translation of the mRNA into a peptide can be attained. Thus, a replicable expression vector containing the above-mentioned DNA is obtained. Then, cells of a microorganism or cell culture are transformed with the thus obtained replicable recombinant DNA to obtain a transformed microorganism or cell containing the recombinant DNA. The thus obtained transformant is isolated from the parent cells of the microorganism or cell by means of at least one phenotypical trait imparted with the recombinant DNA. The obtained transformant is grown to effect expression of the genetic information that is encoded by the above-mentioned deoxyribonucleic acid, thereby producing a peptide of the present invention.

For cloning the DNA of the present invention and DNA sequences necessary for constructing the recombinant DNA, for example, a promoter, an origin of replication, etc., it is preferred to use a host-vector system, in which a prokaryotic cell is employed as a host. Examples of prokaryotic cells include $Escherichia\ coli$ strains such as $E.\ coli$ K12 strain 294 (ATCC 31446), $E.\ coli$ B, $E.\ coli\ \chi 1776$ 8ATCC 31537), $E.\ coli$ C600, $E.\ coli$ C600hf1 and $E.\ coli$ W3110 (F$^-$, $\lambda^-$, prototrophic, ATCC 27375); bacteria belonging to the genus Bacillus such as $Bacillus\ subtilis$; Enterobacteria other than $E.\ coli$, such as $Salmonella\ typhimurium$ and $Serratia\ marcesans$; bacteria belonging to the genus Pseudomonas and $Saccharomyces\ cerevisiae$. Among the above-mentioned bacteria, most preferred is $E.\ coli$ K12 strain 294. In the case where the above-mentioned microorganism is used as a host, a plasmid vector suitable for the above-mentioned microorganism is generally employed as a replicable expression vector for the recombinant DNA. For example, as the plasmid vector for transforming an *E. coli* strain, plasmids pBR322 and pBR327 may be used. A plasmid vector generally contains an origin of replication, a promoter and a marker gene which imparts to the recombinant DNA a phenotypical trait useful for selecting a cell transformed with the recombinant DNA. Examples of promoters include a β-lactamase and lactose promoter, a tryptophan promoter and the like. Examples of marker genes include a gene for ampicillin resistance, a gene for tetracycline resistance and the like. On the other hand, for expressing the DNA of the present invention to produce the peptide of the present invention, there may be used not only the above-mentioned host-vector system in which a prokaryotic cell is employed as a host, but also a host-vector system in which a eukaryotic cell such as cells derived from vertebrates is employed as a host. Examples of eukaryotic cells include cells such as the animal cell lines as mentioned before. In order to express the DNA of the present invention in the above-mentioned eukaryotic host cell, the recombinant DNA of the present invention generally contains functional sequences for controlling gene expression, such as an origin of replication, a promoter which is to be located upstream of the DNA of the present invention, a ribosome-binding site, a polyadenylation site and a transcription termination sequence. Such functional sequences to be used for expressing the DNA of the present invention in a eukaryotic cell may be obtained from a virus or viral substance.

For example, a promoter which can be used in the present invention may be obtained from adenovirus 2, polyoma virus, simian virus 40 (SV40) and the like. Specifically, the major late promoter of adenovirus 2 and the early promoter and late promoter of SV40 are preferred. Further, there may also be employed a promoter which is inherently present at a portion upstream of a gene which codes for a human lung-derived peptide having an ability to promote the activation of protein C by thrombin, as long as the promoter is suitable for use in the above-mentioned host-vector system.

With respect to an origin of replication, there may be employed endogenous origins, for example, replication origins derived from a virus such as adenovirus, polyoma virus, SV40, vesicular stomatitis virus (VSV) and bovine papilloma virus (BPV). Alternatively, when a vector having such a property that it can be integrated into a host chromosome is used as an expression vector, the origin of replication of a host chromosome may be utilized.

The microorganism or cell transformed with the replicable recombinant DNA of the present invention is, as mentioned above, selected from parent cells which remain untransformed by means of at least one phenotypical trait imparted by the recombinant DNA. A phenotypical trait may be imparted to the recombinant DNA by inserting at least one marker gene in the recombinant DNA. Alternatively, a marker gene inherent in the replicable expression vector may also be utilized. Examples of marker genes include a gene for drug resistance, for example, neomycin resistance, and a gene coding for dihydrofolate reductase (hereinafter referred to as "DHFR"). In this connection, it should be noted that there are various types of DHFR and, therefore, when a gene coding for a DHFR is used as a marker gene, the host cell to be used must be selected according to the types of DHFR encoded by the marker gene to be employed. For example, in the case where a gene coding for a wild type DHFR is used as a marker gene, it is preferred to use a host cell which is deficient in DHFR. Such a DHFR-deficient strain requires hypoxanthine, glycine and thymidine and, therefore, cannot grow in a medium containing no hypoxanthine, glycine and thymidine. However, when the DHFR-deficient strain is transformed with a recombinant DNA containing a gene coding for DHFR, the strain no longer requires hypoxanthine, glycine and thymidine and can grow even in a medium containing no hypoxanthine, glycine and thymidine. Therefore, transformed cells can easily be selected from the cells remaining untransformed, using as a criterion an auxotrophy with respect to hypoxanthine, glycine and thymidine.

On the other hand, in the case where a gene coding for a mutant DHFR which is poor in affinity to methotrexate (MTX) (the gene is hereinafter referred to as "MTX-resistant DHFR gene") is used as a marker gene, a host cell may not necessarily be deficient in DHFR as long as the cell contains a gene coding for a normal DHFR. The reason for this is as follows. The normal DHFR is inhibited by MTX and, therefore, a host cell containing a gene coding for a normal DHFR requires hypoxanthine, glycine and thymidine in the presence of MTX. However, when such a host is transformed with a recombinant DNA containing the MTX-resistant DHFR gene, the transformed cell no longer requires hypoxanthine, glycine and thymidine even in the presence of MTX. Therefore, the transformed cell can be selected from the cells remaining untransformed using as a criterion auxotrophy with respect to hypoxanthine, glycine and thymidine in the presence of MTX. In this connection, the majority of eukaryotic cells are sensitive to MTX and therefore, the MTX-resistant DHFR gene may be advantageously employed as a marker gene.

Further, yeasts such as *Saccharomyces cerevisiae* may also be used as a host for expressing the DNA of the present invention. For expressing the DNA of the present invention in the yeast, for example, a plasmid YRp7 and the like may be used as a replicable expression vector. The plasmid YRp7 contains a trp1 gene and the trp1 gene may be utilized as a marker gene.

Examples of promoters of the expression vector used for a yeast cell include promoters of genes for enzymes relating to the glycolytic pathway, such as 3-phosphoglycerate kinase or enolase, glyceraldehyde-3-phosphate dehydrogenase, hexokinase, pyruvate decarboxylase, phosphofructokinase, glucose-6-phosphate isomerase, and glucokinase, and genes for alcohol dehydrogenase 2, isocytochrome C, acid phosphatase, enzymes relating to nitrogen metabolism, glyceraldehyde-3-phosphate dehydrogenase, enzymes relating to maltose and lactose utilization, and the like. Among them, promoters of genes for alcohol dehydrogenase 2, isocytochrome C, acid phosphatase, enzymes relating to nitrogen metabolism, glyceraldehyde-3-phosphate dehydrogenase and enzymes relating to maltose and lactose utilization are more advantageous because the transcription by the action of these promoters can be controlled by changing the culturing conditions for a host.

With respect to an origin of replication, termination codon and other DNA sequences for controlling the transcription and translation in a yeast cell, any customary sequences may be used as long as they are suitable for a yeast cell.

The transformed microorganism or cell may be cultured in a customary nutrient medium according to a customary method to express the DNA coding for the peptide of the present invention and produce the peptide of the present invention. After the culturing, the peptide of the present invention may be isolated from the culture of the transformant by a customary method, for example, by means of column chromatography etc.

The thus obtained peptide may comprise at least one sugar residue of various types and lengths. As to whether or not the resultant peptide comprises a sugar residue is dependent on the type of host cell employed. Further, the type and the length of the sugar residue in the case where the peptide comprises a sugar residue are also dependent on the type of host cell employed.

Generally, it is known that a peptide translated from the initiation codon ATG may be processed to form a mature peptide when the peptide is secreted out of host cell. In the case of the peptide of the present invention also, the peptide may undergo such a processing. The position at which the peptide is processed varies according to the type of host and the culturing conditions. For example, in the case where the peptide of the present invention is produced in a transformant cell in an unprocessed immature form comprising the amino acid sequence of the formula (I) and a leader sequence of 18 amino acids as mentioned before as the N-terminal amino acid sequence, the immature peptide may be processed so that the leader sequence is cut off to form a mature peptide. However, as mentioned above, the processed portion of the immature peptide varies according to the type of host to be used and the culturing conditions for the host. Therefore, the above-mentioned processing does not always occur.

As mentioned above, the peptide of the present invention may be produced according to a process by recombinant DNA techniques. Alternatively, the peptide of the present invention may also be produced by organo-chemical synthesis according to a customary method, for example, using a commercially available automatic peptide synthesizer etc.

The peptide of the present invention has an activity to promote the activation of protein C by thrombin. Protein C is known as a protein which is dependent on vitamin K and plays an important role in the blood coagulation-fibrinolysis system, and is activated by the action of thrombin. It is known that in the living body, activated protein C inactivates activated factors V and VIII of the blood coagulation system coenzymes, and takes part in the production of plasminogen activator which has thrombolytic activity [Koji Suzuki, Igaku No Ayumi (History of Medicine), Vol. 125, p.901 (1983)]. The peptide of the present invention promotes the activation of protein C by thrombin, thereby enabling the production of a large quantity of activated protein C which exhibits anticoagulation and thrombolytic activities. Hence, the peptide of the present invention greatly contributes to in vivo anticoagulation and thrombolysis.

As mentioned above, the peptide of the present invention has anticoagulant, platelet aggregation-inhibiting and thrombolytic activities and, hence, can be used, for example, for the treatment and prevention of diseases, such as myocardial infarction, thrombosis, embolism, obstruction of peripheral blood vessels, arteriosclerosis obliterans, disseminated intravescular coagulation (DIC) syndrome, angina pectoris, transient ischemic attack and toxemia of pregnancy. For the treatment of the above-mentioned diseases the peptide of the present invention may be used in the form of a mixture with a pharmaceutically acceptable carrier. That is, an effective amount of the peptide of the present invention for treating or preventing the above-mentioned diseases may be mixed with an appropriate amount of a carrier to prepare a pharmaceutical composition which is suitable for effective administration to a patient. The peptide of the present invention may be used in the form of an injection etc. If the peptide is used in the form of an injection, there may be employed as an additive, a thickening agent such as sucrose, glycerol, methylcellulose or carboxymethylcellulose, a pH adjusting agent of various inorganic salts, and the like.

The dose of the peptide of the present invention per adult varies with the age, sex, weight, conditions, etc. of the patient. In general, however, the dose is about 0.1 to about 200 mg. The present peptide may be administered once a day or, if desired, several times a day.

PREFERRED EMBODIMENTS OF THE INVENTION

The present invention will be described in more detail with reference to Referential Examples and Examples, which should not be construed as limiting the scope of the present invention.

[REFERENTIAL EXAMPLES]

Referential Example 1

(Assay of the ability to promote the activation of protein C)

The ability of the peptide of the present invention to promote the activation of protein C was assayed according to a customary assay method for protein C in which use is made of a synthetic substrate, Boc-Leu-Ser-Thr-Arg-MCA (Boc and MCA are abbreviations for t-butoxycarbonyl group and 4-methylcoumaryl-7-amide, respectively.) [Y.Ohno et al, J. Biochem., Vol. 90, p.1387 (1981)]. Illustratively stated, to 5 μl of an aqueous solution containing 0.5 μM protein C and 80 nM thrombin were added 5 μl of an aqueous solution containing the peptide of the present invention (0 to 0.01 $A_{280}$/ml). To the mixture were added NaCl, $CaCl_2$, serum albumin and Tris-HCl buffer (pH7.4) so that the final concentrations of NaCl, $CaCl_2$, serum albumin and Tris-HCl buffer became 0.15 M, 2.5 mM, 1 mg/ml and 20 mM, respectively and that the final volume became 30 μl. The obtained mixture was kept at 37° C. for 15 min so that a reaction is allowed to proceed to thereby activate protein C. Then, 10 μl of an aqueous solution containing 2 μM antithrombin III and 10 μl of 10 U/ml heparin were added to the reaction mixture, followed by heating at 37° C. for 15 min so as to terminate the reaction. To the thus obtained mixture was added 250 μl of 20 mM Tris-HCl buffer (pH 7.4) containing 200 μM Boc-Leu-Ser-Thr-Arg-MCA, a synthetic substrate [manufactured by Peptide Institute, The Foundation, (Japan)], and allowed to stand at 37° C. for 10 min to advance the reaction. Thereafter, 0.5 ml of 20% aqueous acetic acid was added to the mixture to terminate the reaction. The concentration of liberated AMC (7-amino-4-methyl-coumarin) was measured by a spectrofluorometer Model RF-540 (manufactured by Shimadzu Corp., Japan) at an exciting wavelength of 380 nm and an emission wavelength of 440 nm. The obtained fluorescence intensity was compared with the fluorescence intensity of AMC having a known concentration to determine the amount of the liberated AMC. The activity is expressed in terms of the amount of AMC formed per minute. A value obtained by deducting the amount of AMC in the case where an aqueous solution not containing the peptide of the present invention is added, from the amount of AMC mentioned above, represents the activity of the sample to promote the activation of protein C by thrombin.

The protein C employed was purified from human blood plasma according to the method of Suzuki et al. [Suzuki et al., J. Biol. Chem., Vol. 258, p.1914 (1983)].

On the other hand, human thrombin was purified according to the method of Lundblad et al. [Lundblad et al, Biochem. Biophys. Res. Commun., Vol. 66, p. 482 (1975)].

Referential Example 2

(1): (Obtainment of a human lung cDNA library)

A bacteriophage λgt11 cDNA library which was prepared using poly(A)+ RNA derived from a human lung was purchased from Clontech Laboratories, Inc., 922 Industrial Ave., Palo Alto, Calif. 94303, U.S.A. (catalog No. HL1004).

(2): (Purification of a glycopeptide having the ability to promote the activation of protein C by thrombin)

A glycopeptide having the ability to promote the activation of protein C by thrombin was extracted from a human lung as follows. About 800 g of a human lung specimen provided by a public hospital was cut with scissors into pieces of 1 cm cube. To the thus obtained tissue pieces was added 500 ml of a physiological saline containing 1 mM DFP (diisopropyl fluorophosphate) which had been cooled to 4° C. The obtained mixture was homogenized using, as a Waring blender, Ace Homogenizer model AM-1 (manufactured by Nihonseiki Kaisha Ltd., Japan) at 4° C. for 5 min. After the homogenization, the mixture was cooled in ice. Then, the mixture was further homogenized at 4° C. for 5 min and cooled in ice for 5 min. The above-mentioned homogenizing and cooling operations were further repeated thrice. The thus obtained homogenate was subjected to centrifugation at 12,000 g at 4° C. for 30 min to separate the homogenate into a supernatant and pellets, and the pellets were collected. The collected pellets were suspended in 100 ml of 0.02 M Tris-HCl buffer (pH 7.5) containing 0.5% (v/v) Triton X-100, 0.25 M sucrose, 1 mM benzamidine hydrochloride and 0.5 mM $CaCl_2$, and subjected to homogenization 5 times at 4° C. for 5 min using the Waring blender to obtain a cell extract.

The obtained extract was subjected to centrifugation at 35,000 g at 10° C. for 60 minutes, and a supernatant was collected. A DIP-thrombin (diiso-propylphosphoro-thrombin), which had been prepared according to the method of N. L. Esmon et al. [J. Biol. Chem., Vol. 257, p.859 (1982)], was bonded to an agarose which had been treated with cyanogen bromide according to the method of P. Cuatrecasas [J. Biol. Chem., Vol. 245, p.3059 (1970)], thereby to prepare DIP-thrombin-agarose.

Then, the DIP-thrombin-agarose was packed in a 2.5 cmø×10 cm column to prepare a DIP-thrombin-agarose column. The column was equilibrated at room temperature with 0.02 M Tris-HCl buffer (pH 7.5) containing 0.1 M NaCl, 0.5 mM $CaCl_2$, 1 mM benzamidine hydrochloride and 0.5% (v/v) of Lubrol PX (manufactured by Nakarai Chemical Ltd., Japan). Subsequently, the above-mentioned supernatant of the extract was applied to the column. The column was washed with 0.02 M Tris-HCl buffer (pH 7.5) containing 0.3 M NaCl, 0.5 mM $CaCl_2$, 1 mM benzamidine hydrochloride and 0.5% (v/v) of Lubrol PX, followed by elution with 0.02 M Tris-HCl buffer (pH 7.5) containing 1 M NaCl, 0.1 mM EDTA, 1 mM benzamidine hydrochloride and 0.5% (v/v) Lubrol PX while collecting 2-ml fractions. With respect to each of the fractions obtained through the elution, the ability to promote the activation of protein C by thrombin was assayed according to the method as mentioned hereinbefore. At the same time, the absorbance ($A_{280}$) of each fraction was measured at a wavelength of 280 nm by means of a spectrophotometer model UV-240) manufactured by Shimadzu Corp. (Japan).

Fractions having the activity to promote the activation of protein C were recovered and pooled, and dialyzed against 0.02 M Tris-HCl buffer (pH 7.5) containing 0.1 M NaCl, 0.5 mM $CaCl_2$ and 0.05% (v/v) Lubrol PX. The dialysate thus obtained was subjected to the second DIP-thrombin-agarose column chromatography. That is, the dialysate was applied to a 1.5 cmø×10 cm column packed with a DIP-thrombin-agarose. The column was washed with 0.02 M Tris-HCl buffer (pH 7.5) containing 0.4 M NaCl, 0.5 mM $CaCl_2$ and 0.1% (v/v) Lubrol PX, and further washed with 0.02 M Tris-HCl buffer (pH 7.5) containing 0.4 M NaCl, 0.1 mM EDTA and 0.1% (v/v) Lubrol PX, followed by elution with 0.02 M Tris-HCl buffer (pH 7.5) containing 1 M NaCl, 0.5 mM EDTA and 0.1% (v/v) Lubrol PX. Fractions having the activity to promote the activation of protein C were recovered and pooled, and further dialyzed against 0.02 M Tris-HCl buffer (pH 7.5) containing 0.1 M NaCl and 0.05%(v/v) Lubrol PX. The dialysate thus obtained was subjected to the third DIP-thrombin-agarose column chromatography. The size of the column and the washing and elution conditions were the same as those in the second DIP-thrombin-agarose column chromatography. Through the elution, fractions each of 2 ml were collected. Fractions having the activity to promote the activation of protein C were recovered and pooled, and dialyzed against 0.02 M Tris-HCl buffer (pH 7.5) containing 0.1 M NaCl and 0.05%(v/v) Lubrol PX. Then, the dialysate was subjected to the fourth DIP-thrombin-agarose column chromatography using a 0.9 cmø×8 cm column. The column was washed with 0.02 M Tris-HCl buffer (pH 7.5) containing 0.35 M NaCl, 0.5 mM $CaCl_2$ and 0.1% (v/v) Lubrol PX, followed by elution with 0.02 M Tris-HCl buffer (pH 7.5) containing 1 M NaCl, 0.5 mM EDTA and 0.1% (v/v) Lubrol PX. Through the elution, fractions each of 1.9 ml were collected.

FIG. 1 shows the elution patterns of the fourth DIP-thrombin-agarose column chromatography. The fractions of Nos. 48 to 56 were recovered and pooled to obtain a solution.

The molecular extinction coefficient for general proteins, which is 10.0 ($E_{1\ cm}^{1\%}$·280 nm=10.0), was assigned to the purified peptide of the present invention. Based on this coefficient, the amount of the peptide thus purified in the pooled fractions was calculated from the absorbance for each of the fractions containing the purified peptide, and was found to be about 500 μg. Further, the purified peptide fractions obtained were subjected to SDS-polyacrylamide gel electrophoresis using a 5 to 10% polyacrylamide gel gradient at a voltage of 50 V for 2 hours, and the obtained band was observed after silver staining. As a result, only a single band was confirmed.

About 10 μg of the purified peptide was dialyzed against 50 mM Tris-HCl buffer (pH 7.5) containing 200 mM NaCl. Then, the dialysate was applied to a column packed with Con A-Sepharose (manufactured by Pharmacia Fine Chemicals AB, catalog No. 17-0440) (the amount of resin: about 1 ml) which had been equilibrated with the same buffer. The column was sufficiently washed with the same buffer. The purified protein was adsorbed on Con A-Sepharose.

Then, the same buffer as mentioned above except that 0.2 M NaCl and 0.5 M methyl-α-D-mannopyrano-side (manufactured by Sigma Chemical Company, U.S.A., catalog No. M-6882) was contained therein was passed through the column. As a result, the protein was found to be eluted. Accordingly, it was found that the protein contained a sugar, that is, it was a so-called glycopeptide.

(3): (Analysis of the amino acid sequence of a glycopeptide which promotes the activation of protein C by thrombin)

The amino acid sequence of the glycopeptide was analyzed as follows.

A purified glycoprotein containing solution was dialyzed against a 0.1%(v/v) aqueous solution of sodium lauryl sulfate (SDS) at room temperature for 16 hours to obtain a sample for the analysis of the amino acid sequence. Using an amino acid sequencing analyzer (Model 470 A) manufactured by Applied Biosystems Inc., (U.S.A.), Edman degradation was effected successively starting from the N-terminus according to the method of R. M. Hewick et al. [J. Biol. Chem., Vol. 256, p. 7990 (1981)]. The liberated phenylthiohydantoin amino acid was analyzed using an apparatus for high speed liquid chromatography (SP8100) manufactured by Spectra Physics (U.S.A.) and Solpacks ODS column manufactured by E.I. du Pont de Nemours and Company (U.S.A.) to determine the amino acid sequence. As a result, a part of the amino acid sequence of the glycopeptide was elucidated, that is, the 11 amino acids from the N-terminus thereof found to have the following amino acid sequence.

Ala-Pro-Ala-Glu-Pro-Gln-Pro-Gly-Gly-Ser-Gln (4): (Preparation of DNA probes coding for the N-terminal amino acid sequence)

DNA probes coding for the N-terminal amino acid sequence of the glycopeptide capable of promoting the activation of protein C by thrombin were synthesized using a DNA synthesizer model 380A manufactured by Applied Biosystems, U.S.A. and purified according to the description in the manufacturer's manual. One of the DNA probes synthesized was a 33 mer having the following base sequence coding for the N-terminal amino acid sequence: 5' CTGGG AGCCG CCGGG CTGGG GCTCG GCGGGGGC 3', which base sequence was determined based on the above-mentioned N-terminal amino acid sequence taking into consideration the frequency of bases in base sequences coding for amino acids with respect to human-derived gene [Nucleic Acid Res., Vol. 9, p. R43 (1981)]. The other DNA probes synthesized were 4 types of 23 mers having the following base sequences coding for the N-terminal amino acid sequence, in which base sequences containing deoxyino-sine (indicated by "I") were used instead of thymidylic acid in accordance with E. Otsuka et al., J. Biol. Chem., Vol. 260, p. 2605, 1985.

(1) 5' GCICC IGCIG AACCI CAGCC IGG 3'

(2) 5' GCICC IGCIG AGCCI CAACC IGG 3'

(3) 5' GCICC IGCIG AGCCI CAGCC IGG 3'

(4) 5' GCICC IGCIG AACCI CAACC IGG 3'

Each purified DNA was labeled with $^{32}$P using $T_4$ DNA kinase and $\gamma$-$^{32}$P-ATP, according to the method of Maniatis et al. described in an experimental textbook [Maniatis E. F., et al, Molecular Cloning, p.122, (1982)].

(5): (Antibody against a glycopeptide having the ability to promote the activation of protein C by thrombin)

A rabbit antibody against a glycopeptide capable of promoting the activation of protein C by thrombin was prepared according to the description of the textbook of L. Hudson et al., Practical Immunology, p.9, (1976), published by Blackwell Scientific Publications, using the glycopeptide derived from a human lung and having the ability to promote the activation of protein C by thrombin, which was purified as mentioned before.

The reactivity of the thus prepared antibody with a glycopeptide derived from a human lung and having the ability to promote the activation of protein C by thrombin was confirmed as follows. About 10 ng of glycopeptide purified according to the method described in Referential Example 2-(2) was spotted on a nitrocellulose filter and dried sufficiently. Then, the antibody was applied as a primary antibody to the nitrocellulose filter to allow the antibody to react with the glycopeptide on the filter. Further, a biotinylated anti-rabbit IgG prepared using a goat (manufactured by Zymed Laboratories Inc., U.S.A., catalog No. 62-1840) was applied as a secondary antibody to the filter to advance the reaction. Then, a streptavidin-biotinylated horseradish peroxidase complex (manufactured by Amersham Japan Limited, Japan, catalog No. RPN. 1051) was applied to the filter to stain it. Thus, a blackish brown spot appeared.

(6): (Collection and cultivation of endothelial cells of a human umbilical cord)

Endothelial cells of a human umbilical cord were collected from a vein obtained from a fresh human umbilical cord which was provided by a private hospital, and the cells were cultured according to the method of Mano et al. in which use is made of dispase II (manufactured by Godo Shusei Co., Ltd., Japan) [Y. Mano, et al, Experientia, Vol. 39, p.1144 (1983)].

Referential Example 3

(Preparation of a recombinant DNA)

(1): (Preparation of Poly(A)$^+$mRNA)

A poly(A)$^+$mRNA was prepared from human endothelial cells according to the method of Chirgwin et al. [Chirgwin, J. M. et al., Biochemistry, Vol. 18, p.5294 (1979)].

(2): (Screening from a human lung cDNA library)

E. coli Y1090 cells were infected with a cDNA library (manufactured by Clontech Laboratories Inc., U.S.A.) which was obtained by inserting cDNA's prepared from poly(A)$^+$ mRNA derived from a human lung into bacteriophages $\lambda$gt$_{11}$. The infection as conducted in accordance with a manual for the cDNA library. The infected E. coli Y 1090 cells were inoculated on an LB plate having a diameter of 15 cm so that about 100,000 plaques were formed per plate. The cells were cultured at 42° C. for 3.5 hours and, thereafter, a nitrocellulose filter (BA85 Membrane Filter, manufactured by Schleicher & Schuell, West Germany) which had been immersed in 10 mM IPTG (isopropyl-$\beta$-D-thiogalactopyranoside) and dried was placed on the plate, followed by incubation at 37° C. for 3.5 hours, so that peptides were expressed by the induction with IPTG and transferred to the nitrocellulose filter. In accordance with the above-mentioned manual, the antibody against a glycopeptide having the ability to promote the activation of protein C by thrombin, which antibody was prepared using a rabbit in Referential Example 2-(5), was applied as a primary antibody to the nitrocellulose filter to advance the reaction and, then, a biotinylated anti-rabbit IgG prepared using a goat (manufactured by Zymed Laboratories Inc., U.S.A., catalog No. 62-1840) was applied as a secondary antibody to the nitrocellulose filter to advance the reaction. Thereafter, the filter was stained with a streptavidin-biotinylated horseradish peroxidase complex (manufactured by Amersham Japan Limited, Japan, catalog No. RPN. 1051), and a positive clone was isolated. The cDNA fragment contained in a recombinant cDNA/$\lambda$gt$_{11}$ which was carried by the positive clone was designated TM13.

(3): (Hybridization with DNA probes coding for N-terminal amino acid sequence)

Whether or not the DNA fragment TM13 obtained in Referential Example 3 was hybridized with the N-terminal amino acid sequence-encoding DNA probes prepared in Referential Example 2-(4) was examined in accordance with an experimental textbook [Silhavy et al., Experiments With Gene Fusions, p.191, (1984), published by Cold Spring Harbor Laboratory]. As a result, it was found that TM13 did not hybridize any of the N-terminal amino acid sequence-encoding DNA probes.

(4): (Base sequence of TM13)

The base sequence of the DNA fragment TM13 contained in the clone which was obtained in Referential Example 3-(2) was determined according to the method of Sanger et al. [Sanger, F. et al., Proc. Natl. Acad. Sci., USA, Vol. 74, p.5463, (1977)]. The result is shown in FIG. 2.

(5): (Screening of a human lung cDNA library using the DNA fragment TM13 as a probe)

The DNA fragment TM13 was digested with restriction enzymes KpnI and PvuII to obtain a DNA fragment of about 440 bp, and the obtained DNA fragment was labeled with $^{32}$P by nick translation. Using the resultant DNA fragment as a probe, a human lung cDNA library was screened by plaque hybridization to obtain a positive clone. Illustratively stated, according to a customary method, the DNA clone TM13 was digested with KpnI and PvuII and subjected to polyacrylamide gel electrophoresis, followed by extraction and purification, to thereby obtain about 500 ng of a purified DNA fragment of about 440 bp. The thus obtained DNA fragment was labeled using $\alpha$-$^{32}$P-dCTP by the use of a nick translation kit (catalog No. N.5000) manufactured by Amersham Japan Limited (Japan) in accordance with a manual attached thereto.

Using the resulting $^{32}$P-labeled DNA fragment as a probe, the plaque hybridization of a human lung cDNA library was conducted in accordance with an experimental textbook [Maniatis et al., Molecular Cloning, p.320, 1982, published by Cold Spring Harbor Laboratory].

A positive clone was isolated and the structure of the recombinant contained in the positive clone was analyzed using various restriction enzymes. As a result, it was found that a DNA fragment of about 2400 bp was inserted in the obtained recombinant and that the DNA fragment comprised a base sequence coding for an amino acid sequence which was closer to the N-terminal of the above-mentioned peptide than that coded for by TM13. The DNA fragment was designated TM137.

(6): (Base sequence of DNA fragment TM137)

The base sequence of the DNA fragment TM137 was determined in substantially the same manner as described in Referential Example 3-(4). The results are shown in FIGS. 3(a)–(d).

The results showed that the DNA fragment TM137 did not comprise a base sequence coding for the N-terminal amino acid sequence described in Referential Example 2-(3).

(7): (Primer Extension)

3 types of synthetic DNA's were prepared in the same manner as described in Referential Example 2 -(4) based on the base sequence corresponding to a part of that of the DNA fragment TM13 obtained in Referential Example 3-(4), which part codes for an amino acid sequence on the N-terminal side. These DNA's were designated HTM131, HTM132 and HTM 133. In designing the synthetic DNA's, the base sequence on the side at which the mRNA prepared from the endothelial cells of a human umbilical cord is hybridized was utilized. The base sequences of those synthetic DNA's are as follows. The regions in the DNA fragments TM13 and TM137 which correspond to those DNA's are shown in FIGS. 2 and 3, respectively.

```
HTM131:
5' GACGCAGAGGTAGCTAGTTT 3'       ( 20 mer )
HTM132:
5' AACATCTGGCACCTG 3'            ( 15 mer )
HTM133:
5' GACAGGCAGTCTGGTTGCAA 3'       ( 20 mer )
```

Next, a DNA corresponding to the region on the further upstream side of the 5'-end of the DNA fragment TM137 was synthesized by a customary primer extension method using the HTM133 as a primer, and poly(A)$^+$mRNA prepared from the endothelial cells of a human umbilical cord according to the method described in Referential Example 3-(1).

That is, 20 $\mu$l of a solution containing about 27 ng/$\mu$l HTM133 was added to 5 $\mu$l of a solution containing about 1 $\mu$g/$\mu$l poly(A)$^+$mRNA. The resultant mixture was heated at 65° C. for 20 min and cooled to room temperature over about 1 hour. Then, a cDNA was synthesized using a cDNA-synthesizing system (manufactured by Amersham Japan Limited, Japan, catalog No. RPN1256) in accordance with a manual attached thereto except that the HTM133 was used in place of oligo(dT) primer contained in the cDNA-synthesizing system.

To both ends of the synthesized cDNA were added C tails in accordance with an experimental textbook [Maniatis et al., Molecular Cloning, p.241, 1982, published by Cold Spring Harbor Laboratory]. The resultant cDNA was mixed with the plasmid pBR322 (ATCC 37017) of which both ends have G tails added thereto. The resultant mixture was heated successively at 65° C. for 5 min and at 57° C. for 2 hours, and gradually cooled to room temperature. E. coli K12MC1061 (obtained from Beckman City of Hope Medical Institute, U.S.A.) was transformed with the reaction mixture. Illustratively stated, a colony of E. coli strain K12MC1061 was inoculated to LB medium and cultured so that the absorbance at 550 nm became 0.3. Then, 50 ml of the resultant culture was collected, washed with 25 ml of 10 mM 3-(N-morpholino) propane-sulfonic acid solution (MOPS) (pH7.0) containing 10 mM RbCl, and suspended in 0.1 M MOPS solution (pH6.5) containing 50 mM CaCl$_2$ and 10 mM RbCl.

The thus obtained suspension was cooled on ice for 30 min, followed by centrifugation. After centrifugation, a supernatant was removed and a cell pellet was suspended in 2.0 ml of 0.1 M MOPS(pH.6.5) containing 30 $\mu$l of DMSO, 50 mM CaCl$_2$ and 10 mM RbCl. Then, the resultant suspension was divided into 200 $\mu$l-suspensions. To each of the suspensions was added 10 $\mu$l of the above-mentioned plasmid DNA solution.

The resultant mixtures were cooled on ice for 30 min, followed by heat treatment at 44° C. for 60 sec to give heat shock to the mixture. Immediately after the heat treatment, 5 ml of an LB medium which had been heated to 37° C. in advance was added to each mixture. Then, the resultant solutions were incubated at 37° C. for 1 hour, followed by centrifugation to remove a supernatant and collect cell pellets. To each cell pellet was added an LB medium, followed by stirring to thereby obtain suspensions. The suspensions were separately spread on an LB agar plate containing 5 $\mu$g/ml tetracycline and incubated at 37° C. overnight.

The thus obtained cDNA bank was subjected to colony hybridization in substantially the same manner as described in Referential Example 3-(3) using as probes the HTM131 and HTM132 which were labeled with $^{32}$P at their 5'-ends according to the method described in Referential Example 2-(4).

About 70,000 transformants were screened by the colony hybridization, and 6 clones which reacted with both the probes HTM 131 and HTM 132 were obtained. From these 6 clones, plasmid DNA's (which are hereinafter referred to as "pTMP5") were prepared in accordance with an experimental textbook [Maniatis et al., Molecular Cloning, p.366, 1982, Cold Spring Harbor Laboratory] and cleaved by various restriction enzymes and the resultant DNA fragments were analyzed by electrophoresis. As a result, it was found that all the plasmid DNA's obtained from the 6 clones were the same and comprised a DNA fragment of about 900 bp and a vector. These DNA fragments were designated TMP5.

(8): (Hybridization of the DNA fragment TMP5 with DNA probes encoding the N-terminal amino acid sequence)

Whether or not the DNA fragment TMP5 hybridized DNA probes encoding the N-terminal amino acid sequence was examined in substantially the same manner as described in Referential Example 3-(3).

As a result, it was found that the DNA fragment TMP5 did not hybridize any of the N-terminal DNA probes, that is, did not code for the N-terminal amino acid sequence region.

(9): (Base sequence of the the DNA fragment TMP5)

The base sequence of the the DNA fragment TMP5 was determined according to the same method as described in Referential Example 3-(4). The results are shown in FIGS. 4 (a)–(b).

(10): (Second primer extension)

Three 20mer synthetic DNA's HTM134, HTM135 and HTM136 were prepared on the basis of the base sequence of the DNA fragment TMP5 in substantially the same manner as described in Referential Example 3-(7). The locations in the DNA fragment TMP5 which correspond to those of the above-mentioned synthetic DNA's are shown in FIG. 4.

The primer extension was carried out in substantially the same manner as described in Referential Example 3-(7) using HTM136 as a primer, and HTM134 and HTM135 as probes. From about 50,000 transformants, one type of transformant which hybridized HTM134 and HTM135 was obtained. A DNA fragment contained in a recombinant which the transformant carried was designated TMP26.

(11): (Hybridization of the DNA fragment TMP26 with the DNA probe encoding the N-terminal amino acid sequence)

Whether or not the DNA fragment TMP26 hybridized the DNA probe encoding the N-terminal amino acid sequence was examined in the same manner as described in Referential Example 3-(3).

As a result, it was found that the DNA fragment TMP26 hybridized the 33mer DNA probe encoding the N-terminal amino acid sequence and a mixed probe of 4 kinds of 25mer probes, which probes were synthesized in Referential Example 2-(4). That is, it was found that the DNA fragment TMP26 encoded the N-terminal amino acid sequence region.

(12): (Base sequence of the DNA fragment TMP26)

The base sequence of the DNA fragment TMP26 was determined according to the same method as described in Referential Example 3-(4). The base sequence of about 540 bp from the carboxyl terminus of the DNA fragment TMP26 is shown in FIG. 5.

(13): (Ligation of the DNA fragments TMP26, TMP5 and TM137)

As described above, four DNA fragments (TM13, TM137, TMP5 and TMP26) were obtained and subjected to determination of their base sequences in Referential Example 3-(1) to (12). Some of the four DNA fragments partially correspond to some other DNA fragments with respect to base sequence. In FIG. 6, such corresponding relationships are illustrated, with a brief restriction enzyme cleavage map of each DNA fragment. As shown in FIG. 6, when an open reading frame is presumed to begin from the first ATG which is present upstream in the base sequence of the DNA fragment TMP26 which includes the base sequence coding for the N-terminal amino acid sequence, then such an open reading frame should comprise 1725 bp, which contain sequences that partially correspond to the respective sequences of the DNA fragments TMP26, TMP5 and TM137. In order to obtain a DNA fragment having such an open reading frame, the DNA fragments TMP26, TMP5 and TM137 were ligated according to a customary method as follows.

(13-1) (Ligation of the DNA fragments TM137 and TMP5)

First, the DNA fragment TM137 inserted at an EcoRI site of $\lambda gt_{11}$ was isolated and inserted at an EcoRI site of a plasmid pUC18 (manufactured by Pharmacia Fine Chemicals AB, Sweden, catalog No. 27-4949-01) to thereby obtain a plasmid pUC18TM137.

Second, the plasmid pUC18TM137 was digested with restriction enzymes HincII and EcoRI. The resultant DNA fragments were separated by 4% (w/v) polyacrylamide gel electrophoresis and then a DNA fragment of about 2,300 bp was recovered using an extraction apparatus for electrophoresis (MAX-YIELD®, manufactured by ATTO Corporation, Japan), followed by ethanol precipitation to purify the DNA fragment.

On the other hand, a plasmid pTMP5 prepared by inserting the TMP5 obtained in Referential Example 3-(7) in a plasmid pBR322 was completely digested with DdeI, and the ends of the cleaved product were converted to blunt ends by means of E. coli DNA polymerase (Klenow PolI fragment), and a DNA fragment of about 800 bp was recovered. Then, this DNA fragment was inserted at an SmaI site of a plasmid pUC18 to thereby obtain a plasmid pUC18TMP5. Then, the plasmid pUC18TMP5 was completely digested with restriction enzymes BamHI and HincII to thereby obtain a BamHI-HincII fragment of about 600 bp.

The DNA fragment of about 2,300 bp prepared from the plasmid pUC18TM137 and the DNA fragment of about 600 bp prepared from the plasmid pUC18TMP5 were inserted in a vector prepared by digesting a plasmid pUC18 with BamHI and EcoRI, to thereby obtain a plasmid pUC18TMJ1.

The process is shown in FIG. 7.

(13-2) (Ligation of the DNA fragment TMJ1 and TMP26)

The plasmid pUC18TMJI was completely digested with restriction enzymes DdeI, KpnI and BamHI, and fragments of about 950 bp and of about 1500 bp were recovered.

On the other hand, the DNA fragment TMP26 was inserted at a PstI site of a plasmid pUC13 (manufactured by Pharmacia Fine Chemicals AB, Sweden, catalog No. 27-4954-01), which site was cleaved by a restriction enzyme PstI, to thereby obtain a plasmid pUC13TMP26. This plasmid was completely digested with BbeI and the ends of the cleaved product were converted to blunt ends by means of $T_4$ DNA polymerase. Further, the cleaved product was digested with restriction enzyme BglII to thereby obtain a DNA fragment of about 170 bp.

Further separately, the plasmid pUC13TMP26 was completely digested with BglII and DdeI to obtain a DNA fragment of about 280 bp.

Then, the above-mentioned DNA fragments of about 170 bp, of about 280 bp and of about 950 bp were ligated to one another using $T_4$ DNA ligase, digested with a restriction enzyme KpnI and subjected to 1.3% low-melting point agarose gel electrophoresis at 50 V at 4° C. for 2 hours to isolate and purify a DNA fragment of about 1400 bp.

Furthermore, a plasmid pUC18 was completely digested with SphI. The ends of the cleaved product were converted to blunt ends by means of E. coli DNA polymerase. Then, the product was completely digested with BamHI to prepare a vector. The above-obtained DNA fragments of about 1,400 bp and of about 1,500 bp were inserted in the vector using $T_4$ DNA ligase to thereby obtain a plasmid pUC18TMJ2.

The process is shown in FIG. 8.

Referential Example 4 (Screening of a human chromosome for obtaining a desired gene)

The screening of a human chromosome library for obtaining a desired gene was carried out as follows.

The human chromosome library inserted in a vector EMBL-3 derived from λphage was purchased from Clontech Laboratories, Inc., 922 Industrial Ave. Palo Alto, Calif. 94303 U.S.A. (catalog No. HL1006). The screening of the library was carried out in substantially the same manner as described in Referential Example 3-(5) using as a probe the DNA fragment TM13 obtained in Referential Example 3-(2), to thereby obtain one type of chromosomal clone containing an insert of about 20,000 bp. This chromosomal clone was completely digested with a restriction enzyme BamHI and subjected to 1.0% agarose gel electrophoresis and then subjected to Southern blot hybridization using the same probe in accordance with an experimental textbook [Maniatis et al., Molecular Cloning, p. 382, 1982, Cold Spring Harbor Laboratory].

As a result, a strong positive band was observed at a position of a DNA fragment of about 4,000 bp. The fragment was isolated according to a customary method and subjected to subcloning at a BamHI site of a plasmid pUC18. The results of the base sequence determination of the DNA fragment of about 4,000 bp showed that the base sequence was completely coincident with that of the the DNA fragment inserted in the plasmid pUC18TMJ2 prepared in Referential Example 3-(13-2).

[EXAMPLES]

Example 1

(Construction of plasmids pSV2TMJ2, pSV2TMD1, pSV2TMD2, pSV2TMD4 and pSV2TMD5)

(1) Construction of a plasmid pSV2TMJ2

A plasmid pSV2-dhfr (ATCC 37146) was completely digested with restriction enzymes HindIII and BglII to obtain a vector having an early promoter and transcription terminator of SV40. On the other hand, the plasmid pUC18TMJ2 prepared in Referential Example 2-(13-2) was partially digested with a restriction enzyme HindIII and, then, completely digested with a restriction enzyme BamHI to obtain a DNA fragment of about 2900 bp. The DNA fragment was designated TMJ2. Then, the DNA fragment of about 2900 bp and the above-obtained vector were ligated to each other by means of $T_4$ DNA ligase to obtain a plasmid pSV2TMJ2. The procedure of the construction of the plasmid pSV2TMJ2 is illustrated in FIG. 9.

The thus obtained plasmid pSV2TMJ2 is on deposit at the American Type Culture Collection (ATCC) under the Budapest Treaty and has been given accession No. 67283.

(2) Construction of a plasmid pSV2TMD1

(a) Preparation of a DNA fragment TMD1

The plasmid pSV2TMJ2 obtained in the above step (1) was completely digested with a restriction enzyme NcoI to cleave the plasmid. Both ends of the cleaved plasmid were treated with E. coli DNA polymerase to make them blunt. Then, the cleaved plasmid was completely digested with a restriction enzyme HindIII to obtain a DNA fragment of about 1900 bp. The thus obtained DNA fragment was designated TMJ3. On the other hand, a phage M-13mp19 (manufactured by Takara Shuzo Co., Ltd., Japan, catalog No. 3119) was digested with restriction enzymes HindIII and HincII to obtain a vector. The DNA fragment TMD3 was inserted in the above-obtained vector to obtain a recombinant M-13mp19TMJ3.

Separately, a DNA probe for deletion (hereinafter referred to as "deleter") having the following base sequence was organo-chemically synthesized:

5'-GGAGGCCGCTCAGCCCGAATGCACG-3' (25mer).

The synthesized deleter was designated TMD.

Then, part of the above-obtained recombinant phage M-13mp19TMJ3, which had a length of 177 bases, was deleted by a technique of site-directed mutagenesis using the thus obtained deleter TMD in accordance with the method described in Method in Enzymology, 100, 468 (1983), Academic Press. Illustratively stated, 25 pmol of the deleter TMD and 10 pmol of M13 primer M3 (a universal primer manufactured by Takara Shuzo Co., Ltd., Japan, catalog No. 3831) were phosphorylated at their 5'-ends by means of $T_4$ kinase. To the phosphorylated deleter and universal primer was added 0.5 pmol of a single-stranded DNA of the recombinant phage M-13mp19TMJ3. The resultant mixture was heated at 95° C. for 5 minutes and then cooled to room temperature. Then, 5 units of E. coli DNA polymerase I (Klenow fragment) and 10 units of $T_4$ DNA ligase were added to the mixture and the mixture was incubated at 37° C. for 30 min to form a recombinant plasmid in the mixture. The thus obtained mixture was added to a culture of E. coli JM150 (manufactured by Pharmacia Fine Chemicals AB, Sweden, catalog No. 27-1550) to transfect the E. coli with the recombinant plasmid. The E. coli was cultured on an agar plate at 37° C. overnight to thereby form plaques on the agar plate. The plaques were transplanted on a nitrocellulose filter and heated at 80° C. for 2 hours. Then, the nitrocellulose filter was subjected to prehybridization at 55° C. for 2 hours in a solution containing 6× SET [0.9 M NaCl, 180 mM Tris buffer (pH8.0), 6 mM EDTA], 5× Denharts' [0.1%(w/v) Ficoll, 0.1%(w/v) polyvinyl pyrrolidone and 0.1%(w/v) bovine serum albumin (BSA)], 0.1% SDS and 100 μg/ml denatured DNA of a salmon sperm. Subsequently, the resultant nitrocellulose filter was subjected to hybridization at 55° C. for 2 hours using a $^{32}$P-labeled TMD instead of the denatured DNA of a salmon sperm contained in the above-mentioned solution. Then, the nitrocellulose filter was washed with 6× SSC solution (an aqueous solution containing 0.9 M NaCl and 0.09 M trisodium citrate) twice at room temperature each for 5 min. Further, the filter was washed with the same solution successively at 55° C., 65° C. and 75° C. The above washing was conducted twice each for 5 min at the respective temperature. Then, an X-ray film XAR-5 (manufactured by Eastman Kodak Company, U.S.A.) was contacted with the resultant nitrocellulose filter at −80° C. overnight to expose the X-ray film. As a result, it was found that several tens of strongly exposed black spots were observed on the X-ray film. Each of the spots corresponded to respective clones which had been transfected with the recombinant plasmid. Six clones were selected from the obtained clones and the recombinant plasmid of each of the selected clones was isolated and analyzed with respect to its restriction sites and base sequence. The recombinant plasmids of the clones were found to be identical with respect to their restriction sites and base sequence. The thus obtained recombinant plasmid was designated M13-TMD1. Further, the recombinant plasmid M13-TMD1 was found to contain a DNA fragment having a base sequence including an initiation codon (ATG) and, downstream thereof, a base sequence coding for a peptide of the present invention comprised of 498 amino acids. The DNA fragment contained in the recombinant plasmid M13-TMD1 was designated TMD1. In FIG. 10, there is illustrated the recombinant plasmid M-13mp19TMJ3 with which the deleter TMD is hybridized, and of which the DNA region corresponding to the DNA fragment TMJ3 is partly deleted.

(b) Construction of a plasmid pSV2TMD1

The recombinant plasmid M-13TMD1 obtained in Example 1-(2)-(a) was completely digested with restriction enzymes HindIII and BamHI to isolate the DNA fragment TMD1 of about 1900 bp. On the other hand, the plasmid pSV2-dhfr (ATCC 37146) was completely digested with restriction enzymes HindIII and BglII to obtain a vector. The DNA fragment and the vector were ligated with each other by means of $T_4$ DNA ligase to obtain a plasmid pSV2TMD1.

(3) Construction of a plasmid pSV2TMD2

(a) Preparation of a DNA fragment TMD2

Substantially the same procedures as in Example 1-(2)-(a) were repeated except that a deleter $TMd_2$ having the following base sequence:

5'-CTCCACGCTGCAGGGGAACCCCAGG-3' (25mer)

was used as a DNA probe for deletion instead of the deleter TMD, to thereby obtain a recombinant plasmid M13-TMD2 having inserted therein a DNA fragment designated TMD2. The DNA fragment TMD2 had such a structure that a DNA of 678 bp is deleted from the 5'-end of the DNA fragment TMD1 obtained in Example 1-(2)-(a). The DNA fragment TMD2 had a base sequence including an initiation codon (ATG) and, downstream thereof, a base sequence coding for a peptide of the present invention comprised of 272 amino acids. In FIG. 11, there is illustrated the recombinant plasmid M13-TMD1 with which the deleter $TMd_2$ is hybridized, and of which the DNA region corresponding to the DNA fragment TMD1 is partly deleted.

(b) Construction of a plasmid pSV2TMD2

The recombinant plasmid M13-TMD2 obtained in Example 1-(3)-(a) was completely digested with restriction enzymes HindIII and BamHI to isolate the DNA fragment TMD2 of about 1200 bp. On the other hand, the plasmid pSV2-dhfr (ATCC 37146) was completely digested with restriction enzymes HindIII and BglII to obtain a vector. The DNA fragment and the vector were ligated with each other by means of $T_4$ DNA ligase to obtain a plasmid pSV2TMD2.

(4) Construction of a plasmid pSV2TMD4

(a) Preparation of a DNA fragment TMD3

The plasmid pSV2TMJ2 obtained in the above step (1) was completely digested with a restriction enzyme NcoI to cleave the plasmid. Both ends of the cleaved plasmid were treated with *E. coli* DNA polymerase to make them blunt. Then, the cleaved plasmid was completely digested with a restriction enzyme HindIII to obtain a DNA fragment of about 1900 bp. The thus obtained DNA fragment was designated TMJ3. On the other hand, a phage M-13mp19 (manufactured by Takara Shuzo Co., Ltd., Japan, catalog No. 3119) was digested with restriction enzymes HindIII and HincII to obtain a vector. The DNA fragment TMJ3 was inserted in the above-obtained vector to obtain a recombinant plasmid M-13mp19TMJ3.

Separately, a deleter having the following base sequence was organo-chemically synthesized:

5'-GGAGGCCGCTCAACAGTCGGTGCCA-3' (25mer).

The synthesized deleter was designated $TMd_3$.

Then, part of the above-obtained recombinant plasmid M-13mp19TMJ3, which had a length of 285 bp, was deleted by a technique of site-directed mutagenesis using the deleter $TMd_3$ in accordance with the method described in Method in Enzymology, 100, 468 (1983), Academic Press. Illustratively stated, 25 pmol of the deleter TMD and 10 pmol of M13 primer M3 (a universal primer manufactured by Takara Shuzo Co., Ltd., Japan, catalog No. 3831) were phosphorylated at their 5'-ends by means of $T_4$ kinase. To the phosphorylated deleter and universal primer was added 0.5 pmol of a single-stranded DNA of the recombinant plasmid M-13mp19TMJ3. The resultant mixture was heated at 95° C. for 5 minutes and then, cooled to room temperature. Then, 5 units of *E. coli* DNA polymerase I (Klenow fragment) and 10 units of $T_4$ DNA ligase were added to the mixture and the resultant mixture was incubated at 37° C. for 30 min to form a recombinant plasmid in the mixture. The thus obtained mixture was added to a culture of *E. coli* JM105 (manufactured by Pharmacia Fine Chemicals AB, Sweden, catalog No. 27-1550) to transfect the *E. coli* with the recombinant plasmid. The *E. coli* was cultured on an agar plate at 37° C. overnight to thereby form plaques on the agar plate. The plaques were transplanted on a nitrocellulose filter and heated at 80° C. for 2 hours. Then, the nitrocellulose filter was subjected to prehybridization at 55° C. for 2 hours in a solution containing 6× SET [0.9 M NaCl, 180 mM Tris buffer (pH8.0), 6 mM EDTA], 5× Denharts' [0.1%(w/v) Ficoll, 0.1%(w/v) polyvinyl pyrrolidone and 0.1%(w/v) bovine serum albumin (BSA)], 0.1%(w/v) SDS and 100 μg/ml denatured DNA of a salmon sperm. Subsequently, the resultant nitrocellulose filter was subjected to hybridization at 55° C. for 2 hours using a $^{32}$P-labeled deleter $TMd_3$ instead of the denatured DNA of a salmon sperm contained in the above-mentioned solution. Then, the nitrocellulose filter was washed with 6× SSC solution (an aqueous solution containing 0.9 M NaCl and 0.09 M trisodium citrate) twice at room temperature each for 5 min. Further, the filter was washed with the same solution successively at 55° C., 65° C. and 75° C. The above washing was conducted twice each for 5 min at the respective temperature. Then, an X-ray film XAR-5 (manufactured by Eastman Kodak Company, U.S.A.) was contacted with the resultant nitrocellulose filter at −80° C. overnight to expose the X-ray film. As a result, it was found that several tens of strongly exposed black spots were observed on the X-ray film. Each of the spots corresponded to respective clones which had been transfected with the recombinant plasmid. Six clones were selected from the obtained clones and the recombinant plasmid of each of the selected clones was isolated and analyzed with respect to its restriction sites and base sequence. The recombinant plasmids of the clones were found to be identical with respect to their restriction sites and base sequence. The thus obtained recombinant plasmid was designated M13-TMD3. Further, the recombinant plasmid M13-TMD3 was found to contain a DNA fragment having a base sequence including an initiation codon (ATG) and, downstream thereof, a base sequence coding for a peptide of the present invention comprised of 426 amino acids. The DNA fragment contained in the recombinant phage M13-TMD3 was designated TMD3. In FIG. 12, there is illustrated the recombinant plasmid M-13mp19TMJ3 with which the deleter $TMd_3$ is hybridized, and of which the DNA region corresponding to the DNA fragment TMJ3 is partly deleted.

(b) Preparation of a DNA fragment TMD4

Part of the above-obtained recombinant plasmid M13-TMD3 was deleted by a technique of site-directed mutagenesis in substantially the same manner as in Example 1-4-(a) except that the deleter $TMd_2$ obtained in Example 1-(3)-(a) was used instead of the deleter $TMd_3$ to thereby obtain a recombinant plasmid M13-TMD4 containing a DNA fragment designated TMD4. The DNA fragment TMD4 had such a structure that the 5'-end base sequence comprised of 678 bp is deleted from the DNA fragment TMD3 obtained in Example 1-4-(a). The DNA fragment TMD4 had a base sequence including an initiation codon (ATG) and, downstream thereof, a base sequence coding for a peptide of the present invention comprised of 236 amino acids. In FIG. 13, there is illustrated the recombinant plasmid M13-TMD3 with which the deleter $TMd_2$ is hybridized, and of which the DNA region corresponding to the DNA fragment TMD3 is partly deleted.

(c) Construction of a plasmid pSV2TMD4

The recombinant plasmid M13-TMD4 obtained in Example 1-(4)-(b) was completely digested with restriction enzymes HindIII and BamHI to isolate the DNA fragment TMD4 of about 1100 bp. On the other hand, the plasmid pSV2-dhfr (ATCC 37146) was completely digested with restriction enzymes HindIII and BglII to obtain a vector. The DNA fragment and the vector were ligated with each other by means of $T_4$ DNA ligase to obtain a plasmid pSV2TMD4.

(5) Construction of a plasmid pSV2TMD5

(a) Preparation of a DNA fragment TMD5

Substantially the same procedures as in Example 1-(4)-(b) were repeated except that a deleter $TMd_4$ having the following base sequence:

5'-CACGGGCTCCACGGGGAACCCCAGG-3' (25mer)

was used as a DNA probe for deletion instead of the deleter $TMD_4$, to thereby obtain a recombinant plasmid M13-TMD5 containing a DNA fragment designated TMD5. The DNA fragment TMD5 had such a structure that a DNA of 1032 bp is deleted from the 5'-end of the DNA fragment TMD3 obtained in Example 1-(4)-(a). The DNA fragment TMD5 had a base sequence including an initiation codon (ATG) and, downstream thereof, a base sequence coding for a peptide of the present invention comprised of 118 amino acids. In FIG. 14, there is illustrated the recombinant plasmid M13-TMD3 with which the deleter $TMd_4$ is hybridized, and of which the DNA region corresponding to the DNA fragment TMD3 is partly deleted.

(b) Construction of a plasmid pSV2TMD5

The recombinant phage M13-TMD5 obtained in Example 1-(5)-(a) was completely digested with restriction enzymes HindIII and BamHI to isolate the DNA fragment TMD5 of about 740 bp. On the other hand, the plasmid pSV2-dhfr (ATCC 37146) was completely digested with restriction enzymes HindIII and BglII to obtain a vector. The DNA fragment and the vector were ligated with each other by means of $T_4$ DNA ligase to obtain a plasmid pSV2TMD5.

Example 2

(Transformation of cells of a cell line COS-1 with plasmid pSV2TMD5)

A cell line COS-1 (ATCC CRL1650) was cultured in a Dulbecco's minimal essential medium (hereinafter referred to as "MEM")(manufactured by Flow Laboratories Inc., U.S.A., catalog No. 10-331) containing 10%(v/v) fetal calf serum (hereinafter referred to as "FCS"), which was contained in a culture vessel, at 37° C. in a 5% $CO_2$ gas incubator. When the culture achieved a logarithmic growth phase, the cells which had grown adhering to the culture vessel were peeled off from the culture vessel using 0.1% aqueous trypsin solution and 0.02% aqueous EDTA solution. The peeled-off cells were suspended in Hanks' balanced salt solution (manufactured by Flow Laboratories Inc., U.S.A., catalog No. 17-101-22) so that the cell concentration became about $1 \times 10^7$ cells/ml to thereby obtain a cell suspension.

The plasmid pSV2TMD5 obtained in Example 1-(5) was suspended in 1 mM Tris-HCl buffer (pH 8.0) at a concentration of about 2 µg/µl. 5 µl of the resultant plasmid suspension containing about 10 µg of the plasmid pSV2TMD5 was put in an Eppendorf type test tube having a capacity of 1.5 ml. Then, about 200 µl of the above-obtained cell suspension of the cell line COS-1 was charged in the test tube. The tube was allowed to stand at 0° C. for 10 min. The resulting suspension in the test tube was transferred to a cuvette of a high voltage fusion processor model FPH1001 manufactured by D.E.P. SYSTEM Inc., Co., U.S.A. and an electric current was applied to the suspension at 1.2 kV twice each for 40 µsec. Thereafter, the suspension was returned to the test tube and allowed to stand at 0° C. for 5 min. The resultant suspension was transferred to a plate for tissue culture having a diameter of 10 cm using 10 ml of a Dulbecco's MEM containing 10%(v/v) FCS as follows. An aliquot of the Dulbecco's MEM containing 10%(v/v) FCS was added to the suspension and the mixture was transferred to a plate for tissue culture. Then, the test tube was washed with the remaining Dulbecco's MEM several times and the washings were added to the plate. Then, the plate was incubated at 37° C. for 24 hours under an atmosphere of 5% $CO_2$.

(Confirmation of ability to promote the activation of protein C by thrombin)

After completion of the incubation, the medium in the plate was replaced by Dulbecco's MEM containing no FCS and the plate was incubated at 37° C. for 48 hours. After the incubation, 5 ml of the supernatant of the culture was taken out as a sample and subjected to assay for the ability to promote the activation of protein C by thrombin according to the method as described in Referential Example 1.

Further, a plate of the cells in the plate for tissue culture having a diameter of 10 cm was collected by scraping using a Cell Scraper manufactured by Coaster, U.S.A. (catalog No. 3010), followed by centrifugation at 800 rpm for 10 min. Using the resultant cell pellet as a sample, the ability to promote the activation of protein C was assayed in the manner as described in Referential Example 1. As a control, the supernatant and cell pellet of the culture of COS-1 cell which was transformed with a plasmid pSV2-dhfr were used as a sample.

The results are shown in Table 1. In the table, the values of the absorbance were those obtained by calculating the absorbance of each sample in terms of the value for one plate for tissue culture.

TABLE 1

| Plasmid | Sample | Absorbance |
|---|---|---|
| pSV2TMD5 (Present invention) | Supernatant of the culture | 4300 |
|  | Cell pellet | 6.9 |
| pSV2-dhfr (Control) | Supernatant of the culture | not detected |
|  | Cell pellet | not detected |

Example 3

(Transformation of COS-1 cell with plasmid pSV2TMD4 and assay of the ability of the peptide produced by the transformed cell to promote the activation of protein C by thrombin)

Substantially the same procedures as in Example 2 except that plasmid pSV2TMD4 was used were repeated to thereby assay the ability of the peptide to promote the activation of protein C by thrombin, which peptide was produced by cells transformed with plasmid pSV2TMD4. The results are shown in Table 2. In the table, the values of the absorbance were those obtained by calculating the absorbance of each sample in terms of the value for one plate for tissue culture.

TABLE 2

| Plasmid | Sample | Absorbance |
| --- | --- | --- |
| pSV2TMD4 (Present invention) | Supernatant of the culture | 4200 |
| | Cell pellet | 6.8 |
| pSV2-dhfr (Control) | Supernatant of the culture | not detected |
| | Cell pellet | not detected |

Example 4

(Transformation of COS-1 cell with plasmid pSV2TMD2 and assay of the ability of the peptide produced by the transformed cell to promote the activation of protein C by thrombin)

Substantially the same procedures as in Example 2 except that plasmid pSV2TMD2 was used were repeated to thereby assay the ability of the peptide to promote the activation of protein C by thrombin, which peptide was produced by cells transformed with plasmid pSV2TMD2. The results are shown in Table 3. In the table, the values of the absorbance were those obtained by calculating the absorbance of each sample in terms of the value for one plate for tissue culture.

TABLE 3

| Plasmid | Sample | Absorbance |
| --- | --- | --- |
| pSV2TMD2 (Present invention) | Supernatant of the culture | 4000 |
| | Cell pellet | 7.0 |
| pSV2-dhfr (Control) | Supernatant of the culture | not detected |
| | Cell pellet | not detected |

Example 5

(Transformation of COS-1 cell with plasmid pSV2TMD1 and assay of the ability of the peptide produced by the transformed cell to promote the activation of protein C by thrombin)

Substantially the same procedures as in Example 2 except that plasmid pSV2TMD1 was used were repeated to thereby assay the ability of the peptide to promote the activation of protein C by thrombin, which peptide was produced by cells transformed with plasmid pSV2TMD1. The results are shown in Table 4. In the table, the values of the absorbance were those obtained by calculating the absorbance of each sample in terms of the value for one plate for tissue culture.

TABLE 4

| Plasmid | Sample | | Absorbance |
| --- | --- | --- | --- |
| pSV2TMD1 (Present invention) | Supernatant of the culture | (FCS+) | 600 |
| | | (FCS−) | 1200 |

TABLE 4-continued

| Plasmid | Sample | | Absorbance |
| --- | --- | --- | --- |
| | Cell pellet | (FCS+) | 1.8 |
| | | (FCS−) | 3.6 |
| pSV2-dhfr (Control) | Supernatant of the culture | (FCS+) | not detected |
| | | (FCS−) | not detected |
| | Cell pellet | (FCS+) | not detected |
| | | (FCS−) | not detected |

Example 6

(Transformation of COS-1 cell with plasmid pSV2TMJ2 and assay of the ability of the peptide produced by the transformed cell to promote the activation of protein C by thrombin)

Substantially the same procedures as in Example 2 except that plasmid pSV2TMJ2 was used were repeated to thereby assay the ability of the peptide to promote the activation of protein C by thrombin, which peptide was produced by cells transformed with plasmid pSV2TMJ2. As a result, it was found that the cell pellet sample had a high activity of promoting the activation of protein C so that the amount of the formed protein C was as high as about 300 ng. On the other hand, in the case of cells transformed with plasmid pSV2-dhfr which was used as a control, the activity was not detected.

Example 7

(Transformation of CHO cell with plasmid pSV2TMD5 and expression in the transformed cell)

About 4 μg of plasmid pSV2-neo(ATCC 37150) and about 20 μg of plasmid pSV2TMD5 prepared in Example 1-(5) were mixed with each other, followed by precipitation with ethanol. The precipitate was air-dried and dissolved in 450 μl of a TE solution (pH7.9, 1 mM Tris-HCl buffer, 0.1 mM EDTA). To the solution was added 500 μl of a 2× HBS (50 mM HEPES, 280 mM NaCl, 1.5 mM $Na_2HPO_4$, pH 7.12). To the mixture was dropwise added 50 μl of 2.5 M $CaCl_2$, and the resultant mixture was kept at room temperature for 10 min. On the other hand, cells of CHO-KI strain (ATCC CCLD 61) were inoculated onto a plate for tissue culture which had a diameter of 6 cm and contained Ham's F-12 medium (manufactured by Flow Laboratories, Inc., U.S.A., catalog No. 10-421-20) containing 10% (v/v) FCS and 1 v/v % penicillin-streptomycin (manufactured by Flow Laboratories, Inc., U.S.A., catalog No. 16-700-49) so that the amount of cells became about $5×10^5$ per plate. The inoculated cells were incubated overnight. Then, the medium was changed with a fresh medium of the same kind, followed by incubation for 3 hours. Over the resultant CHO-KI cells, the above-mentioned plasmid DNA solution to which the $CaCl_2$ solution had been dropwise added was layered and the incubation was conducted at 37° C. for about 8 hours. Then, the plate was washed twice with 5 ml of PBS(−) (manufactured by Flow Laboratories, Inc., U.S.A., catalog No. 28-103-05) and further washed with 5 ml of the above-mentioned medium, and a fresh medium of the same type was added to the plate, followed by culturing for about 16 hours.

The resultant cells adhering to the plate were peeled off and transplanted onto 4 plates for tissue culture having a diameter of 10 cm, followed by incubation. 24 hours later, the medium was changed with a selective medium. The selective medium had such a composition that to the above-mentioned medium was added 400 μg/ml of genetisin G-418 (manufactured by GIBCO, U.S.A., catalog No. 860-1811). The plates were cultured for about 2 weeks while changing the medium with a fresh medium on every third or fourth day, to thereby perform the cloning of transformed cells. Each of the cell clones obtained by the above-mentioned procedure was separately grown on plates for tissue culture having a diameter of 10 cm until confluent growth was attained. In the middle of the growing of the cells, the medium having an FCS concentration of 10% was changed to that having an FCS concentration of 1%. 50 μl of the cultured medium obtained using the FCS-containing selective medium was taken out and, using it, the ability to promote the activation of protein C was assayed in the manner as described in Referential Example 1. As a result, a high activity for promoting the activation of protein C was found. On the other hand, in the case of the cells transformed with plasmid pSV2-neo which was used as a control, such an activity was not detected.

Example 8

(Transformation of CHO cell with plasmid pSV2TMD4 and assay of the ability of the peptide produced by the transformed cell to promote the activation of protein C by thrombin)

Substantially the same procedures as in Example 7 except that plasmid pSV2TMD4 was used were repeated to thereby assay the ability of the peptide to promote the activation of protein C by thrombin, which peptide was produced by cells transformed with plasmid pSV2TMD4. As a result, a high activity of promoting the activation of protein C was found. On the other hand, in the case of the cells transformed with plasmid pSV2-neo which was used as a control, the activity was not detected.

Example 9

(Transformation of CHO cell with plasmid pSV2TMD2 and assay of the ability of the peptide produced by the transformed cell to promote the activation of protein C by thrombin)

Substantially the same procedures as in Example 7 except that plasmid pSV2TMD2 was used were repeated to thereby assay the ability of the peptide to promote the activation of protein C by thrombin, which peptide was produced by cells transformed with plasmid pSV2TMD2. As a result, a high activity of promoting the activation of protein C was found. On the other hand, in the case of the cells transformed with plasmid pSV2-neo which was used as a control, the activity was not detected.

Example 10

(Transformation of cHO cell with plasmid pSV2TMD1 and assay, of the ability of the peptide produced by the transformed cell to promote the activation of protein C by thrombin)

Substantially the same procedures as in Example 7 except that plasmid pSV2TMD1 was used were repeated to thereby assay the ability of the peptide to promote the activation of protein C by thrombin, which peptide was produced by cells transformed with plasmid pSV2TMD1. As a result, a high activity for promoting the activation of protein C was found. On the other hand, in the case of the cells transformed with plasmid pSV2-neo which was used as a control, the activity was not detected.

Example 11

(Transformation of CHO cell with plasmid pSV2TMJ2 and assay of the ability of the peptide produced by the transformed cell to promote the activation of protein C by thrombin)

Substantially the same procedures as in Example 7 except that plasmid pSV2TMJ2 was used were repeated to thereby assay the ability of the peptide to promote the activation of protein C by thrombin, which peptide was produced by cells transformed with plasmid pSV2TMJ2. As a result, a high activity for promoting the activation of protein C was found. On the other hand, in the case of the cells transformed with plasmid pSV2-neo and the supernatant of the culture thereof which were used as a control, the activity was not detected.

Example 12

(Transformation of $C_{127}I$ cell with plasmid pSV2TMD5 and assay for the ability of the peptide produced by the transformed cell to promote the activation of protein C by thrombin)

The plasmid pSV2TMD5 prepared in Example 1-(5) was completely digested with HindIII. Both ends of the digested plasmid were treated with DNA polymerase to make them blunt and then treated with $T_4$DNA ligase, to thereby obtain a plasmid pSV2TMD5-1 lacking a HindIII site. Subsequently, the thus obtained plasmid pSV2TMD5-1 was completely digested with restriction enzymes PvuII and BamHI to obtain a DNA fragment of about 1700 bp. The thus obtained DNA fragment was inserted in a vector which had been obtained by completely digesting a plasmid pUC18 with HincII and BamHI to thereby obtain a plasmid pUCTMD5-1. On the other hand, a plasmid pBR327 was prepared from a plasmid pBR322 (ATCC 37017) in accordance with the method of Covasrubias et al. [L. Covasrubias et al., Gene, 13, 25, (1981)]. The thus obtained plasmid pBR327 was digested with restriction enzymes BamHI and HindIII to obtain a DNA fragment of about 2960 bp. In the thus obtained DNA fragment, a DNA fragment of about 2600 bp which had been obtained by completely digesting the plasmid pUCTMD5-1 with BamHI and HindIII was inserted to obtain a plasmid pBRTMD5-1. Then, the pBRTMD5-1 and pBPV-1(9-1) (ATCC 37111) were completely digested with HindIII and the thus obtained DNA fragments were ligated with each other by means of $T_4$DNA ligase, to thereby obtain a plasmid pdBPVTMD5-1 for expression in $C_{127}$ cells. The above-mentioned process is shown in FIG. 15.

$C_{127}I$ cells (ATCC CRL1616) were transformed with the plasmid pdBPVTMD5-1 in substantially the same manner as described in Example 7. The cells were cultured in Dulbecco's MEM containing 10% FCS and 1 v/v % penicillin-streptomycin (manufactured by Flow Laboratories Inc., U.S.A., catalog No. 16-700-49) for about 3 weeks. Six cells which assumed focuses were obtained. Each of the cells was cloned on a plate for tissue culture having a diameter of 10 cm and grown to a confluent state. Then, the medium was replaced by a medium containing no FCS and the incubation was further continued for 1 day. After the incubation, 50 μl of the culture was taken out and subjected to assay for the ability to promote the activation of protein C according to the method as described in Referential Example 1. As a result, a strong activity was found.

On the other hand, in the case of the cells transformed with the plasmid pBPV-1(9-1) which was used as a control, such an activity was not detected.

Example 13

(Transformation of $C_{127}I$ cell with plasmid pSV2TMD4 and assay for the ability of the peptide produced by the transformed cell to promote the activation of protein C by thrombin)

The pSV2TMD4 prepared in Example 1-(4) was completely digested with HindIII. Both ends of the digested plasmid were treated with DNA polymerase to make them blunt and then treated with $T_4$DNA ligase, to thereby obtain a plasmid pSV2TMD4-1 lacking a HindIII site. Subsequently, the thus obtained pSV2TMD4-1 was completely digested with PvuII and BamHI, to obtain a DNA fragment of about 2100 bp. The thus obtained DNA fragment was inserted in a vector which had been obtained by completely digesting a plasmid pUC18 with HincII and BamHI to obtain a plasmid pUCTMD4-1. On the other hand, a plasmid pBR327 was prepared from plasmid pBR322 (ATCC 37017) in accordance with the method of Covasrubias et al. [L. Covasrubias et al., Gene, 13, 25, (1981)]. The thus obtained plasmid pBR327 was digested with restriction enzymes BamHI and HindIII to obtain a DNA fragment of about 2960 bp. In the thus obtained DNA fragment, a DNA fragment of about 3000 bp which had been obtained by completely digesting the plasmid pUCTMD4-1 with BamHI and HindIII was inserted to obtain a plasmid pBRTMD4-1. Then, the plasmids pBRTMD4-1 and pBPV-1(9-1)(ATCC 37111) were completely digested with HindIII and the thus obtained DNA fragments were ligated with each other by means of $T_4$DNA ligase, to thereby obtain a plasmid pdBPVTMD4-1 for expression in $C_{127}$ cells. The above-mentioned process is shown in FIG. 16.

$C_{127}$I cells (ATCC CRL1616) were transformed with the plasmid pdBPVTMD4-1 in substantially the same manner as described in Example 7. The cells were cultured in Dulbecco's MEM containing 10% FCS and 1 v/v % penicillin-streptomycin (manufactured by Flow Laboratories Inc., U.S.A., catalog No. 16-700-49) for about 3 weeks. Six cells which assumed focuses were obtained. Each of the cells was cloned on a plate for tissue culture having a diameter of 10 cm and grown to a confluent state. Then, the medium was replaced by a medium containing no FCS and the incubation was further continued for 1 day. After the incubation, 50 μl of the culture was taken out and subjected to assay for the ability to promote the activation of protein C according to the method as described in Referential Example 1. As a result, a strong activity was found. On the other hand, in the case of the cells transformed with the plasmid pBPV-1(9-1) which was used as a control, the activity was not detected.

Example 14

(Transformation of $C_{127}$I cell with plasmid pSV2TMD2 and assay for the ability of the peptide produced by the transformed cell to promote the activation of protein C by thrombin)

The plasmid pSV2TMD2 prepared in Example 1-(3) was completely digested with HindIII. Both ends of the digested plasmid were treated with DNA polymerase to make them blunt, and then treated with $T_4$DNA ligase, to thereby obtain a plasmid pSV2TMD2-1 lacking a HindIII site. Subsequently, the thus obtained plasmid pSV2TMD2-1 was completely digested with PvuII and BamHI, to obtain a DNA fragment of about 2200 bp. The thus obtained DNA fragment was inserted in a vector which had been obtained by completely digesting a plasmid pUC18 with HincII and BamHI to obtain plasmid pUCTMD2-1. On the other hand, a plasmid pBR327 was prepared from plasmid pBR322 (ATCC 37017) in accordance with the method of Covasrubias et al. [L. Covasrubias et al., Gene, 13, 25, (1981)]. The thus obtained plasmid pBR327 was digested with restriction enzymes BamHI and HindIII to obtain a DNA fragment of about 2960 bp. In the thus obtained DNA fragment, a DNA fragment of about 3070 bp which had been obtained by completely digesting the plasmid pUCTMD2-1 with BamHI and HindIII was inserted to obtain a plasmid pBRTMD2-1. Then, a DNA fragment obtained by complete digestion of the plasmid pBRTMD2-1 with HindIII was ligated to a plasmid pBPV-1(9-1)(ATCC 37111) by means of $T_4$DNA ligase, to thereby obtain a plasmid pdBPVTMD2-1 for expression in $C_{127}$ cells. The above-mentioned process is shown in FIG. 19.

$C_{127}$I cells (ATCC CRL1616) were transformed with the plasmid pdBPVTMD2-1 in the same manner as in Example 7. The cells were cultured in Dulbecco's MEM containing 10% FCS and 1 v/v % penicillin-streptomycin (manufactured by Flow Laboratories Inc., U.S.A., catalog No. 16-700-49) for about 3 weeks. Six cells which assumed focuses were obtained. Each of the cells was cloned on a plate for tissue culture having a diameter of 10 cm and grown to a confluent state. Then, the medium was replaced by a medium containing no FCS and the incubation was further continued for 1 day. After the incubation, 50 μl of the culture was taken out and subjected to assay for the ability to promote the activation of protein C according to the method as described in Referential Example 1. As a result, a strong activity was found. On the other hand, in the case of the cells transformed with the plasmid pBPV-1(9-1) which was used as a control, the activity was not detected.

Example 15

(Transformation of $C_{127}$I cell with plasmid pSV2TMD1 and assay for the ability of the peptide produced by the transformed cell to promote the activation of protein C by thrombin)

The plasmid pSV2TMD1 prepared in Example 1-(2) was completely digested with HindIII. Both ends of the digested plasmid were treated with DNA polymerase to make them blunt and then treated with $T_4$DNA ligase, to thereby obtain a plasmid pSV2TMD1-1 lacking a HindIII site. Subsequently, the thus obtained plasmid pSV2TMD1-1 was completely digested with PvuII and BamHI, to obtain a DNA fragment of about 3100 bp. The thus obtained DNA fragment was inserted in a vector which had been obtained by completely digesting a plasmid pUC18 with HincII and BamHI to obtain a plasmid pUCTMD1-1. On the other hand, a plasmid pBR327 was prepared from plasmid pBR322 (ATCC 37017) in accordance with the method of Covasrubias et al. [L. Covasrubias et al., Gene, 13, 25, (1981)]. The thus obtained plasmid pBR327 was digested with BamHI and HindIII to obtain a DNA fragment of about 2960 bp. In the thus obtained DNA fragment, a DNA fragment which had been obtained by completely digesting the plasmid pUCTMD1-1 with BamHI and HindIII was inserted to obtain a plasmid pBRTMD1-1. Then, the plasmid pBRTMD1-1 and pBPV-1(9-1)(ATCC 37111) were completely digested with HindIII and the thus obtained DNA fragments were ligated to each other by means of $T_4$DNA ligase, to thereby obtain a plasmid pdBPVTMD1-1 for expression in $C_{127}$ cells. The above-mentioned process is shown in FIG. 18.

$C_{127}$I cells (ATCC CRL1616) were transformed with the plasmid pdBPVTMD1-1 in the same manner as in Example 7. The cells were cultured in Dulbecco's MEM containing 10% FCS and 1 v/v % penicillin-streptomycin (manufactured by Flow Laboratories Inc., U.S.A., catalog No. 16-700-49) for about 3 weeks. Six cells which assumed focuses were obtained. Each of the cells was cloned on a plate for tissue culture having a diameter of 10 cm and grown to a confluent state. Then, the medium was replaced by a medium containing no FCS and the incubation was further continued for 1 day. After the incubation, 50 μl of the culture was taken out and subjected to assay for the ability to promote the activation of protein C according to the method as described in Referential Example 1. As a result, a strong activity was found. On the other hand, in the case of the cells transformed with the plasmid pBPV-1(9-1) which was used as a control, the activity was not observed.

Example 16

(Transformation of $C_{127}I$ cell with plasmid pSV2TMJ2 and assay for the ability of the peptide produced by the transformed cell to promote the activation of protein C by thrombin)

The plasmid pSV2TMJ2 prepared in Example 1 was completely digested with HindIII. Both ends of the digested plasmid were treated with DNA polymerase to make them blunt and then treated with $T_4$DNA ligase, to thereby obtain a plasmid pSV2TMJ2-1 lacking a HindIII site. Subsequently, the thus obtained plasmid pSV2TMJ2-1 was completely digested with PvuII and BamHI, to obtain a DNA fragment of about 4100 bp. The thus obtained DNA fragment was inserted in a vector which had been obtained by completely digesting a plasmid pUC18 with HincII and BamHI to obtain a plasmid pUCTMJ2-1. On the other hand, a plasmid pBR327 was prepared from plasmid pBR322 (ATCC 37017) in accordance with the method of Covasrubias et al. [L. Covasrubias et al., Gene, 13, 25, (1981)]. The thus obtained plasmid pBR327 was digested with BamHI and HindIII to obtain a DNA fragment of about 2960 bp. In the thus obtained DNA fragment, a DNA fragment which had been obtained by completely digesting the plasmid pUCTMJ2-1 with BamHI and HindIII was inserted to obtain a plasmid pBRTMJ2-1. Then, the plasmid pBRTMJ2-1 and pBPV-1(9-1)(ATCC 37111) were completely digested with HindIII and the thus obtained DNA fragments were ligated to each other by means of $T_4$DNA ligase, to thereby obtain a plasmid pdBPVTMJ2-1 for expression in $C_{127}$ cells. The above-mentioned process is shown in FIG. 19.

$C_{127}I$ cells (ATCC CRL1616) were transformed with the plasmid pdBPVTMJ2-1 in the same manner as in Example 7. The cells were cultured in Dulbecco's MEM containing 10% FCS and 1 v/v % penicillin-streptomycin (manufactured by Flow Laboratories Inc., U.S.A., catalog No. 16-700-49) for about 3 weeks. Six cells which assumed focuses were obtained. Each of the cells was cloned on a plate for tissue culture having a diameter of 10 cm and grown to a confluent state. Then, the medium was replaced by a medium containing no FCS and the incubation was further continued for 1 day. After the incubation, the cell pellet in the culture was scratched off and subjected to assay for the ability to promote the activation of protein C according to the method as described in Referential Example 1. As a result, a strong activity was found. On the other hand, in the case of the cells transformed with the plasmid pBPV-1 (9-1) which was used as a control, such an activity was not detected.

Example 17

(Purification of the peptide of the present invention)

CHO cells which were transformed with plasmids pSV2-neo and pSV2TMD5 and cultured in Example 8 were cultured in 25 plates for tissue culture each having a diameter of 10 cm. The culture medium of each plate was replaced by a fresh one four times on alternate days. Thereafter, the culture medium was completely collected (about 100 ml) and adjusted to pH 7.5, followed by purification by column chromatography using a column packed with DIP-thrombin-agarose.

Illustratively stated, DIP-thrombin (diisopropylphosphorothrombin) was prepared according to the method of N. L. Esmon et al. [J. Biol. Chem, Vol. 257, p.859 (1982)]. The DIP-thrombin was bonded to an agarose which had been treated with cyanogen bromide according to the method of P. Cuatrecasas [J. Biol. Chem., Vol. 245, p.359 (1970)], to thereby prepare DIP-thrombin-agarose.

Then, the DIP-thrombin-agarose was packed in a column having a size of 2.5 cmø×10 cm to prepare a DIP-thrombin-agarose column. The column was equilibrated at room temperature with 0.02 M Tris-HCl buffer (pH 7.5) containing 0.1 M NaCl, 0.5 mM $CaCl_2$, 1 mM benzamidine hydrochloride and 0.5% (v/v) Lubrol PX (produced by Nakarai Chemical Ltd., Japan). Subsequently, the supernatant as mentioned before was passed through the column. The column was washed with 0.02 M Tris-HCl buffer (pH 7.5) containing 0.3 M NaCl, 0.5 mM $CaCl_2$, 1 mM benzamidine hydrochloride and 0.5% (v/v) Lubrol PX, followed by elution with 0.02 M Tris-HCl buffer (pH 7.5) containing 1 M NaCl, 0.1 mM EDTA, 1 mM benzamidine hydrochloride and 0.5% (v/v) Lubrol PX, and 2.0-ml fractions were collected. With respect to each of the fractions obtained through the elution, the ability to promote the activation of protein C was assayed by the method as described hereinbefore. At the same time, the absorbance at 280 nm ($A_{280}$) of each fraction was measured by means of a spectrophotometer model UV-240 manufactured by Shimadzu Corp., Japan. Fractions having the activity were recovered and dialyzed against 0.02 M Tris-HCl buffer (pH 7.5) containing 0.1 M NaCl, 0.5 mM $CaCl_2$ and 0.5% (v/v) Lubrol PX (manufactured by Nakarai Chemical Ltd., Japan). The dialysate obtained was subjected to the second DIP-thrombin-agarose column chromatography as follows. The dialysate was passed through a DIP-thrombin-agarose column having a size of 1.5 cm ø×10 cm. The column was washed with 0.02 M Tris-HCl buffer (pH 7.5) containing 0.4 M NaCl, 0.5 mM $CaCl_2$ and 0.1% (v/v) Lubrol PX, and further washed with 0.02 M Tris-HCl buffer (pH 7.5) containing 0.4 M NaCl, 0.1 mM EDTA and 0.1% (v/v) Lubrol PX, followed by elution with 0.02 M Tris-HCl buffer (PH 7.5) containing 1 M NaCl, 0.5 mM EDTA and 0.1% (v/v) Lubrol PX. Fractions having the activity were recovered and the purified product was frozen and stored at −80° C. The value of the molecular extinction coefficient for general proteins, which is $$10.0(E_{1cm}^{1\%} \cdot 280 \text{ nm} = 10.0),$$

was applied to the purified product. Based on this coefficient, the amount of the purified product was calculated from the absorbance for the fractions containing the purified product, and was found to be about 4.7 μg.

Further, the purified product was subjected to SDS-polyacrylamide gel electrophoresis using a 5 to 10% gel gradient, and the gel was subjected to silver staining to observed any stained bands. As a result, only one band was found.

Example 18

A peptide of the present invention was produced in a purified form in substantially the same manner as in Example 17 except that plasmid pSV2TMD4 was used, and the absorbance at 280 nm was measured. The value of the molecular extinction coefficient for general proteins, which is $$10.0(E_{1cm}^{1\%} \cdot 280 \text{ nm} = 10.0),$$

was applied to the purified product. Based on this coefficient, the amount of the purified product was calculated from the absorbance for the fractions containing the purified product, and was found to be about 4.5 $\mu$g.

Further, the purified product was subjected to SDS-polyacrylamide gel electrophoresis using a 5 to 10% gel gradient, and the gel was subjected to silver staining to observe any stained bands. As a result, only one band was found.

Example 19

A peptide of the present invention was produced in a purified form in substantially the same manner as in Example 17 except that plasmid pSV2TMD2 was used, and the absorbance at 280 nm was measured. The value of the molecular extinction coefficient for general proteins, which is $$10.0(E_{1cm}^{1\%} \cdot 280 \text{ nm} = 10.0),$$

was applied to the purified product. Based on this coefficient, the amount of the purified product was calculated from the absorbance for the fractions containing the purified product, and was found to be about 4 $\mu$g.

Further, the purified product was subjected to SDS-polyacrylamide gel electrophoresis using a 5 to 10% gel gradient, and the gel was subjected to silver staining to observe any stained bands. As a result, only one band was found.

Example 20

A peptide of the present invention was produced in a purified form in substantially the same manner as in Example 17 except that plasmid pSV2TMD1 was used, and the absorbance at 280 nm was measured. The value of the molecular extinction coefficient for general proteins, which is $$10.0(E_{1cm}^{1\%} \cdot 280 \text{ nm} = 10.0),$$

was applied to the purified product. Based on this coefficient, the amount of the purified product was calculated from the absorbance for the fractions containing the purified product, and was found to be about 3 $\mu$g.

Further, the purified product was subjected to SDS-polyacrylamide gel electrophoresis using a 5 to 10% gel gradient, and the gel was subjected to silver staining to observe any stained bands. As a result, only one band was found.

Example 21

CHO cells transformed with plasmids pSV2TMJ2 and pSV2-neo were cultured on 25 plates for tissue culture each having a diameter of 10 cm by the method as described in Example 11. After the culturing, the culture was centrifuged at 800 rpm for 10 min to collect cells. The thus obtained cell pellet was suspended in 100 ml of 0.02 M Tris-HCl buffer (pH 7.5) containing 0.5%(v/v) Triton X-100, 0.25 M sucrose, 1 mM benzamidine hydrochloride and 0.5 mM $CaCl_2$ and homogenized using a Waring blender at 4° C. for 5 min (5 times), to thereby obtain a cell extract.

The thus obtained cell extract was centrifuged at 35,000 g at 10° C. for 60 min to collect a supernatant. From the supernatant, a peptide of the present invention was obtained in a purified form in substantially the same manner as in Example 17, and the absorbance at 280 nm was measured. The value of the molecular extinction coefficient for general proteins, which is $$10.0(E_{1cm}^{1\%} \cdot 280 \text{ nm} = 10.0),$$

was applied to the purified product. Based on this coefficient, the amount of the purified product was calculated from the absorbance for the fractions containing the purified product, and was found to be about 3 $\mu$g.

Further, the purified product was subjected to SDS-polyacrylamide gel electrophoresis using a 5 to 10% gel gradient, and the gel was subjected to silver staining to observe any stained bands. As a result, only one band was found.

Example 22

(Confirmation of the ability to promote the activation of protein C by thrombin)

With respect to the purified product of the peptide of the present invention, the ability to promote the activation of protein C was evaluated by the following method.

That is, to 0.02 M Tris-HCl buffer (pH 7.5) containing 0.1 M NaCl, 3.6 mM $CaCl_2$ and 10 mg/ml bovine serum albumin were added 50 $\mu$g/ml protein C, 5 nM thrombin and 5 nM of the purified product of the peptide of the present invention, and the reaction was allowed to proceed at 37° C. To the reaction mixture were added 300 $\mu$g/ml antithrombin III (manufactured by Sigma Chemical Company, U.S.A.) and 5 mM EDTA to terminate the reaction. Then, the amount of the activated protein C formed was determined by the above-mentioned method in which a synthetic substrate was used.

The results are shown in FIGS. 20 to 24. In the case (B) where the peptide of the present invention was not added, the formation of the activated protein C was not observed (dotted line). In the case (A) where the peptide of the present invention was added, the amount of protein C formed was increased with the lapse of reaction time (solid line).

Example 23

(Confirmation of anticoagulating activity)

The inhibiting effect of the peptide of the present invention on the conversion of fibrinogen to fibrin by thrombin, which leads to substantial inhibition of the blood coagulation, was determined by measuring the blood coagulation time using a Coagulometer KC-10 manufactured by Heinrich Amelung A.G. (West Germany). That is, to 0.05M Tris-HCl buffer (pH 7.5) containing 5 mM $CaCl_2$ and 0.1 M NaCl was added 3.0 $\mu$g of fibrinogen (Fraction I, manufactured by Sigma Chemical Company, U.S.A.). To the resultant mixture was added 0 to 50 nM of the purified peptide of the present invention. Then, 10 nM thrombin was added to the mixture in such an amount that the total amount of the resultant mixture became 0.4 ml, and the coagulation time was measured.

The results are shown in FIGS. 25 to 29. It was confirmed that the higher the amount of the purified peptide added relative to the amount of thrombin, the longer the blood coagulation time.

Example 24

(Confirmation of platelet aggregation-inhibiting activity)

The effect of the peptide of the present invention on substantial inhibition of the platelet-aggregating activity of thrombin was evaluated using a Platelet Aggregometer manufactured by SIENCO Co., Ltd. (U.S.A.). As a result, it was found that when one unit (about 0.4 μg) of thrombin was added to 250 μA of a solution containing 300,000 cells/μl of blood platelets (Platelet Rich Plasma, P.R.P.), the aggregation of platelets occurred. By contrast, when the purified product of the peptide of the present invention was added, before the addition of thrombin, in a molar amount equal to or more than that of thrombin to be added, the aggregation of platelets did not occur.

[Application Examples]

Applications of the peptide of the present invention will be described with reference to the following Application Examples, which should not be construed to be limiting the scope of the present invention.

| Application Example 1 | |
| --- | --- |
| Purified product of the peptide of the present invention | 10 mg |
| Purified gelatin | 20 mg |
| Mannitol | 100 mg |
| Sodium chloride | 7.8 mg |
| Sodium phosphate | 15.4 mg |

The above-mentioned components were dissolved in 2 ml of distilled water for injection, and put in a sterilized vial. Then, the vial was preliminarily frozen at −35° C. for 2 hours, and subjected to a first drying at −35° C. under vacuum of 0.075 Torr for 35 hours, followed by a second drying at 30° C. under vacuum of 0.03 Torr for 5 hours, to thereby prepare an injection contained in a vial. The composition thus obtained is dissolved in 500 ml of physiological saline or a glucose injection just before the administration, and used for intravenous drip infusion.

| Application Example 2 | |
| --- | --- |
| Purified product of the peptide of the present invention | 2.5 mg |
| Albumin | 5 mg |
| Mannitol | 25 mg |
| Sodium chloride | 1.95 mg |
| Sodium phosphate | 3.85 mg |

Using the above-mentioned components, an injection contained in a vial was prepared in substantially the same manner as in Application Example 1.

BRIEF DESCRIPTION OF THE DRAWINGS

FIGS. 2 (a) to (b) show the base sequence of a DNA fragment TM13 obtained in Referential Example 3-(2);

FIGS. 3 (a) to (d) show the base sequence of a DNA fragment TM137 obtained in Referential Example 3-(5);

FIGS. 4(a) to (b) show the base sequence of a DNA fragment TMP5 obtained in Referential Example 3-(7);

FIG. 5 shows the base sequence of a DNA fragment TMP26 obtained in Referential Example 3-(10);

PROBABILITY OF UTILIZATION IN INDUSTRY

Figure 1:
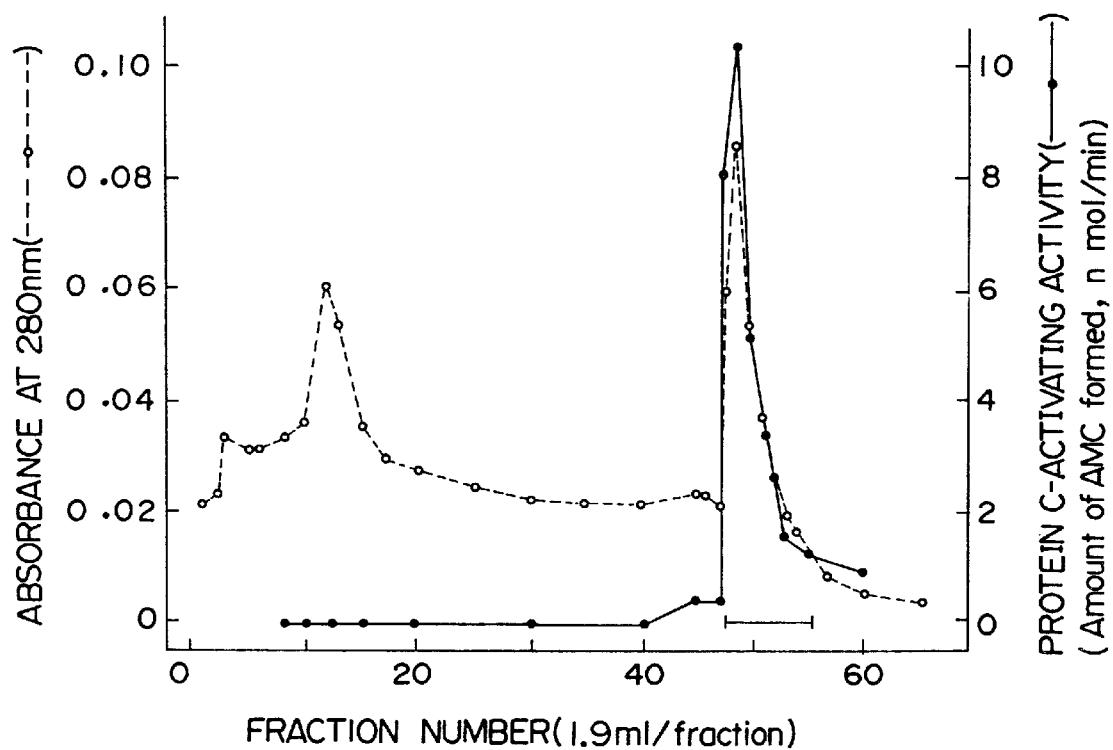
FIG. 1 is a graph showing the results obtained by subjecting the purified peptide which was prepared from human lungs and had the ability to promote the activation of protein C by thrombin, to the fourth DIP-thrombin-agarose column chromatography in Referential Example 2.
Figure 6:
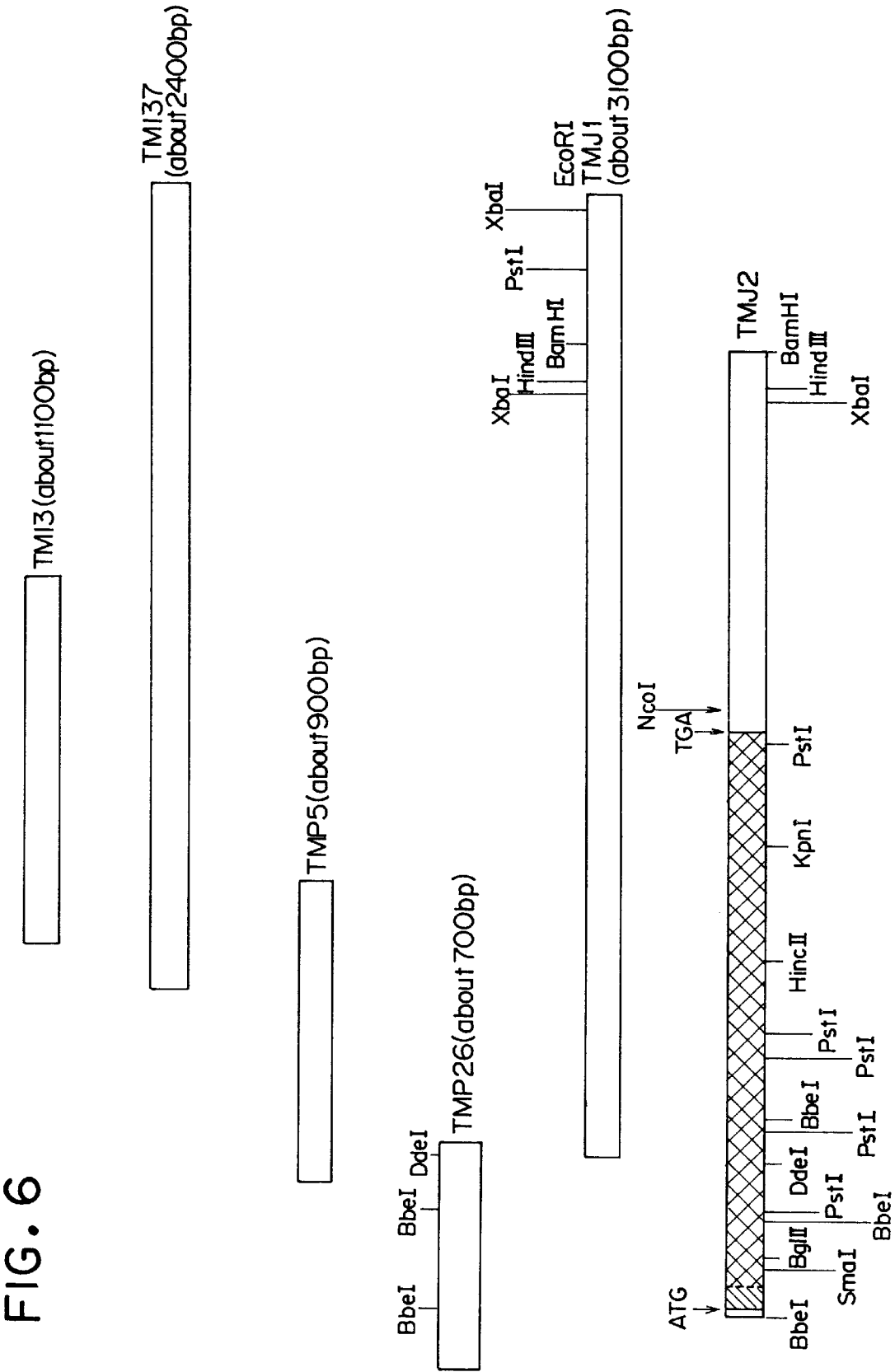
FIG. 6 shows the restriction endonuclease cleavage maps of the above-mentioned DNA fragments TMP13, TM137, TMP5 and TMP26, and the restriction endonuclease cleavage maps of DNA fragments TMJ1 and TMJ2 respectively obtained in Referential Examples 3-(13-1) and 3-(13-2) and also shows the relationship between those DNA fragments with respect to the correspondence of the base sequences, in which the respective portions of the DNA fragments which overlap as viewed in the vertical direction have common base sequences to one another. In the Figure, the portion comprising the hatched portion and crosshatched portion indicated in the restriction endonuclease cleavage map of a DNA fragment TMJ2 is a possible open reading frame, and the base sequence coding for a peptide of the present invention is present in the crosshatched portion.
Figure 7:
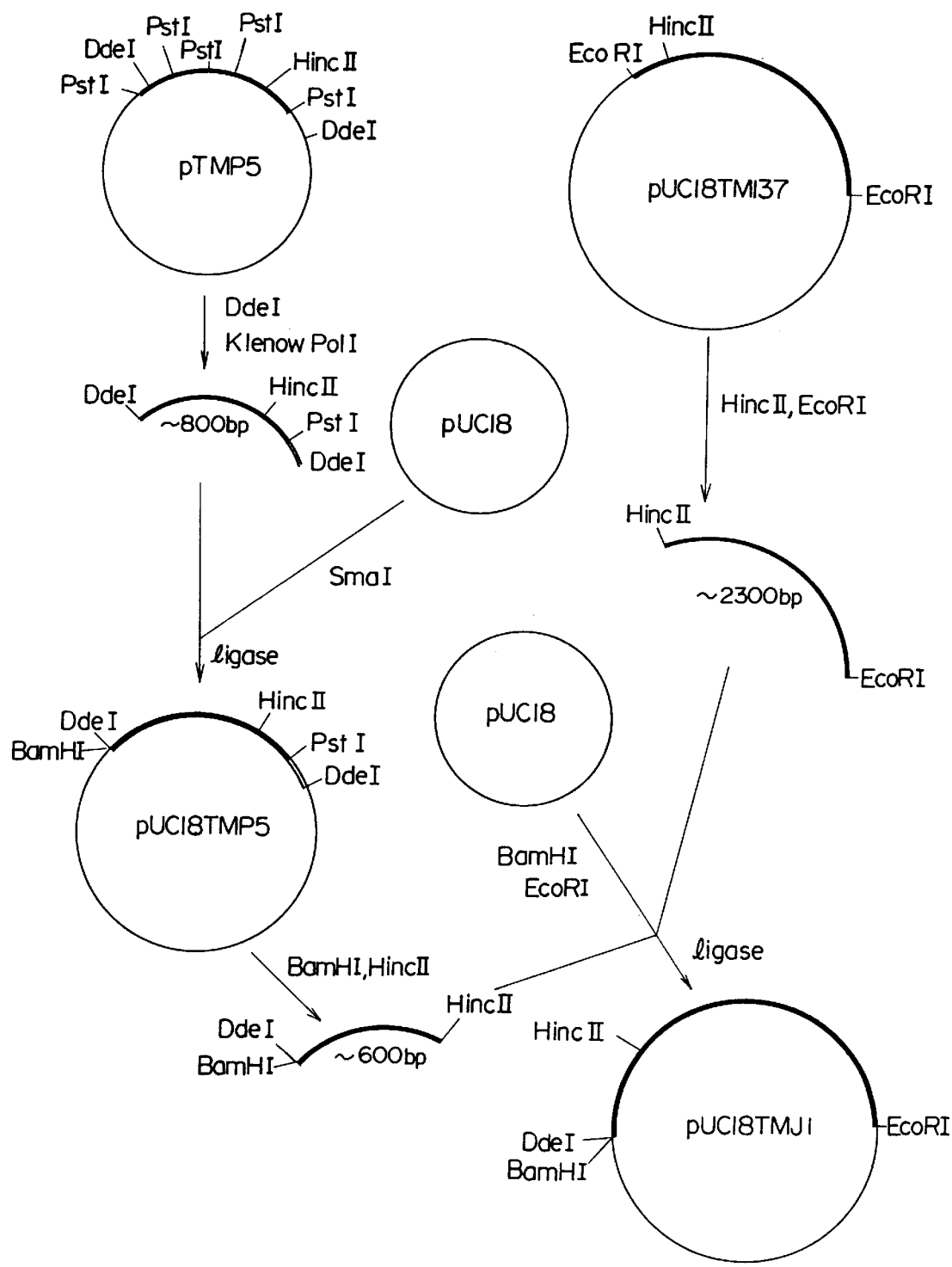
FIG. 7 shows a flow chart illustrating the construction of plasmid pUC18TMJ1 which contains the TMJ1 and, ligated thereto, the TMP5.
Figure 8:
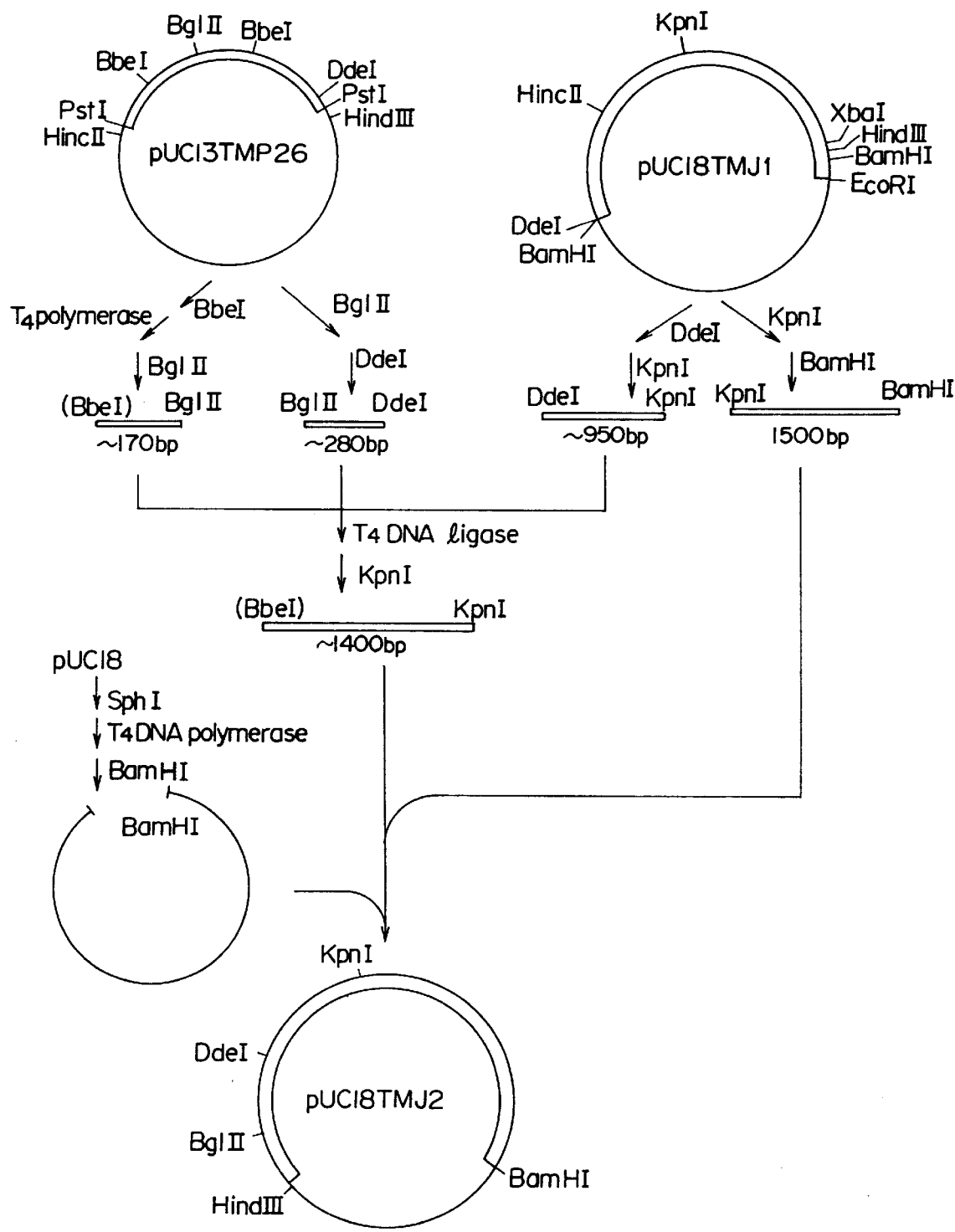
FIG. 8 shows a flow chart illustrating the construction of plasmid pUC18TMJ2 which contains the TMJ1 and, ligated thereto, the TMP26.
Figure 9:
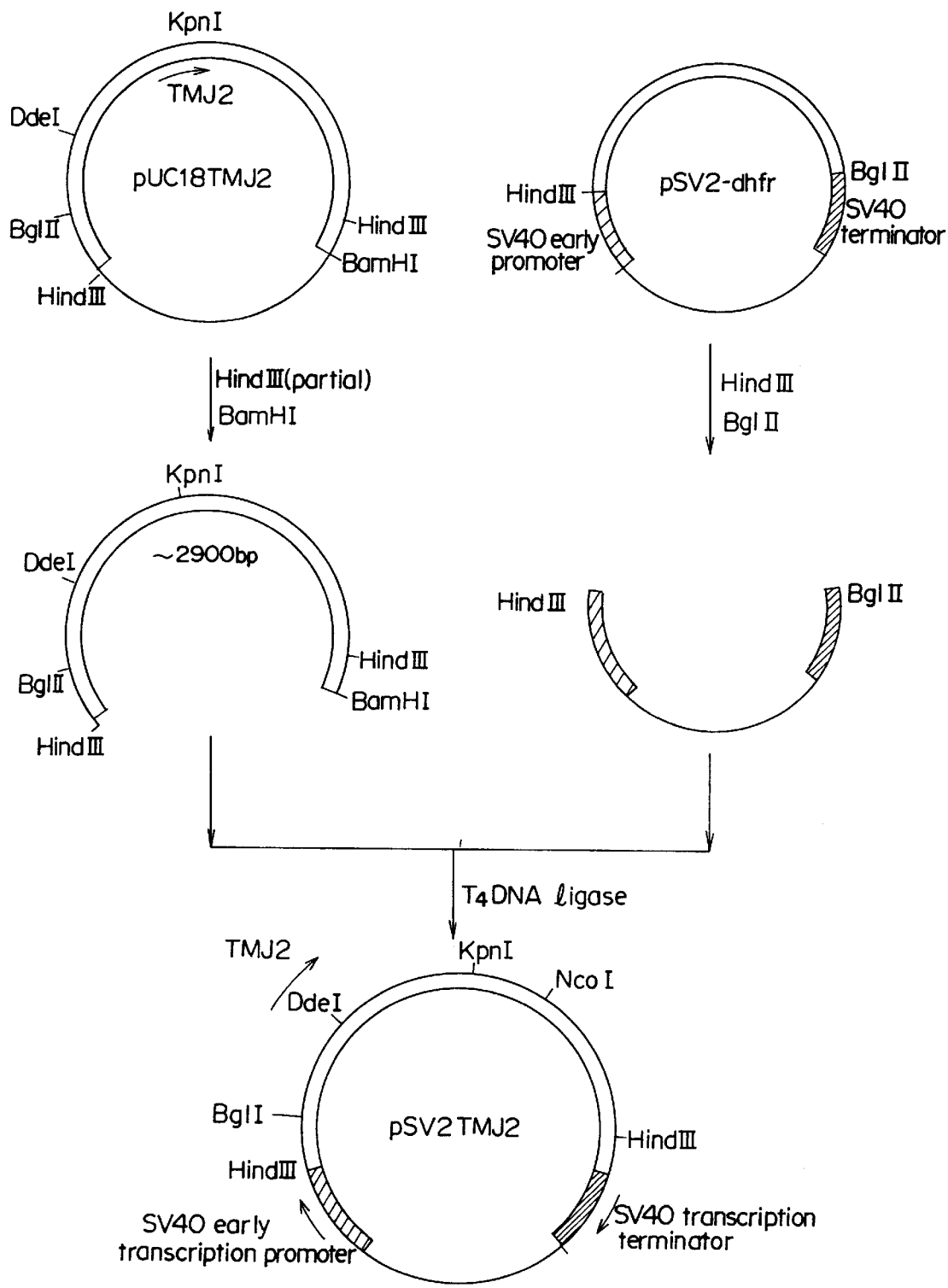
FIG. 9 shows a flow chart illustrating the construction of a plasmid pSV2TMJ2 obtained by the insertion of the TMJ2 in an expression vector for an animal cell host.
Figure 10:
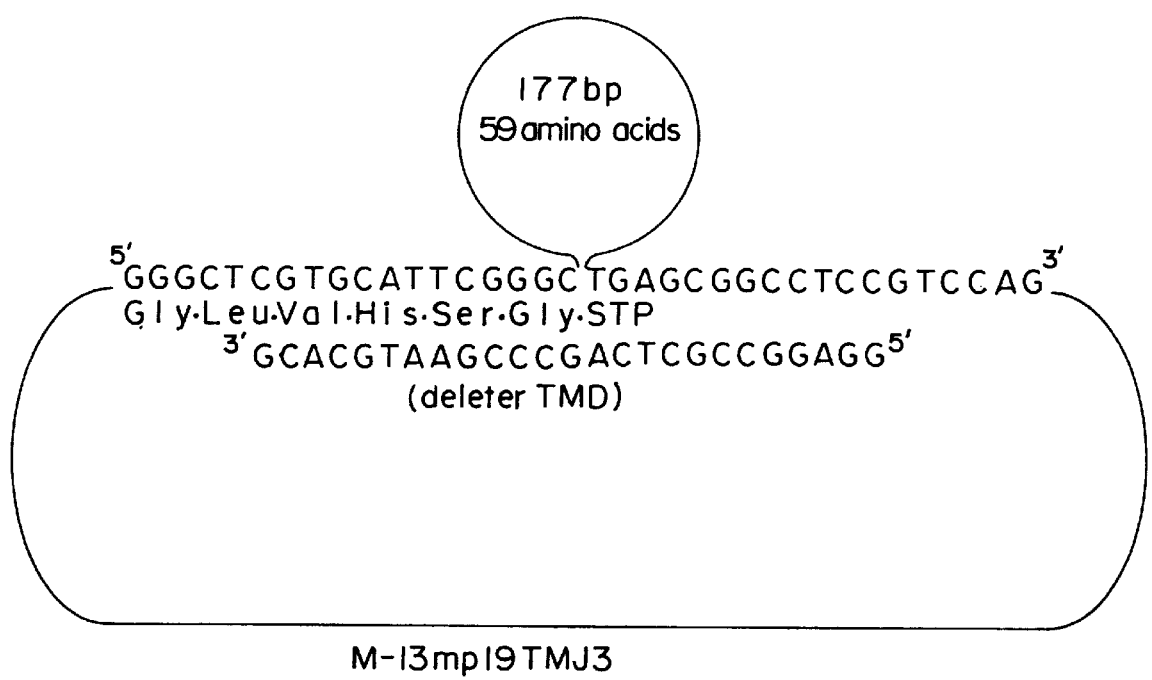
FIG. 10 is an illustration of a recombinant plasmid M-13mp19TMJ3 obtained in Example 1-(2)-(a) with which a deleter TMD is complementarily hybridized, showing the base sequence around the portion at which the deleter is hybridized with the plasmid, together with the amino acid sequence encoded thereby.
Figure 11:
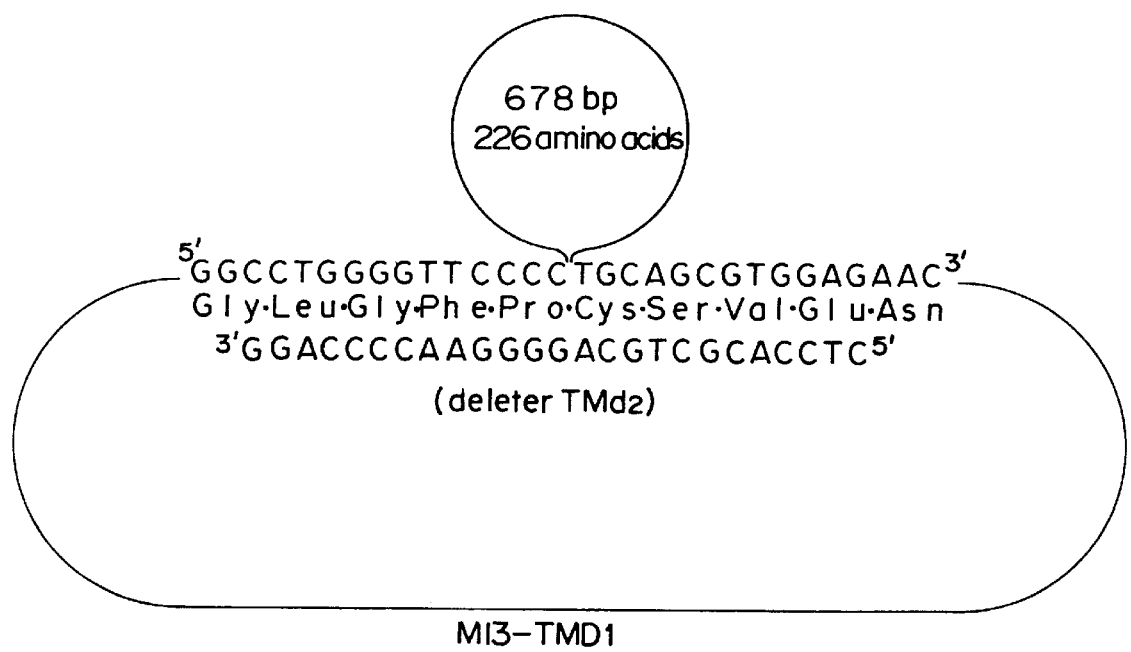
FIG. 11 is an illustration of a recombinant plasmid pSV2TMD1 obtained in Example 1-(2)-(b) with which a deleter $TMd_2$ is complementarily hybridized, showing the base sequence around the portion at which the deleter is hybridized with the plasmid, together with the amino acid sequence encoded thereby.
Figure 12:
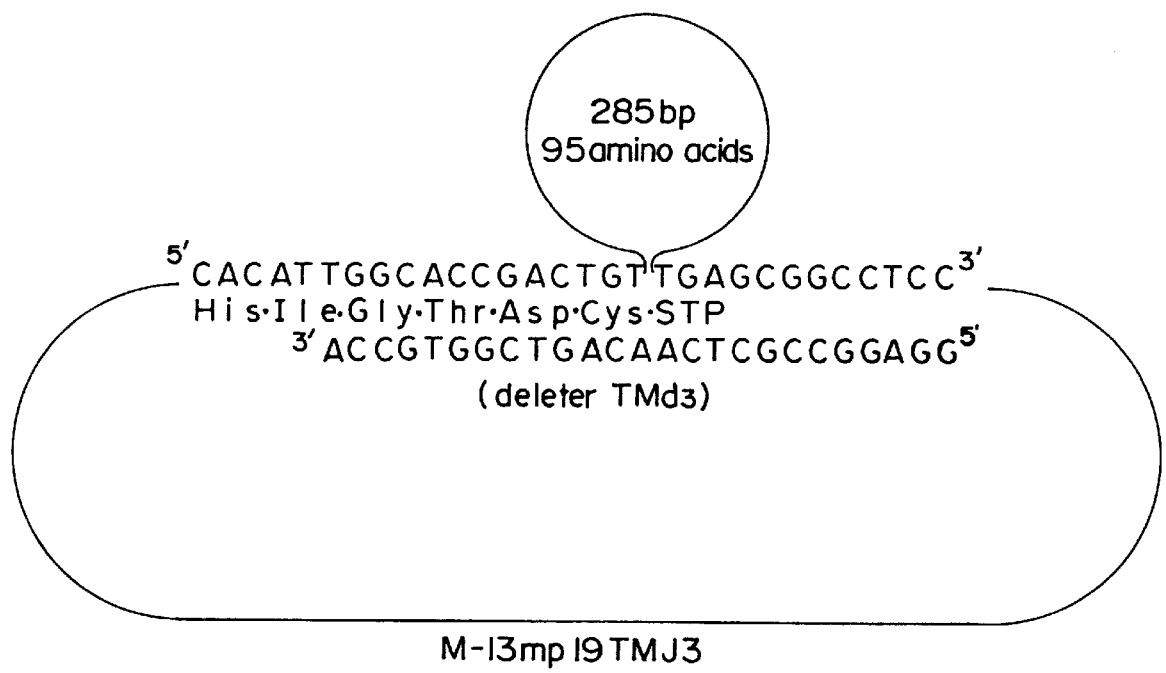
FIG. 12 is an illustration of a recombinant plasmid M-13mp19TMJ3 obtained in Example 1-(2)-(a) with which a deleter $TMd_3$ is complementarily hybridized, showing the base sequence around the portion at which the deleter is hybridized with the plasmid, together with the amino acid sequence encoded thereby.
Figure 13:
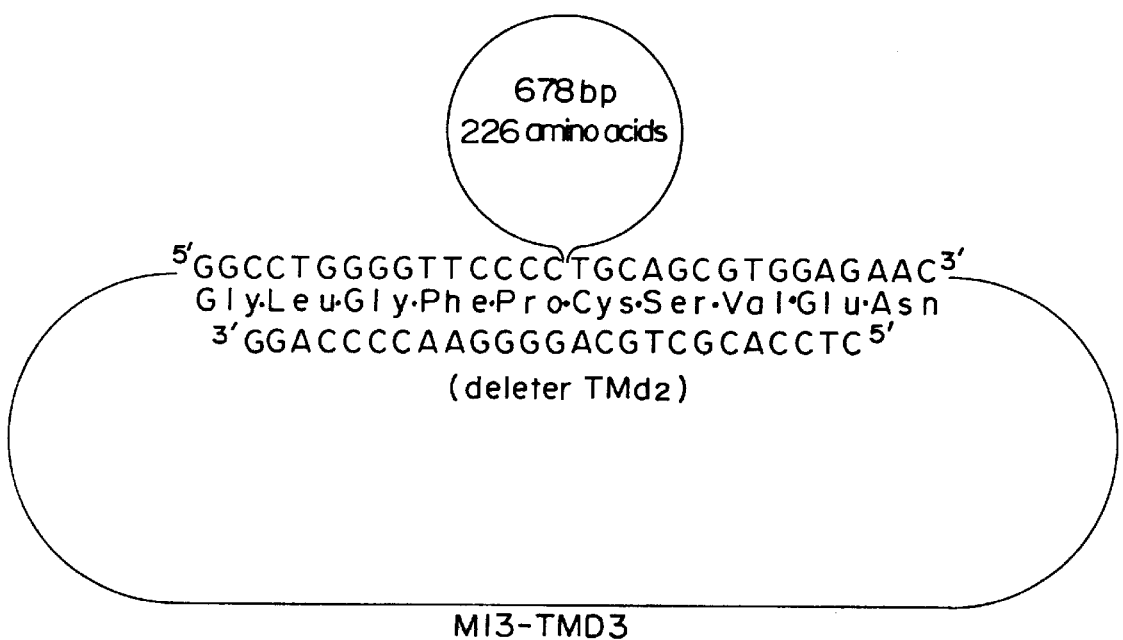
FIG. 13 is an illustration of a recombinant plasmid M13-TMD3 obtained in Example 1-(4)-(a) with which a deleter $TMd_2$ is complementarily hybridized, showing the base sequence around the portion at which the deleter is hybridized with the plasmid, together with the amino acid sequence encoded thereby.
Figure 14:
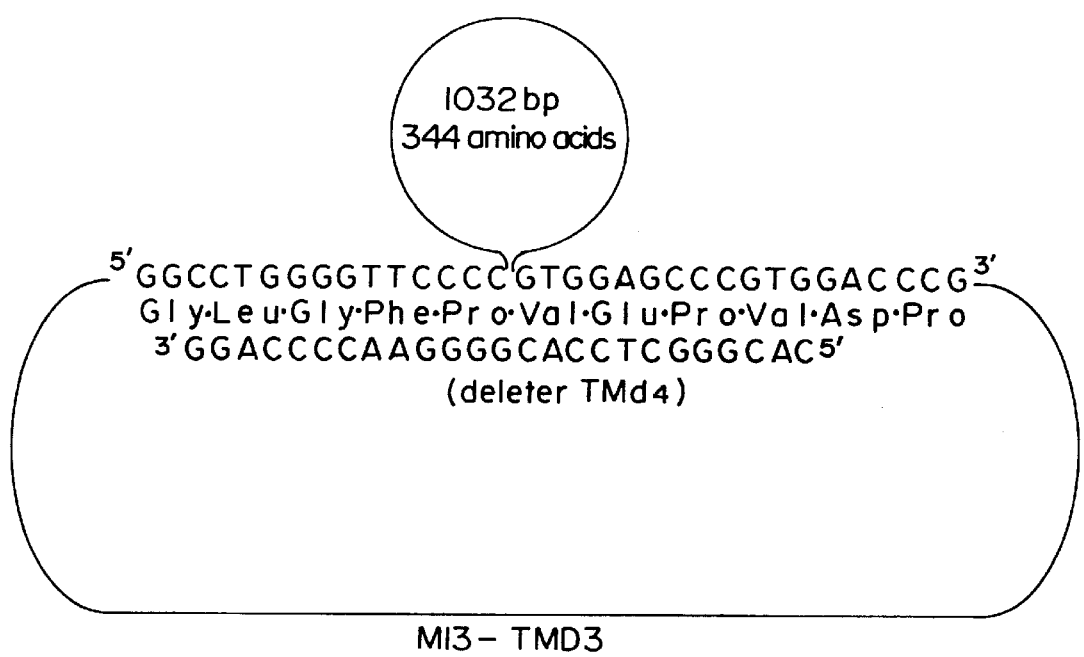
FIG. 14 is an illustration of a recombinant plasmid M13-TMD3 obtained in Example 1-(4)-(a) with which a deleter $TMd_4$ is complementarily hybridized, showing the base sequence around the portion at which the deleter is hybridized with the plasmid, together with the amino acid sequence encoded thereby.
Figure 15:
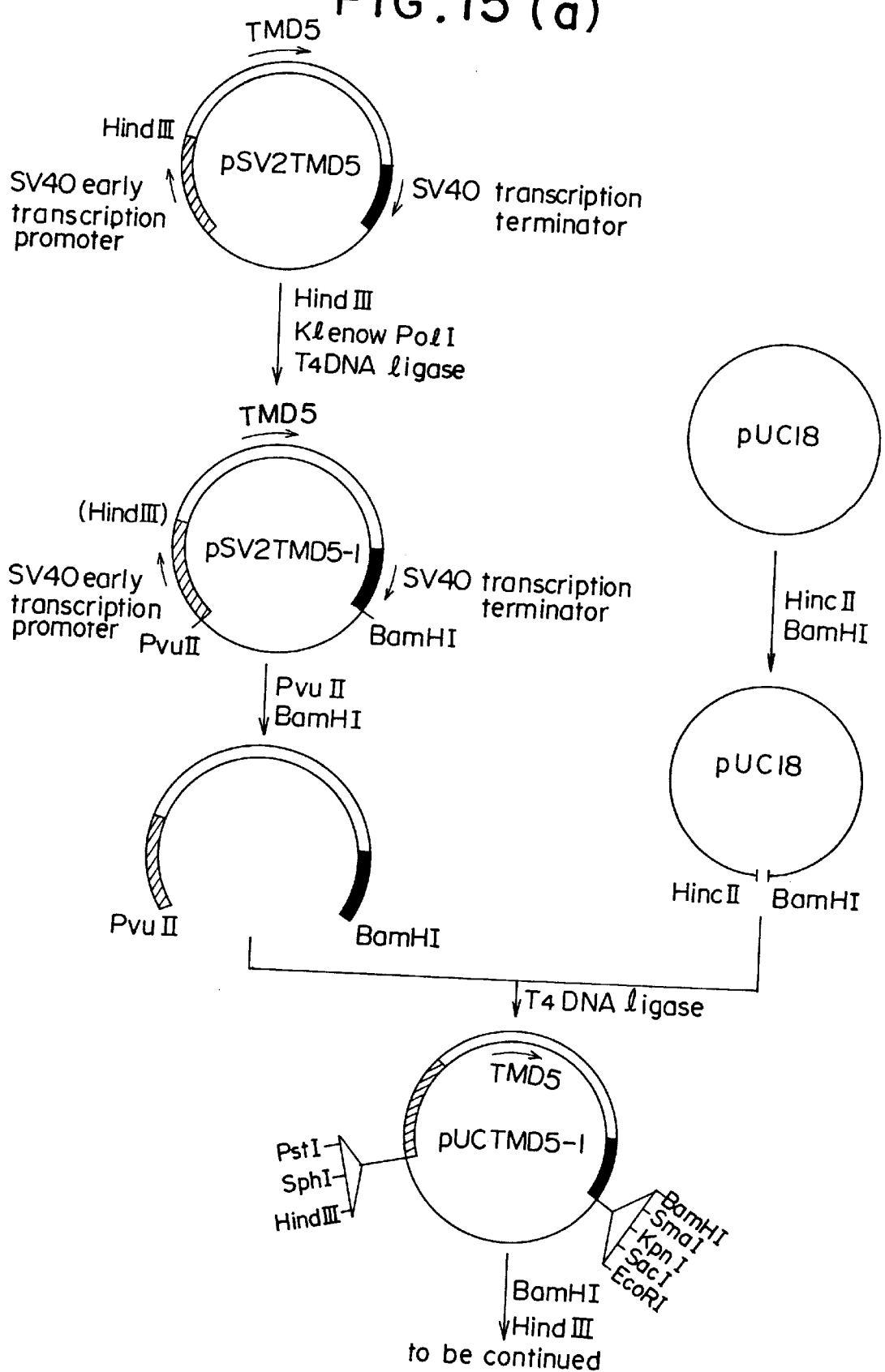
FIGS. 15A–B shows a flow chart illustrating the construction of a plasmid pdBPVTMD5-1 which is a replicable recombinant DNA of the present invention.
Figure 15B:
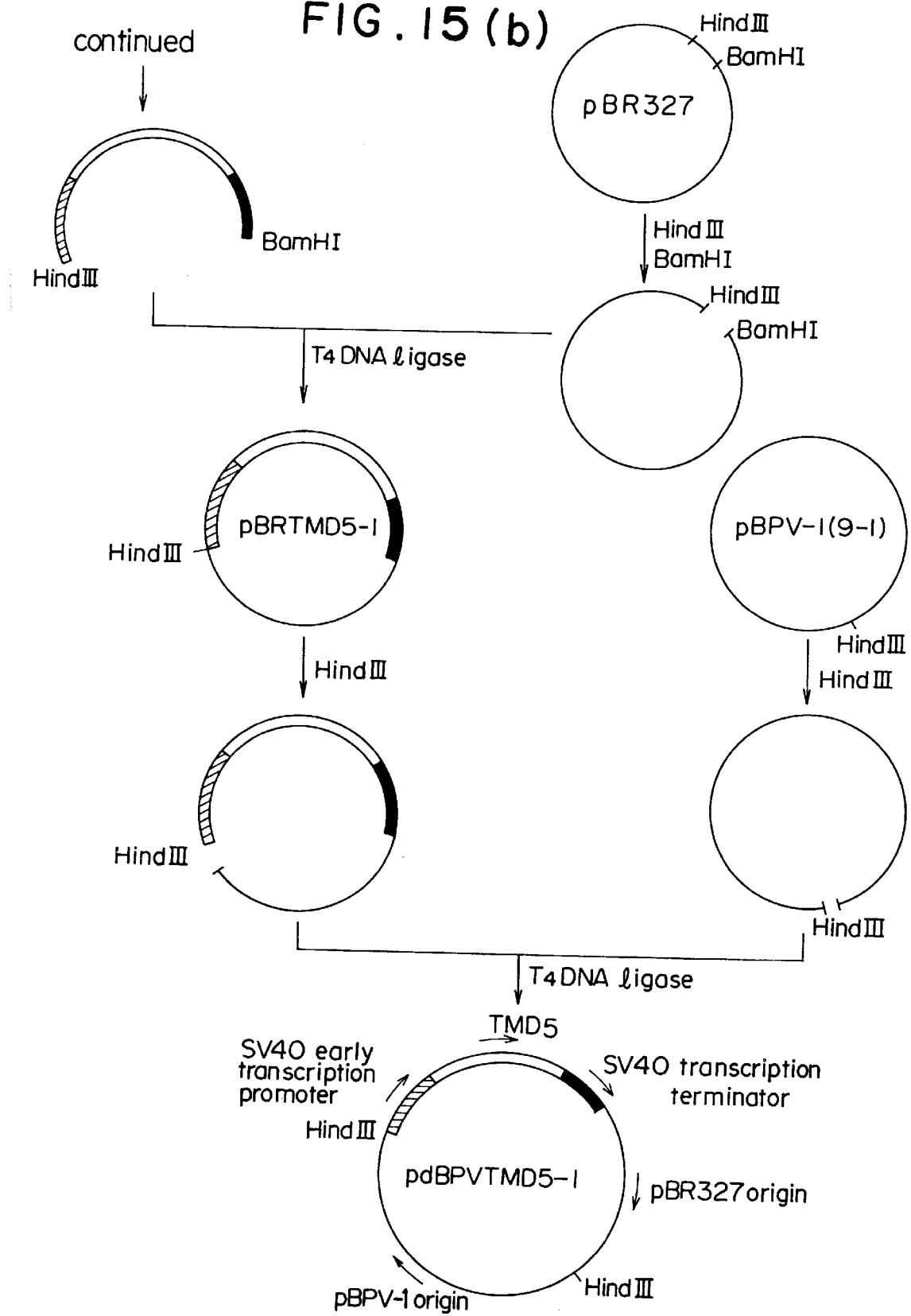
Figure 16:
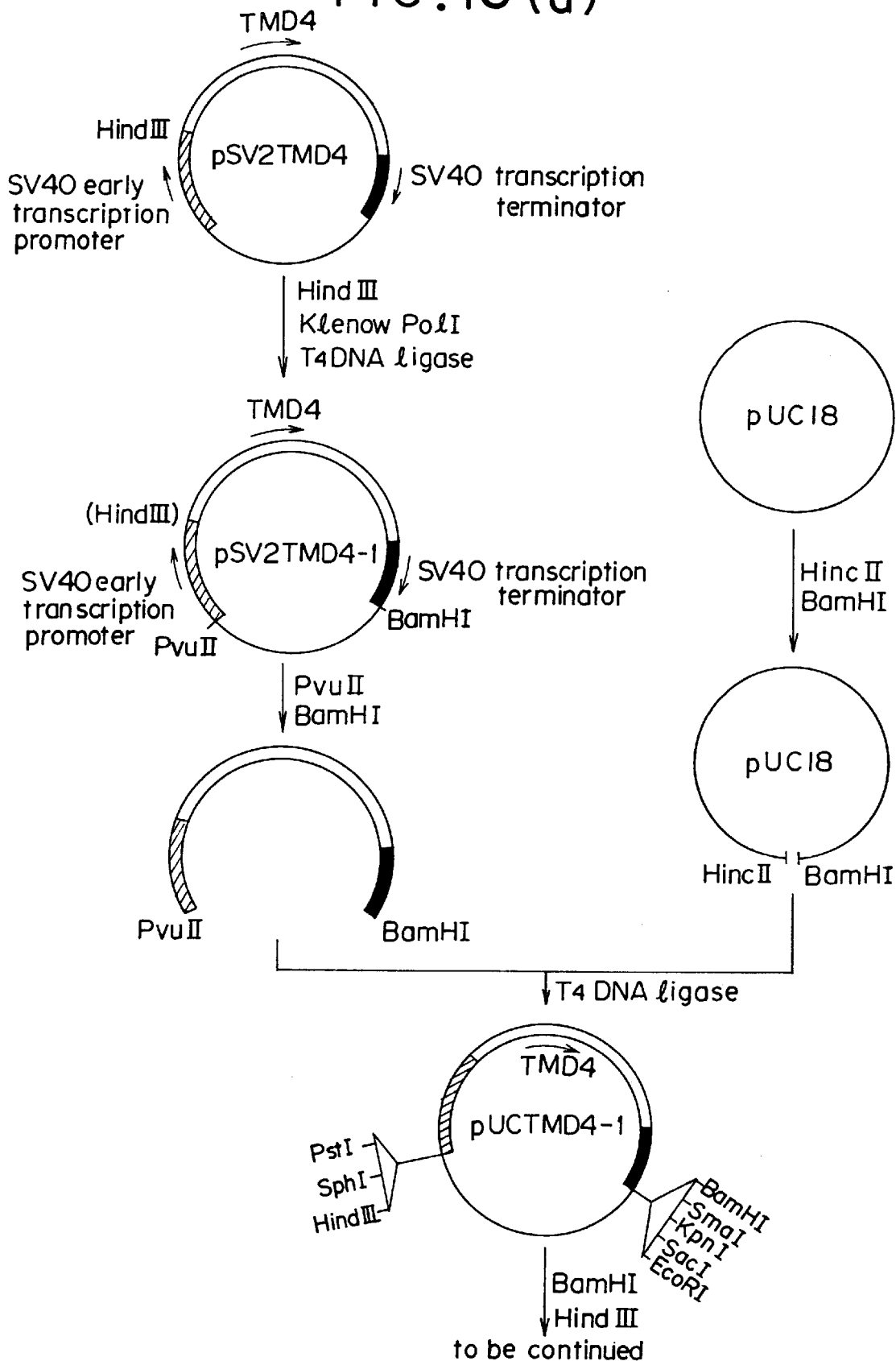
FIGS. 16A–B shows a flow chart illustrating the construction of a plasmid pdBPVTMD4-1 which is a replicable recombinant DNA of the present invention.
Figure 17A:
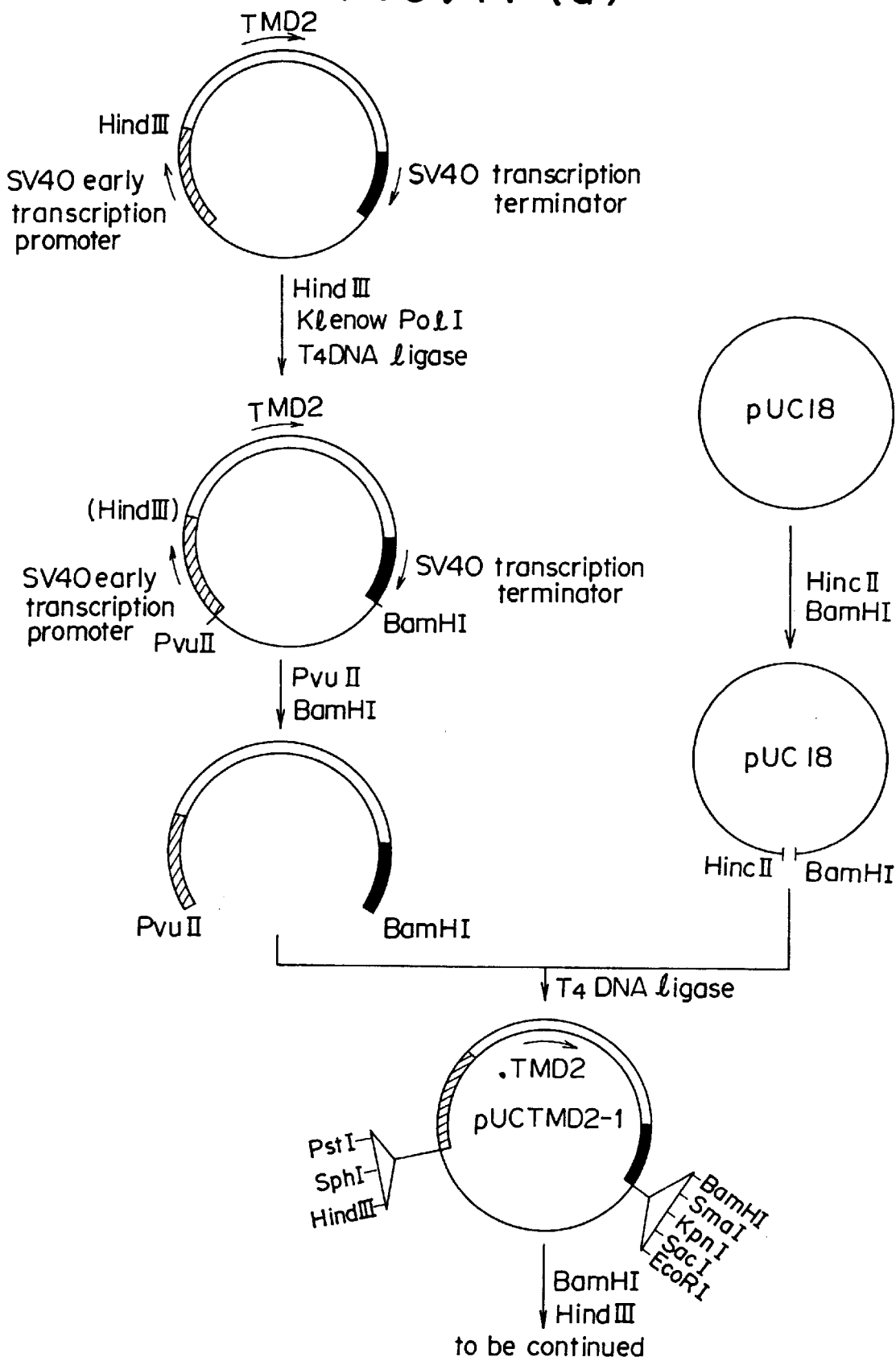
FIGS. 17A–B shows a flow chart illustrating the construction of a plasmid pdBPVTMD2-1 which is a replicable recombinant DNA of the present invention.
Figure 17:
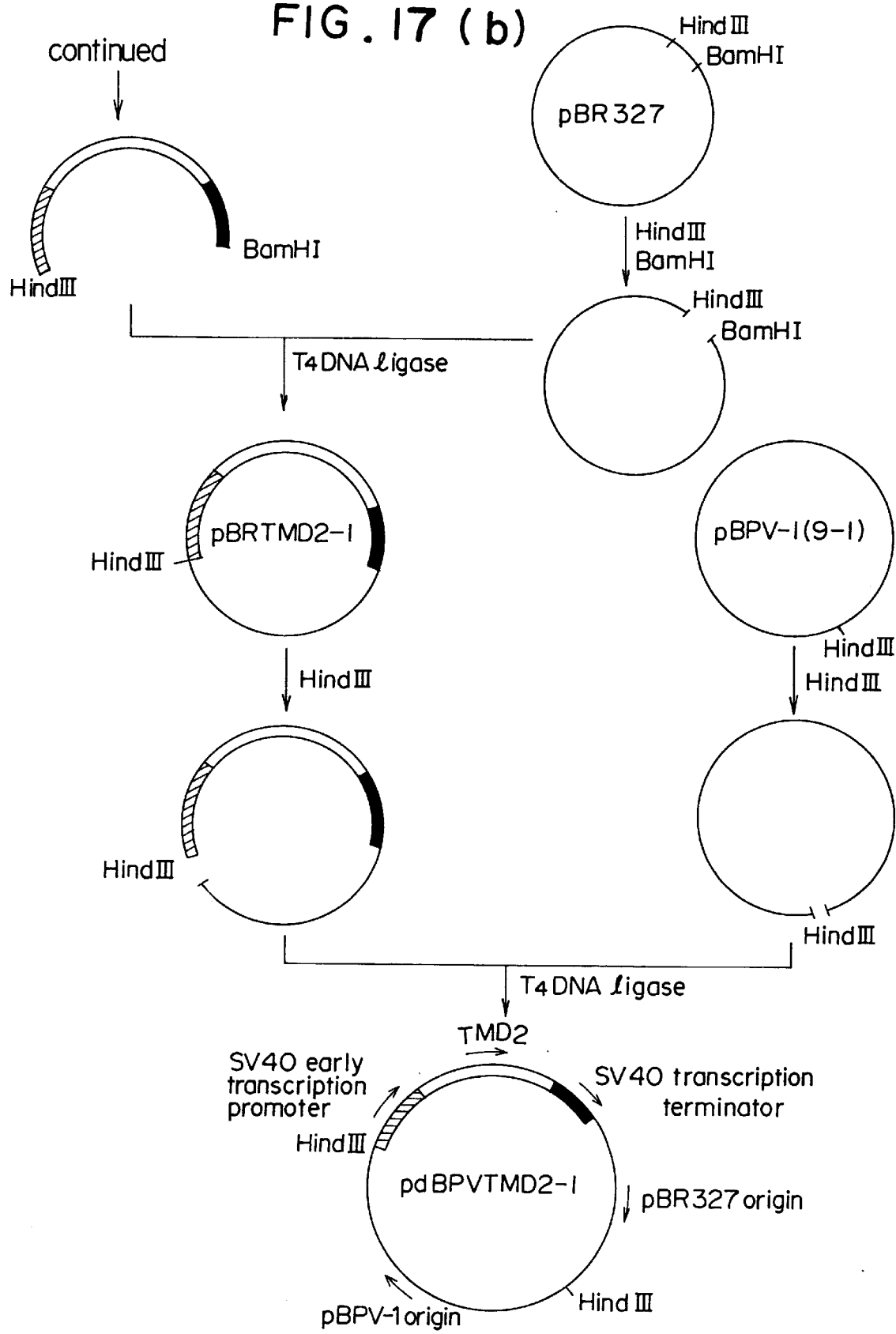
Figure 18:
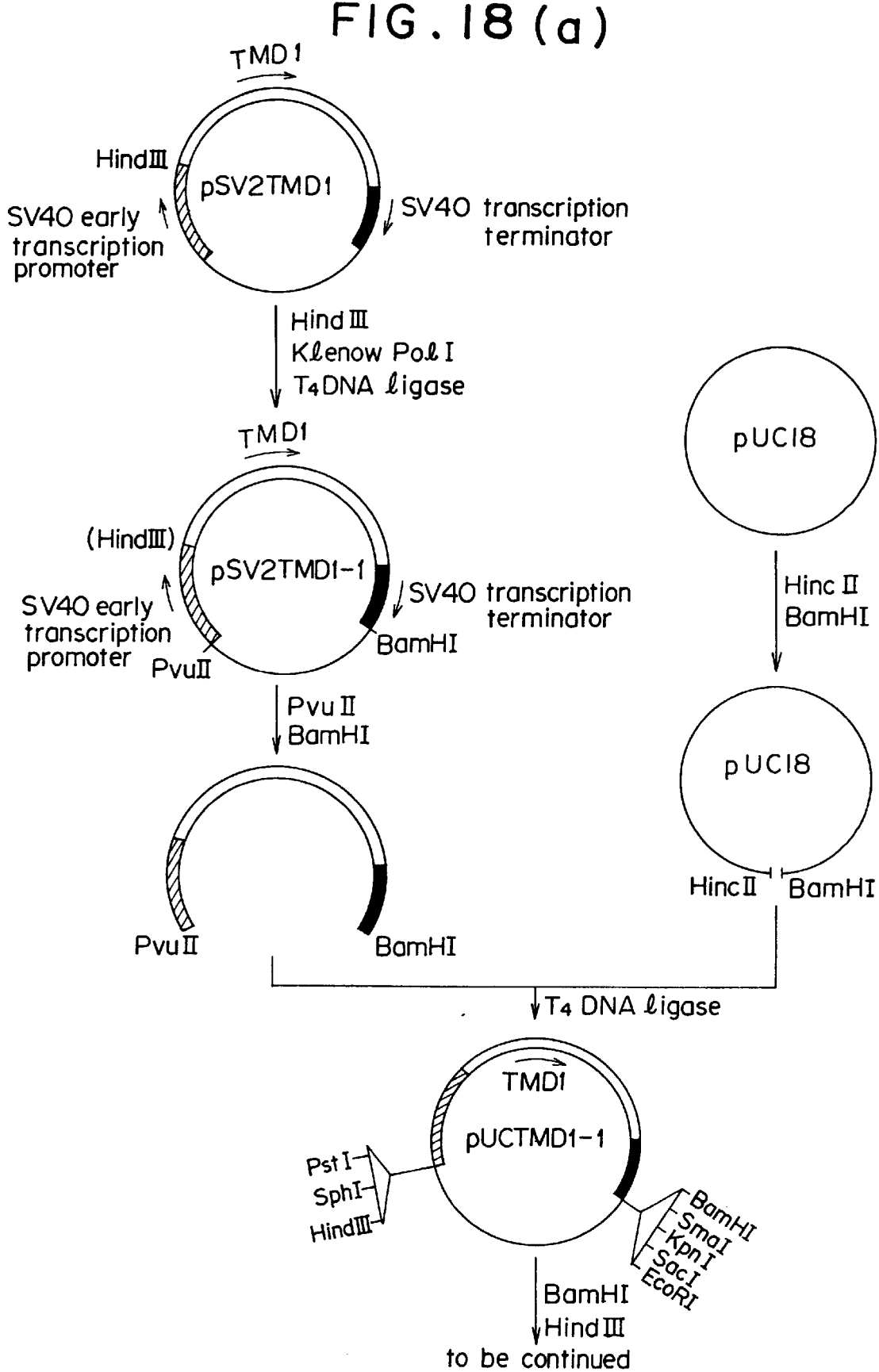
FIGS. 18A–B shows a flow chart illustrating the construction of a plasmid pdBPVTMD1-1 which is a replicable recombinant DNA of the present invention.
Figure 18B:
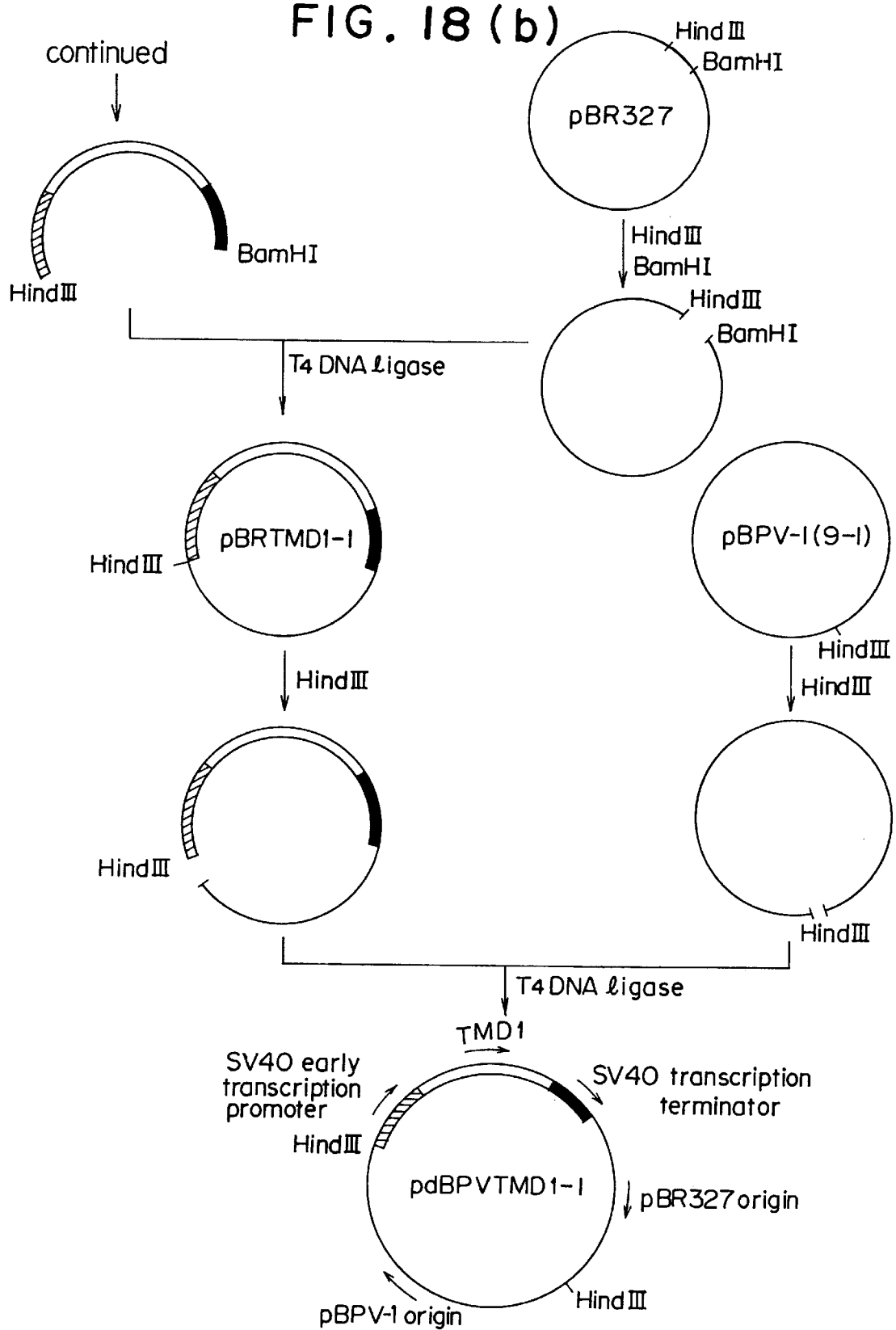
Figure 19A:
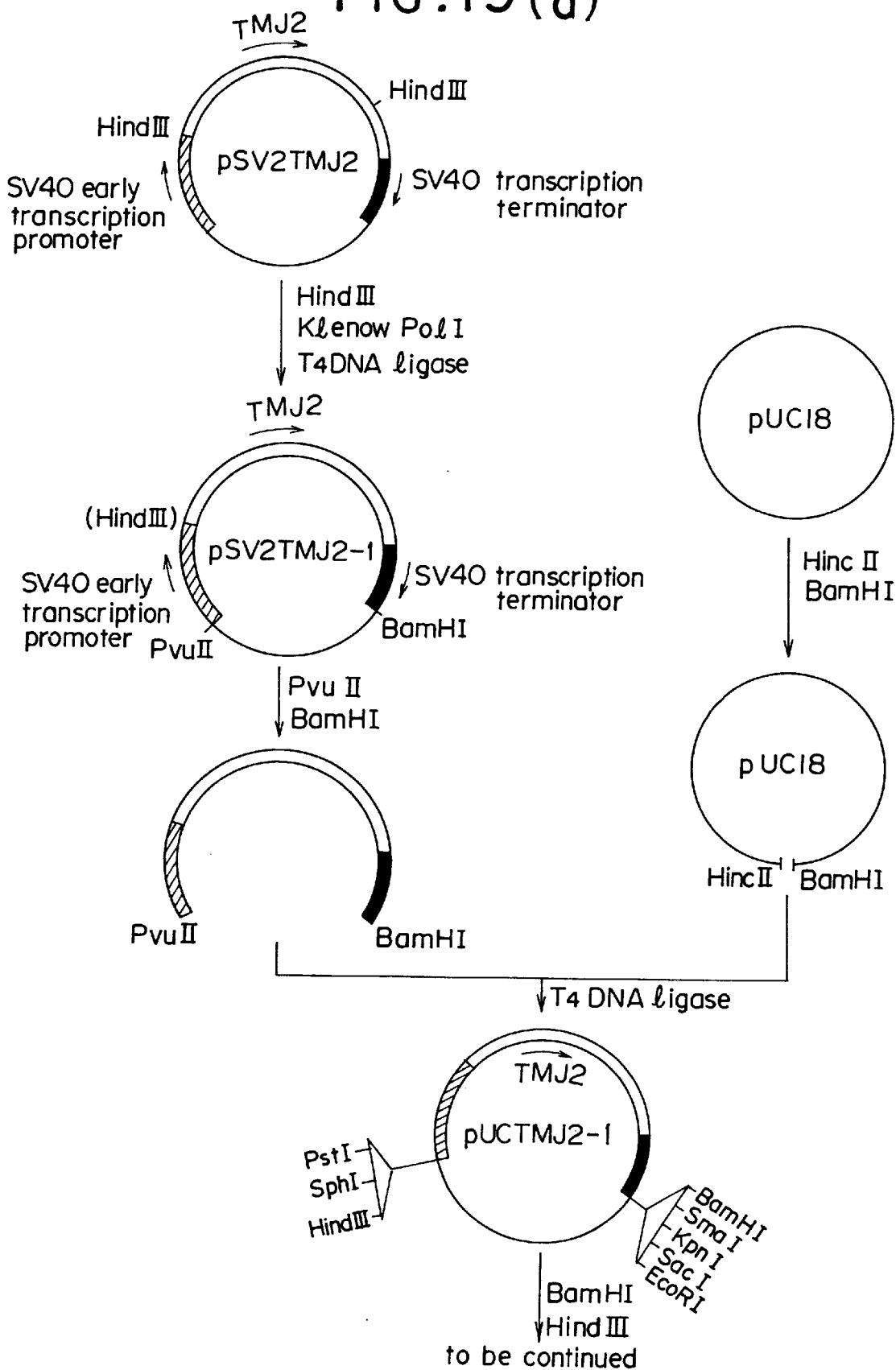
FIGS. 19A–B shows a flow chart illustrating the construction of a plasmid pdBPVTMJ2-1 which is a replicable recombinant DNA of the present invention.
Figure 19B:
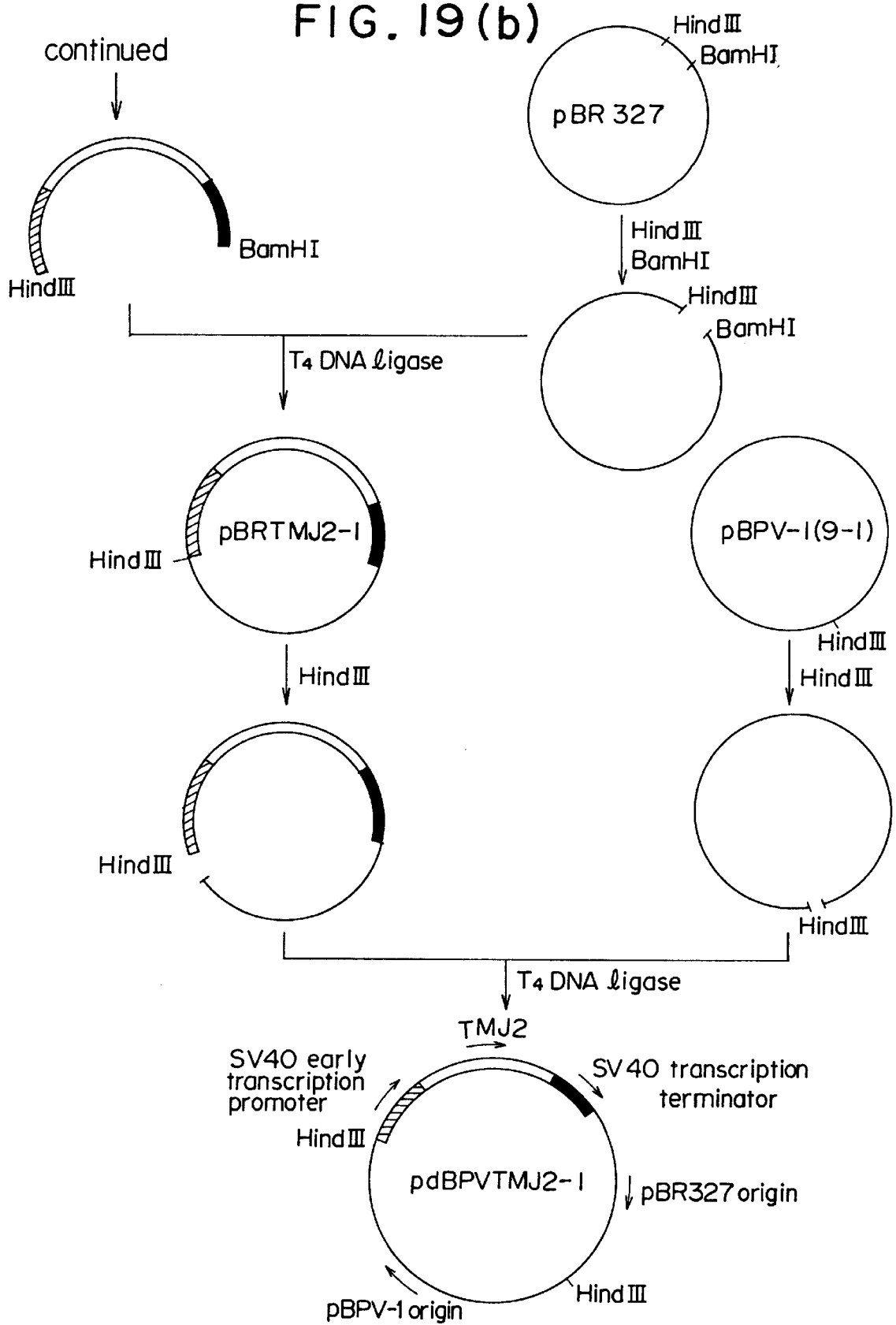
Figure 20:
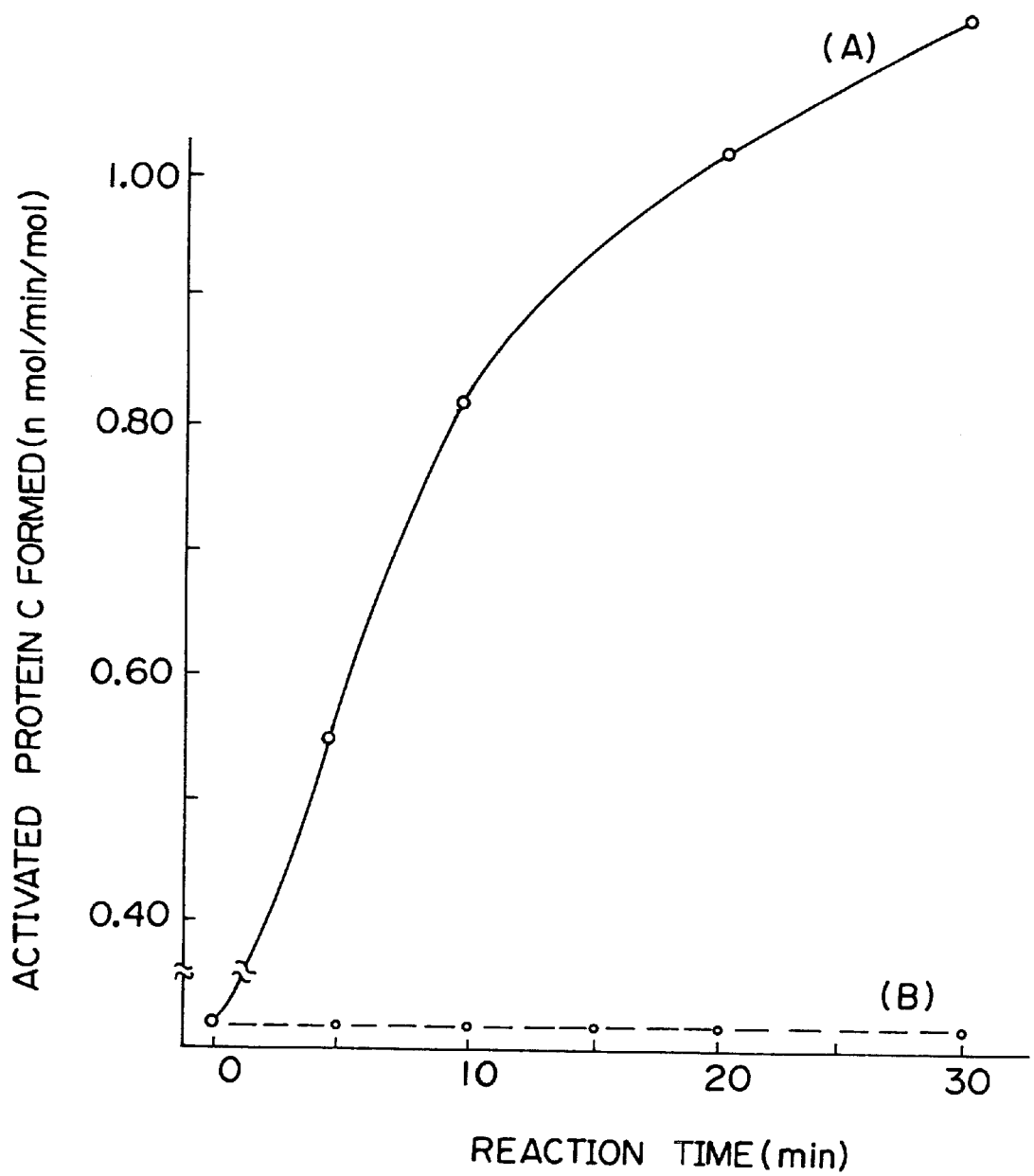
FIGS. 20 to 24 are graphs showing the relationships between the amount of the activated protein C formed by the reaction of protein C and thrombin and the reaction time, in which a comparison is made between the presence of and the absence of a purified peptide of the present invention.
Figure 21:
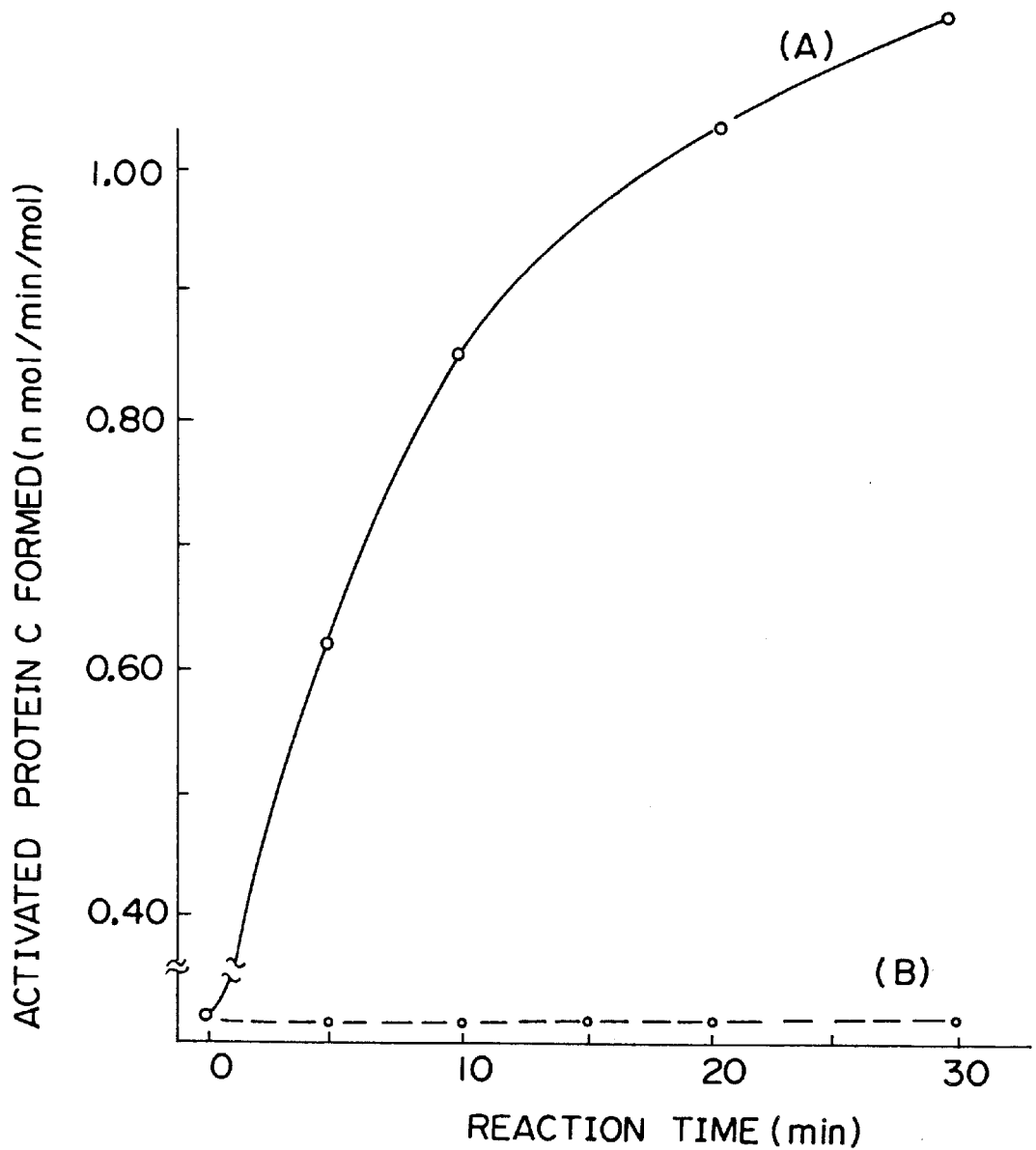
Figure 22:
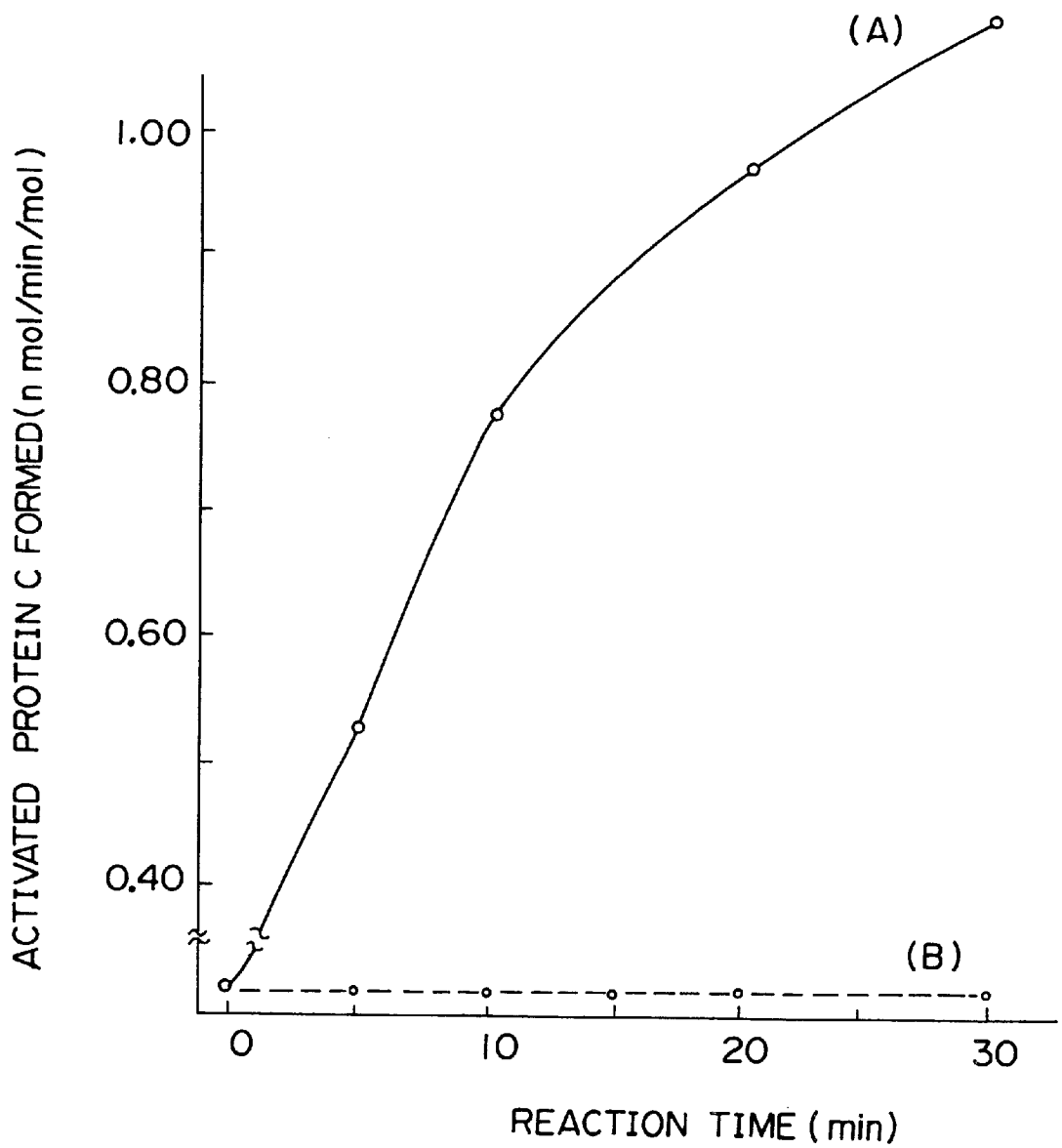
Figure 23:
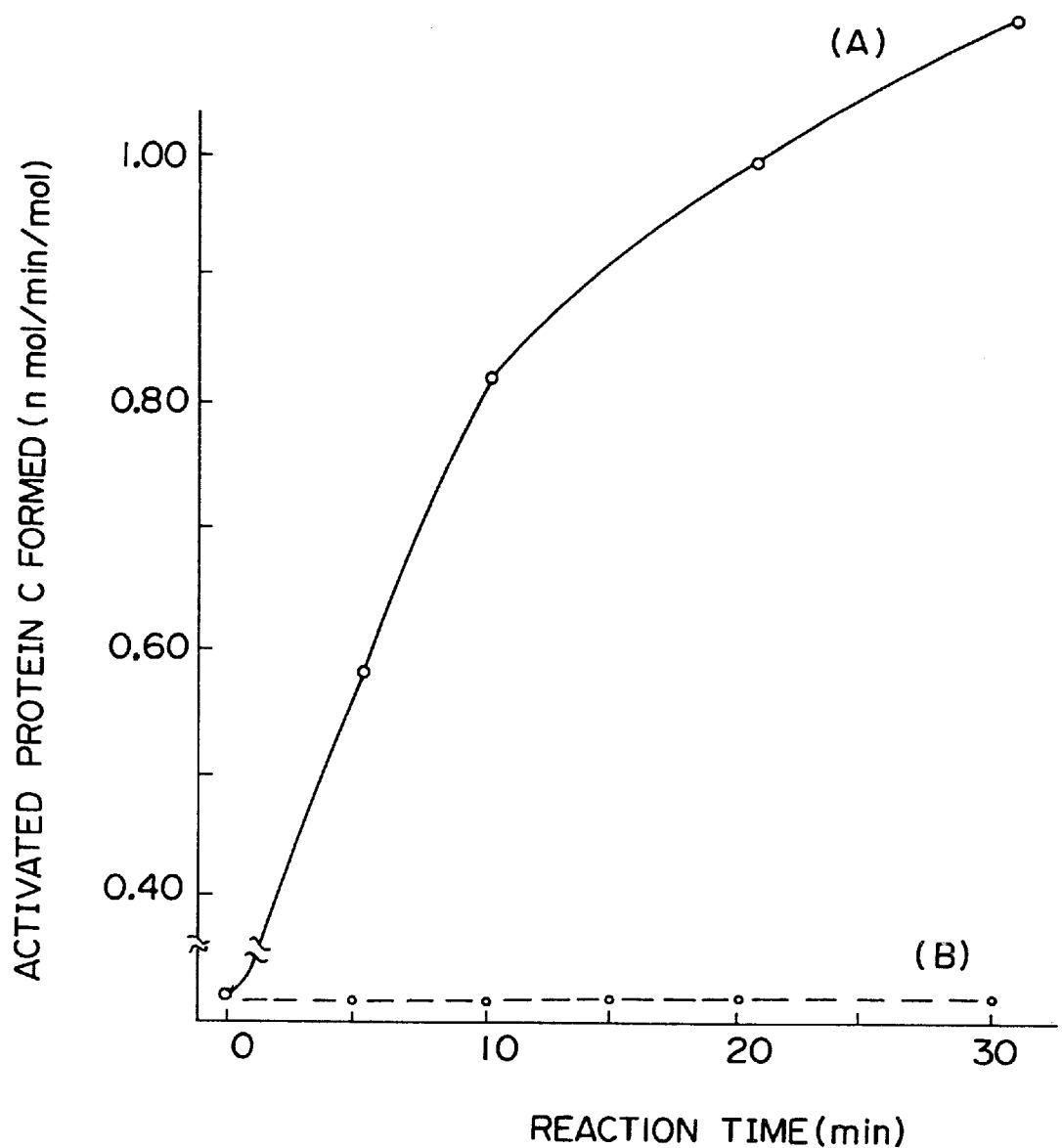
Figure 24:
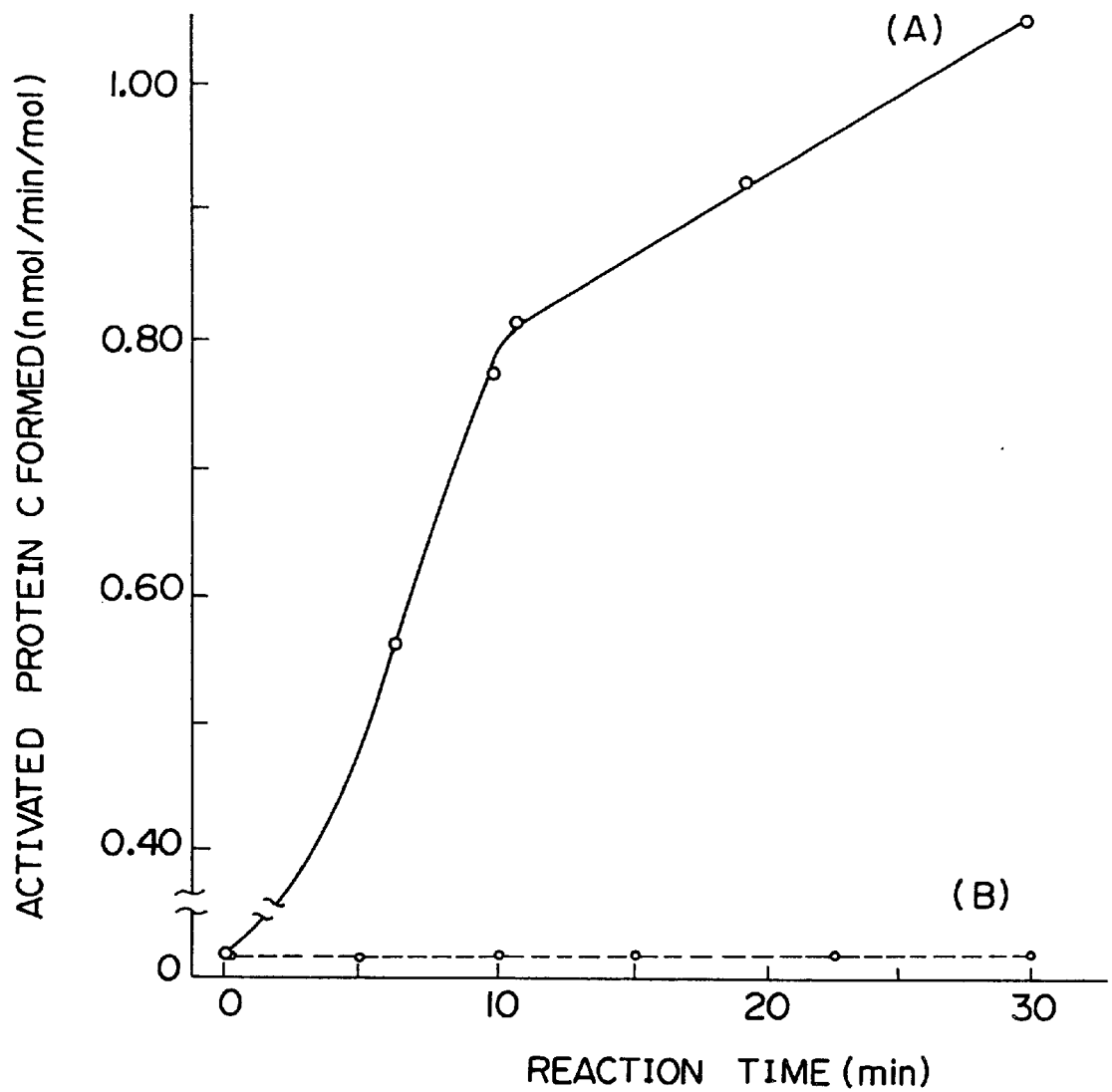
Figure 25:
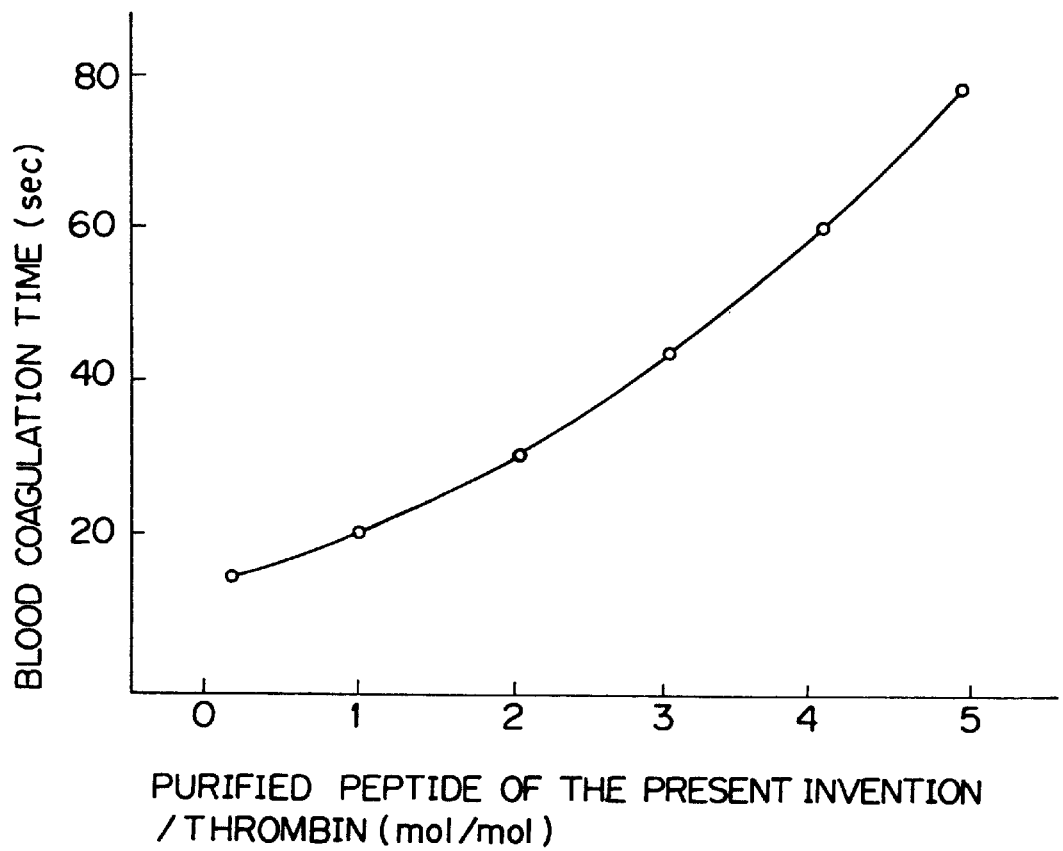
FIGS. 25 to 29 are graphs showing the relationships between the coagulation time of blood to which a purified peptide of the present invention was added and the amount of the added purified peptide of the present invention.
Figure 26:
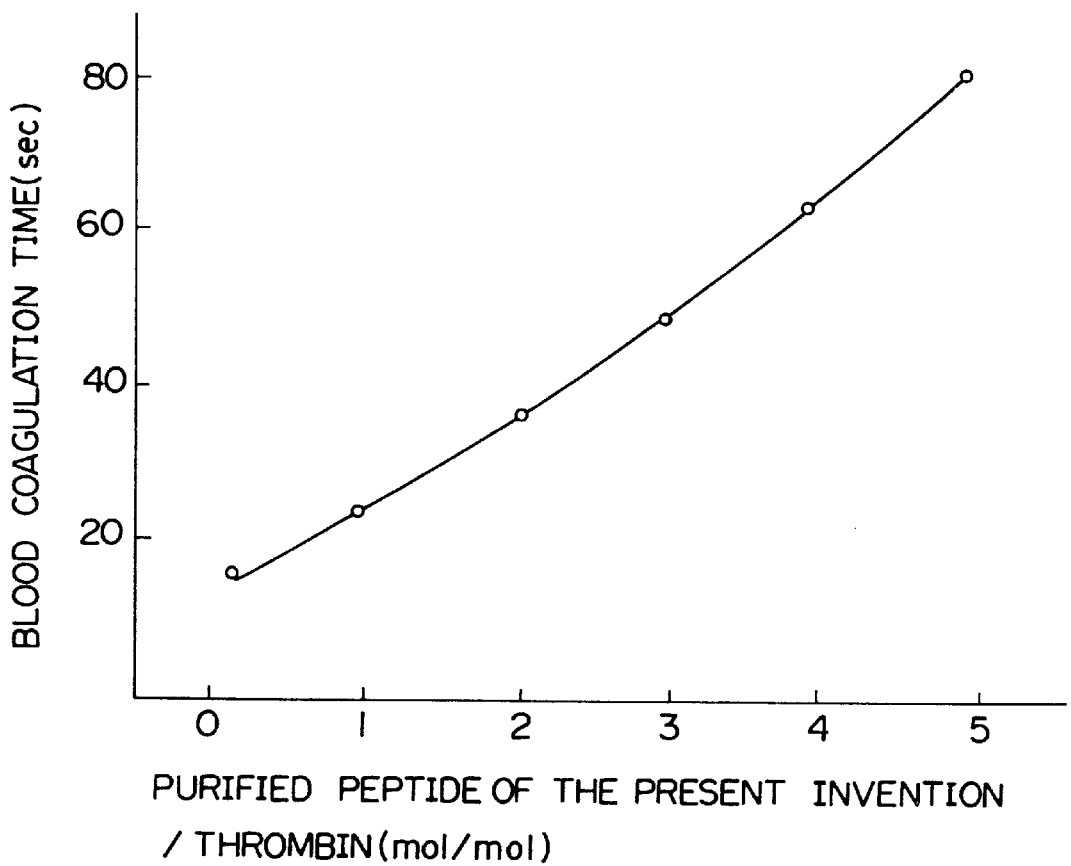
Figure 27:
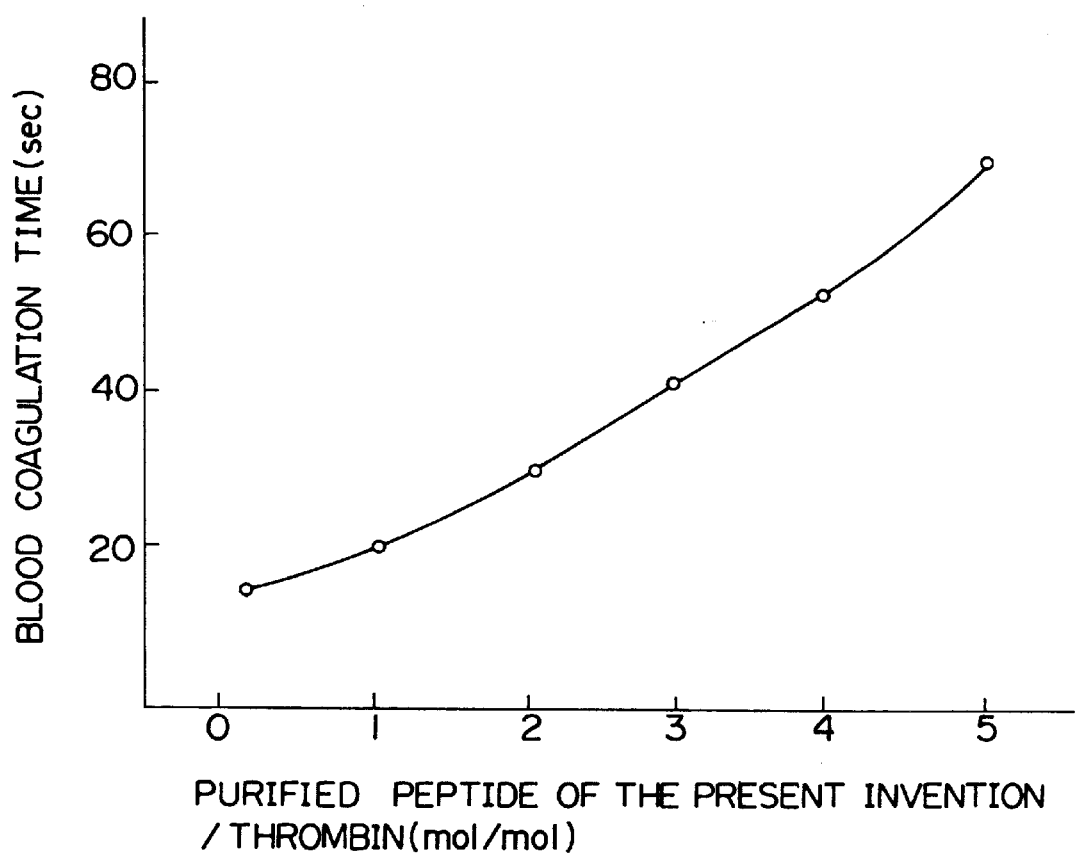
Figure 28:
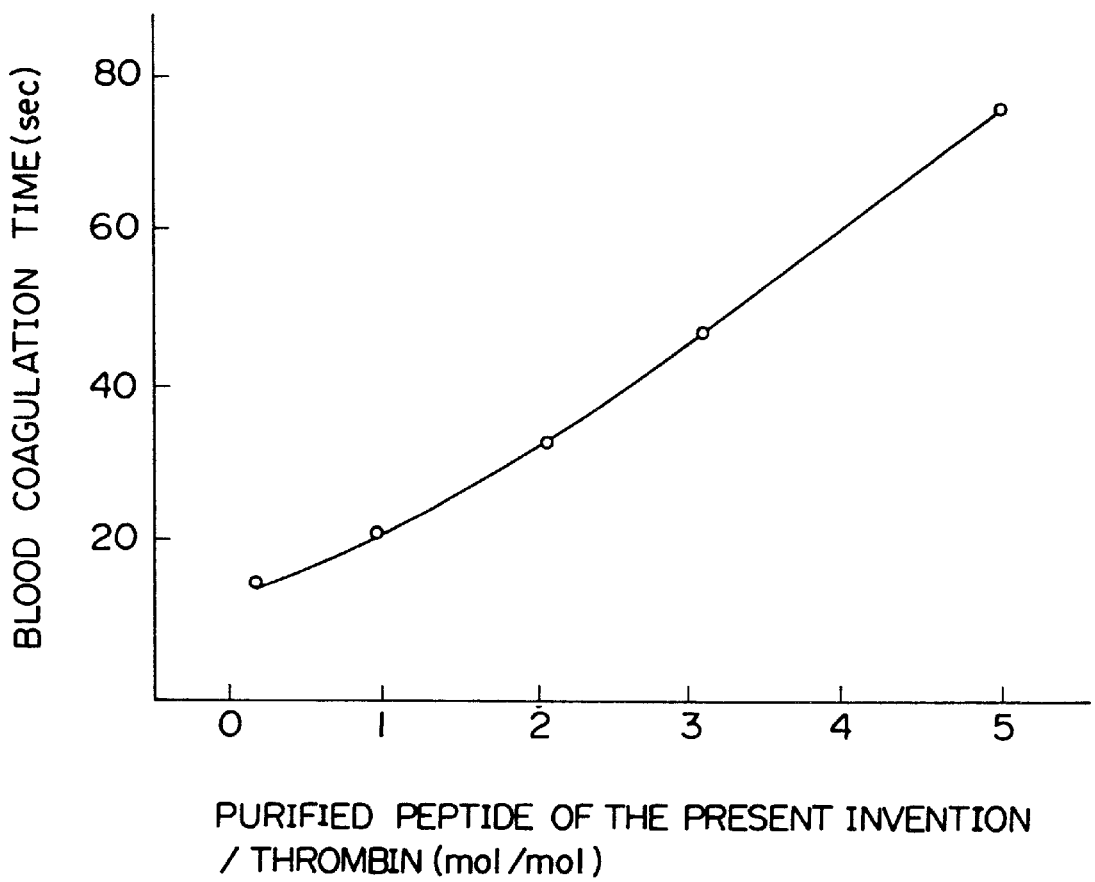
Figure 29:
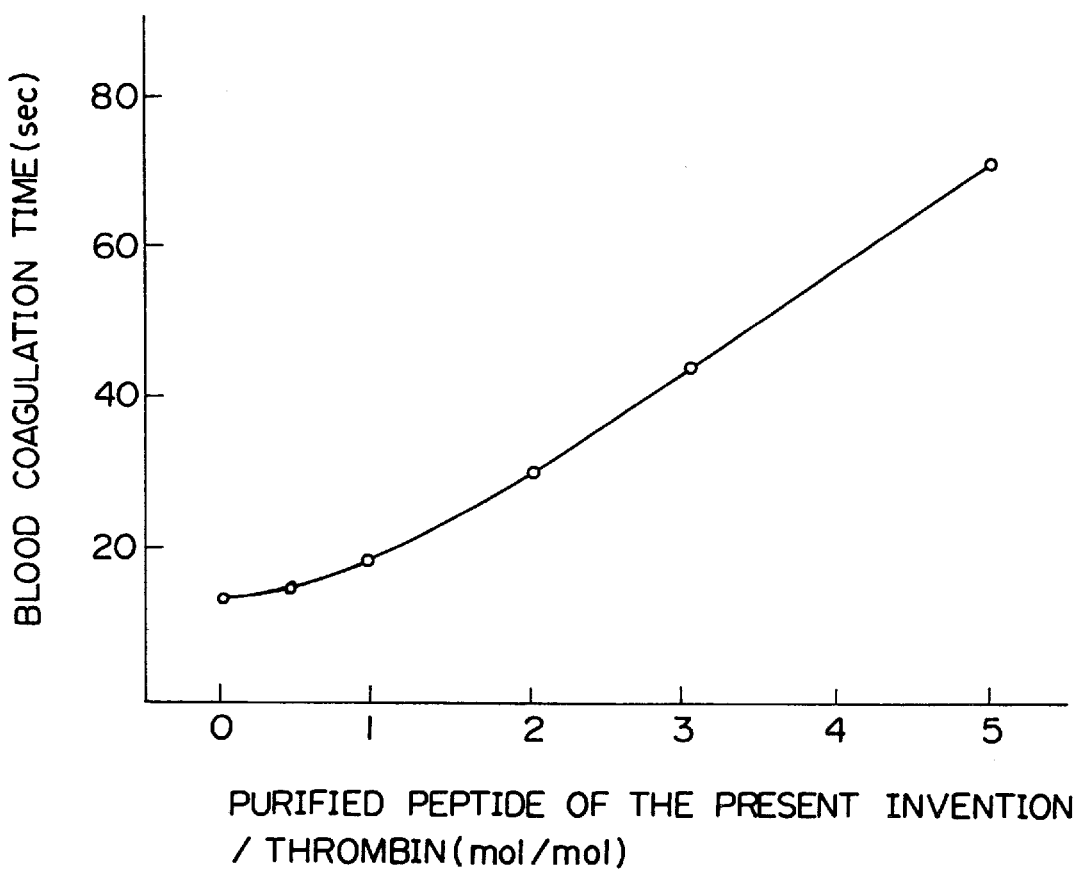

The peptide of the present invention exhibits not only an anti-blood coagulating activity but also a platelet aggregation-inhibiting activity and a thrombolytic activity, and is an extremely useful substance as a medicine, having few harmful side effects, for treating circulatory organ diseases and gestosis. Further, besides the use as a medicine, the present peptide may be used as a drug which is adapted to be fixed to materials for medical articles such as an artificial blood vessel, an artificial organ, catheter and the like in order to prevent the occurrence of thrombosis.

What is claimed is:

1. A peptide having the ability to promote the activation of protein C by thrombin, comprising an amino acid sequence represented by the following formula (I):

Val Glu Pro Val Asp Pro Cys Phe Arg Ala      (I)

Asn Cys Glu Tyr Gln Cys Gln Pro Leu Asn

Gln Thr Ser Tyr Leu Cys Val Cys Ala Glu

Gly Phe Ala Pro Ile Pro His Glu Pro His

Arg Cys Gln Met Phe Cys Asn Gln Thr Ala

Cys Pro Ala Asp Cys Asp Pro Asn Thr Gln

Ala Ser Cys Glu Cys Pro Glu Gly Tyr Ile

Leu Asp Asp Gly Phe Ile Cys Thr Asp Ile

Asp Glu Cys Glu Asn Gly Gly Phe Cys Ser

Gly Val Cys His Asn Leu Pro Gly Thr Phe

Glu Cys Ile Cys Gly Pro Asp Ser Ala Leu

Val Arg His Ile Gly Thr Asp Cys, and not containing an amino acid sequence represented by the formula:

Leu Leu Ile Gly Ile Ser Ile Ala Ser Leu

Cys Leu Val Val Ala Leu Leu Ala Leu Leu

Cys His Leu Arg Lys Lys Gln Gly Ala Ala

Arg Ala Lys Met Glu Tyr Lys Cys Ala Ala

Pro Ser Lys Glu Val Val Leu Gln His Val

Arg Thr Glu Arg Thr Pro Gln Arg Leu.

2. The peptide according to claim 1, which consists of a part or whole of an amino acid sequence represented by the formula:

Ala Pro Ala Glu Pro Gln Pro Gly Gly Ser

Gln Cys Val Glu His Asp Cys Phe Ala Leu

Tyr Pro Gly Pro Ala Thr Phe Leu Asn Ala

Ser Gln Ile Cys Asp Gly Leu Arg Gly His

Leu Met Thr Val Arg Ser Ser Val Ala Ala

Asp Val Ile Ser Leu Leu Leu Asn Gly Asp

Gly Gly Val Gly Arg Arg Arg Leu Trp Ile

Gly Leu Gln Leu Pro Pro Gly Cys Gly Asp

Pro Lys Arg Leu Gly Pro Leu Arg Gly Phe

Gln Trp Val Thr Gly Asp Asn Asn Thr Ser

Tyr Ser Arg Trp Ala Arg Leu Asp Leu Asn

Gly Ala Pro Leu Cys Gly Pro Leu Cys Val

Ala Val Ser Ala Ala Glu Ala Thr Val Pro

Ser Glu Pro Ile Trp Glu Glu Gln Gln Cys

Glu Val Lys Ala Asp Gly Phe Leu Cys Glu

Phe His Phe Pro Ala Thr Cys Arg Pro Leu

Ala Val Glu Pro Gly Ala Ala Ala Ala Ala

Val Ser Ile Thr Tyr Gly Thr Pro Phe Ala

Ala Arg Gly Ala Asp Phe Gln Ala Leu Pro

Val Gly Ser Ser Ala Ala Val Ala Pro Leu

Gly Leu Gln Leu Met Cys Thr Ala Pro Pro

Gly Ala Val Gln Gly His Trp Ala Arg Glu

Ala Pro Gly Ala Trp Asp Cys Ser Val Glu

Asn Gly Gly Cys Glu His Ala Cys Asn Ala

Ile Pro Gly Ala Pro Arg Cys Gln Cys Pro

Ala Gly Ala Ala Leu Gln Ala Asp Gly Arg

Ser Cys Thr Ala Ser Ala Thr Gln Ser Cys

Asn Asp Leu Cys Glu His Phe Cys Val Pro

Asn Pro Asp Gln Pro Gly Ser Tyr Ser Cys

Met Cys Glu Thr Gly Tyr Arg Leu Ala Ala

Asp Gln His Arg Cys Glu Asp Val Asp Asp

Cys Ile Leu Glu Pro Ser Pro Cys Pro Gln

Arg Cys Val Asn Thr Gln Gly Gly Phe Glu

Cys His Cys Tyr Pro Asn Tyr Asp Leu Val

Asp Gly Glu Cys Val Glu Pro Val Asp Pro

Cys Phe Arg Ala Asn Cys Glu Tyr Gln Cys

Gln Pro Leu Asn Gln Thr Ser Tyr Leu Cys

Val Cys Ala Glu Gly Phe Ala Pro Ile Pro

His Glu Pro His Arg Cys Gln Met Phe Cys

```
        Asn Gln Thr Ala Cys Pro Ala Asp Cys Asp

Pro Asn Thr Gln ALa Ser Cys Glu Cys Pro

Glu Gly Tyr Ile Leu Asp Asp Gly Phe Ile

Cys Thr Asp Ile Asp Glu Cys Glu Asn Gly

Gly Phe Cys Ser Gly Val Cys His Asn Leu

Pro Gly Thr Phe Glu Cys Ile Cys Gly Pro

Asp Ser Ala Leu Val Arg His Ile Gly Thr

Asp Cys Asp Ser Gly Lys Val Asp Gly Gly

Asp Ser Gly Ser Gly Glu Pro Pro Pro Ser

Pro Thr Pro Gly Ser Thr Leu Thr Pro Pro

Ala Val Gly Leu Val His Ser Gly,
``` said part comprising an amino acid sequence represented by the following formula (I):

```
Val Glu Pro Val Asp Pro Cys Phe Arg Ala        (I)

Asn Cys Glu Tyr Gln Cys Gln Pro Leu Asn

Gln Thr Ser Tyr Leu Cys Val Cys Ala Glu

Gly Phe Ala Pro Ile Pro His Glu Pro His

Arg Cys Gln Met Phe Cys Asn Gln Thr Ala

Cys Pro Ala Asp Cys Asp Pro Asn Thr Gln

Ala Ser Cys Glu Cys Pro Glu Gly Tyr Ile

Leu Asp Asp Gly Phe Ile Cys Thr Asp Ile

Asp Glu Cys Glu Asn Gly Gly Phe Cys Ser

Gly Val Cys His Asn Leu Pro Gly Thr Phe

Glu Cys Ile Cys Gly Pro Asp Ser Ala Leu

Val Arg His Ile Gly Thr Asp Cys.
```

3. The peptide according to claim 2, which consists of the whole of an amino acid sequence represented by the formula:

```
        Ala Pro Ala Glu Pro Gln Pro Gly Gly Ser

Gln Cys Val Glu His Asp Cys Phe Ala Leu

Tyr Pro Gly Pro Ala Thr Phe Leu Asn Ala

Ser Gln Ile Cys Asp Gly Leu Arg Gly His

Leu Met Thr Val Arg Ser Ser Val Ala Ala

Asp Val Ile Ser Leu Leu Leu Asn Gly Asp

Gly Gly Val Gly Arg Arg Arg Leu Trp Ile

Gly Leu Gln Leu Pro Pro Gly Cys Gly Asp

Pro Lys Arg Leu Gly Pro Leu Arg Gly Phe

Gln Trp Val Thr Gly Asp Asn Asn Thr Ser

Tyr Ser Arg Trp Ala Arg Leu Asp Leu Asn

Gly Ala Pro Leu Cys Gly Pro Leu Cys Val

Ala Val Ser Ala Ala Glu Ala Thr Val Pro

Ser Glu Pro Ile Trp Glu Glu Gln Gln Cys

Glu Val Lys Ala Asp Gly Phe Leu Cys Glu

Phe His Phe Pro Ala Thr Cys Arg Pro Leu

Ala Val Glu Pro Gly Ala Ala Ala Ala Ala

Val Ser Ile Thr Tyr Gly Thr Pro Phe Ala

Ala Arg Gly Ala Asp Phe Gln Ala Leu Pro

Val Gly Ser Ser Ala Ala Val Ala Pro Leu

Gly Leu Gln Leu Met Cys Thr Ala Pro Pro

Gly Ala Val Gln Gly His Trp Ala Arg Glu

Ala Pro Gly Ala Trp Asp Cys Ser Val Glu

Asn Gly Gly Cys Glu His Ala Cys Asn Ala

Ile Pro Gly Ala Pro Arg Cys Gln Cys Pro

Ala Gly Ala Ala Leu Gln Ala Asp Gly Arg

Ser Cys Thr Ala Ser Ala Thr Gln Ser Cys

Asn Asp Leu Cys Glu His Phe Cys Val Pro

Asn Pro Asp Gln Pro Gly Ser Tyr Ser Cys

Met Cys Glu Thr Gly Tyr Arg Leu Ala Ala

Asp Gln His Arg Cys Glu Asp Val Asp Asp

Cys Ile Leu Glu Pro Ser Pro Cys Pro Gln

Arg Cys Val Asn Thr Gln Gly Gly Phe Glu

Cys His Cys Tyr Pro Asn Tyr Asp Leu Val

Asp Gly Glu Cys Val Glu Pro Val Asp Pro

Cys Phe Arg Ala Asn Cys Glu Tyr Gln Cys

Gln Pro Leu Asn Gln Thr Ser Tyr Leu Cys

Val Cys Ala Glu Gly Phe Ala Pro Ile Pro

His Glu Pro His Arg Cys Gln Met Phe Cys

Asn Gln Thr Ala Cys Pro Ala Asp Cys Asp

Pro Asn Thr Gln Ala Ser Cys Glu Cys Pro

Glu Gly Tyr Ile Leu Asp Asp Gly Phe Ile

Cys Thr Asp Ile Asp Glu Cys Glu Asn Gly

Gly Phe Cys Ser Gly Val Cys His Asn Leu

Pro Gly Thr Phe Glu Cys Ile Cys Gly Pro

Asp Ser Ala Leu Val Arg His Ile Gly Thr

Asp Cys Asp Ser Gly Lys Val Asp Gly Gly

Asp Ser Gly Ser Gly Glu Pro Pro Pro Ser

Pro Thr Pro Gly Ser Thr Leu Thr Pro Pro

Ala Val Gly Leu Val His Ser Gly.
```

4. An isolated deoxyribonucleic acid comprising a base sequence represented by the following formula (II):

```
GTGGAGCC CGTGGACCCG TGCTTCAGAG CCAACTGCGA      (II)

GTACCAGTGC CAGCCCCTGA ACCAAACTAG CTACCTCTGC

GTCTGCGCCG AGGGCTTCGC GCCCATTCCC CACGAGCCGC

ACAGGTGCCA GATGTTTTGC AACCAGACTG CCTGTCCAGC

CGACTGCGAC CCCAACACCC AGGCTAGCTG TGAGTGCCCT

GAAGGCTACA TCCTGGACGA CGGTTTCATC TGCACGGACA

TCGACGAGTG CGAAAACGGC GGCTTCTGCT CCGGGGTGTG

CCACAACCTC CCCGGTACCT TCGAGTGCAT CTGCGGGCCC

GACTCGGCCC TTGTCCGCCA CATTGGCACC GACTGT,
``` and not containing a base sequence represented by the formula:

```
            TTGCTC ATAGGCATCT CCATCGCGAG

CCTGTGCCTG GTGGTGGCGC TTTTGGCGCT CCTCTGCCAC

CTGCGCAAGA AGCAGGGCGC CGCCAGGGCC AAGATGGAGT

ACAAGTGCGC GGCCCCTTCC AAGGAGGTAG TGCTGCAGCA

CGTGCGGACC GAGCGGACGC CGCAGAGACT C.
```

5. The deoxyribonucleic acid according to claim 4, which consists of a part or whole of a base sequence represented by the formula:

```
GCACCCGCAG AGCCGCAGCC GGGTGGCAGC CAGTGCGTCG

AGCACGACTG CTTCGCGCTC TACCCGGGCC CCGCGACCTT

CCTCAATGCC AGTCAGATCT GCGACGGACT GCGGGGCCAC

CTAATGACAG TGCGCTCCTC GGTGGCTGCC GATGTCATTT

CCTTGCTACT GAACGGCGAC GGCGGCGTTG GCCGCCGGCG

CCTCTGGATC GGCCTGCAGC TGCCACCCGG CTGCGGCGAC

CCCAAGCGCC TCGGGCCCCT GCGCGGCTTC CAGTGGGTTA

CGGGAGACAA CAACACCAGC TATAGCAGGT GGGCACGGCT

CGACCTCAAT GGGGCTCCCC TCTGCGGCCC GTTGTGCGTC

GCTGTCTCCG CTGCTGAGGC CACTGTGCCC AGCGAGCCGA

TCTGGGAGGA GCAGCAGTGC GAAGTGAAGG CCGATGGCTT

CCTCTGCGAG TTCCACTTCC CAGCCACCTG CAGGCCACTG

GCTGTGGAGC CCGGCGCCGC GGCTGCCGCC GTCTCGATCA

CCTACGGCAC CCCGTTCGCG GCCCGCGGAG CGGACTTCCA

GGCGCTGCCG GTGGGCAGCT CCGCCGCGGT GGCTCCCCTC

GGCTTACAGC TAATGTGCAC CGCGCCGCCC GGAGCGGTCC

AGGGGCACTG GGCCAGGGAG GCGCCGGGCG CTTGGGACTG

CAGCGTGGAG AACGGCGGCT GCGAGCACGC GTGCAATGCG

ATCCCTGGGG CTCCCCGCTG CCAGTGCCCA GCCGGCGCCG

CCCTGCAGGC AGACGGGCGC TCCTGCACCG CATCCGCGAC

GCAGTCCTGC AACGACCTCT GCGAGCACTT CTGCGTTCCC

AACCCCGACC AGCCGGGCTC CTACTCGTGC ATGTGCGAGA

CCGGCTACCG GCTGGCGGCC GACCAACACC GGTGCGAGGA

CGTGGATGAC TGCATACTGG AGCCCAGTCC GTGTCCGCAG

CGCTGTGTCA ACACACAGGG TGGCTTCGAG TGCCACTGCT

ACCCTAACTA CGACCTGGTG GACGGCGAGT GTGTGGAGCC

CGTGGACCCG TGCTTCAGAG CCAACTGCGA GTACCAGTGC

CAGCCCCTGA ACCAAACTAG CTACCTCTGC GTCTGCGCCG

AGGGCTTCGC GCCCATTCCC CACGAGCCGC ACAGGTGCCA

GATGTTTTGC AACCAGACTG CCTGTCCAGC CGACTGCGAC

CCCAACACCC AGGCTAGCTG TGAGTGCCCT GAAGGCTACA

TCCTGGACGA CGGTTTCATC TGCACGGACA TCGACGAGTG

CGAAAACGGC GGCTTCTGCT CCGGGGTGTG CCACAACCTC

CCCGGTACCT TCGAGTGCAT CTGCGGGCCC GACTCGGCCC

TTGTCCGCCA CATTGGCACC GACTGTGACT CCGGCAAGGT

GGACGGTGGC GACAGCGGCT CTGGCGAGCC CCCGCCCAGC

CCGACGCCCG GCTCCACCTT GACTCCTCCG GCCGTGGGGC

TCGTGCATTC GGGC,
``` said part comprising a base sequence represented by the following formula (II):

```
GTGGAGCC CGTGGACCCG TGCTTCAGAG CCAACTGCGA      (II)

GTACCAGTGC CAGCCCCTGA ACCAAACTAG CTACCTCTGC

GTCTGCGCCG AGGGCTTCGC GCCCATTCCC CACGAGCCGC

ACAGGTGCCA GATGTTTTGC AACCAGACTG CCTGTCCAGC

CGACTGCGAC CCCAACACCC AGGCTAGCTG TGAGTGCCCT

GAAGGCTACA TCCTGGACGA CGGTTTCATC TGCACGGACA

TCGACGAGTG CGAAAACGGC GGCTTCTGCT CCGGGGTGTG

CCACAACCTC CCCGGTACCT TCGAGTGCAT CTGCGGGCCC

GACTCGGCCC TTGTCCGCCA CATTGGCACC GACTGT;
``` or a variant of said deoxyribonucleic acid wherein said part or whole of said base sequence is modified in accordance with the degeneracy of the Genetic Code.

6. The deoxyribonucleic acid according to claim 5, which consists of the whole of a base sequence represented by the formula:

```
GCACCCGCAG AGCCGCAGCC GGGTGGCAGC CAGTGCGTCG

AGCACGACTG CTTCGCGCTC TACCCGGGCC CCGCGACCTT

CCTCAATGCC AGTCAGATCT GCGACGGACT GCGGGGCCAC

CTAATGACAG TGCGCTCCTC GGTGGCTGCC GATGTCATTT

CCTTGCTACT GAACGGCGAC GGCGGCGTTG GCCGCCGGCG

CCTCTGGATC GGCCTGCAGC TGCCACCCGG CTGCGGCGAC

CCCAAGCGCC TCGGGCCCCT GCGCGGCTTC CAGTGGGTTA

CGGGAGACAA CAACACCAGC TATAGCAGGT GGGCACGGCT

CGACCTCAAT GGGGCTCCCC TCTGCGGCCC GTTGTGCGTC
```

```
                         -continued
GCTGTCTCCG CTGCTGAGGC CACTGTGCCC AGCGAGCCGA

TCTGGGAGGA GCAGCAGTGC GAAGTGAAGG CCGATGGCTT

CCTCTGCGAG TTCCACTTCC CAGCCACCTG CAGGCCACTG

GCTGTGGAGC CCGGCGCCGC GGCTGCCGCC GTCTCGATCA

CCTACGGCAC CCCGTTCGCG GCCCGCGGAG CGGACTTCCA

GGCGCTGCCG GTGGGCAGCT CCGCCGCGGT GGCTCCCCTC

GGCTTACAGC TAATGTGCAC CGCGCCGCCC GGAGCGGTCC

AGGGGCACTG GGCCAGGGAG GCGCCGGGCG CTTGGGACTG

CAGCGTGGAG AACGGCGGCT GCGAGCACGC GTGCAATGCG

ATCCCTGGGG CTCCCCGCTG CCAGTGCCCA GCCGGCGCCG

CCCTGCAGGC AGACGGGCGC TCCTGCACCG CATCCGCGAC

GCAGTCCTGC AACGACCTCT GCGAGCACTT CTGCGTTCCC

AACCCCGACC AGCCGGGCTC CTACTCGTGC ATGTGCGAGA

CCGGCTACCG GCTGGCGGCC GACCAACACC GGTGCGAGGA

CGTGGATGAC TGCATACTGG AGCCCAGTCC GTGTCCGCAG

CGCTGTGTCA ACACACAGGG TGGCTTCGAG TGCCACTGCT

ACCCTAACTA CGACCTGGTG GACGGCGAGT GTGTGGAGCC

CGTGGACCCG TGCTTCAGAG CCAACTGCGA GTACCAGTGC

CAGCCCCTGA ACCAAACTAG CTACCTCTGC GTCTGCGCCG

AGGGCTTCGC GCCCATTCCC CACGAGCCGC ACAGGTGCCA

GATGTTTTGC AACCAGACTG CCTGTCCAGC CGACTGCGAC

CCCAACACCC AGGCTAGCTG TGAGTGCCCT GAAGGCTACA

TCCTGGACGA CGGTTTCATC TGCACGGACA TCGACGAGTG

CGAAAACGGC GGCTTCTGCT CCGGGGTGTG CCACAACCTC

CCCGGTACCT TCGAGTGCAT CTGCGGGCCC GACTCGGCCC

TTGTCCGCCA CATTGGCACC GACTGTGACT CCGGCAAGGT

GGACGGTGGC GACAGCGGCT CTGGCGAGCC CCCGCCCAGC

CCGACGCCCG GCTCCACCTT GACTCCTCCG GCCGTGGGGC

TCGTGCATTC GGGC.
```

7. A complementary deoxyribonucleic acid to the deoxyribonucleic acid according to any one of claims 4 to 6.

8. A replicable recombinant DNA which comprises a replicable expression vector and, operably inserted therein, a deoxyribonucleic acid according to claim 7.

9. A microorganism, or cultured or isolated host cell, transformed with a replicable recombinant DNA according to claim 8.

10. A replicable recombinant DNA which comprises a replicable expression vector and, operably inserted therein, a deoxyribonucleic acid according to any one of claims 4–6.

11. A microorganism, or cultured or isolated host cell, transformed with a replicable recombinant DNA according to claim 10.

12. A process for producing a peptide having the ability to promote the activation of protein C by thrombin, said peptide comprising an amino acid sequence represented by the following formula (I):

Val Glu Pro Val Asp Pro Cys Phe Arg Ala (I)

Asn Cys Glu Tyr Gln Cys Gln Pro Leu Asn

Gln Thr Ser Tyr Leu Cys Val Cys Ala Glu

Gly Phe Ala Pro Ile Pro His Glu Pro His

Arg Cys Gln Met Phe Cys Asn Gln Thr Ala

Cys Pro Ala Asp Cys Asp Pro Asn Thr Gln

Ala Ser Cys Glu Cys Pro Glu Gly Tyr Ile

Leu Asp Asp Gly Phe Ile Cys Thr Asp Ile

Asp Glu Cys Glu Asn Gly Gly Phe Cys Ser

Gly Val Cys His Asn Leu Pro Gly Thr Phe

Glu Cys Ile Cys Gly Pro Asp Ser Ala Leu

Val Arg His Ile Gly Thr Asp Cys, and not containing an amino acid sequence represented by the formula:

Leu Leu Ile Gly Ile Ser Ile Ala Ser Leu

Cys Leu Val Val Ala Leu Leu Ala Leu Leu

Cys His Leu Arg Lys Lys Gln Gly Ala Ala

Arg Ala Lys Met Glu Tyr Lys Cys Ala Ala

Pro Ser Lys Glu Val Val Leu Gln His Val

Arg Thr Glu Arg Thr Pro Gln Arg Leu, which comprises:

(a) ligating a deoxyribonucleic acid consisting of a base sequence coding for said peptide to a replicable expression vector to obtain a replicable recombinant DNA comprising said replicable expression vector and, operably inserted therein, said deoxyribonucleic acid;

(b) transforming cells of a microorganism, or cultured or isolated host cells, with said replicable recombinant DNA to form transformants;

(c) selecting said transformants from parent cells of the microorganism or the cultured or isolated host cells;

(d) culturing said transformants, causing said transformants to express said deoxyribonucleic acid and produce a peptide; and (e) isolating said peptide from the culture of said transformants.

13. The process according to claim 12, wherein said deoxyribonucleic acid consists of a base sequence coding for a part or whole of an amino acid sequence represented by the formula:

Ala Pro Ala Glu Pro Gln Pro Gly Gly Ser

Gln Cys Val Glu His Asp Cys Phe Ala Leu

Tyr Pro Gly Pro Ala Thr Phe Leu Asn Ala

Ser Gln Ile Cys Asp Gly Leu Arg Gly His

Leu Met Thr Val Arg Ser Ser Val Ala Ala

Asp Val Ile Ser Leu Leu Leu Asn Gly Asp

Gly Gly Val Gly Arg Arg Arg Leu Trp Ile

```
Gly Leu Gln Leu Pro Pro Gly Cys Gly Asp
Pro Lys Arg Leu Gly Pro Leu Arg Gly Phe
Gln Trp Val Thr Gly Asp Asn Asn Thr Ser
Tyr Ser Arg Trp Ala Arg Leu Asp Leu Asn
Gly Ala Pro Leu Cys Gly Pro Leu Cys Val
Ala Val Ser Ala Ala Glu Ala Thr Val Pro
Ser Glu Pro Ile Trp Glu Glu Gln Gln Cys
Glu Val Lys Ala Asp Gly Phe Leu Cys Glu
Phe His Phe Pro Ala Thr Cys Arg Pro Leu
Ala Val Glu Pro Gly Ala Ala Ala Ala Ala
Val Ser Ile Thr Tyr Gly Thr Pro Phe Ala
Ala Arg Gly Ala Asp Phe Gln Ala Leu Pro
Val Gly Ser Ser Ala Ala Val Ala Pro Leu
Gly Leu Gln Leu Met Cys Thr Ala Pro Pro
Gly Ala Val Gln Gly His Trp Ala Arg Glu
Ala Pro Gly Ala Trp Asp Cys Ser Val Glu
Asn Gly Gly Cys Glu His Ala Cys Asn Ala
Ile Pro Gly Ala Pro Arg Cys Gln Cys Pro
Ala Gly Ala Ala Leu Gln Ala Asp Gly Arg
Ser Cys Thr Ala Ser Ala Thr Gln Ser Cys
Asn Asp Leu Vys Glu His Phe Cys Val Pro
Asn Pro Asp Gln Pro Gly Ser Tyr Ser Cys
Met Cys Glu Thr Gly Tyr Arg Leu Ala Ala
Asp Gln His Arg Cys Glu Asp Val Asp Asp
Cys Ile Leu Glu Pro Ser Pro Cys Pro G

-continued

```
Val Gly Ser Ser Ala Ala Val Ala Pro Leu

Gly Leu Gln Leu Met Cys Thr Ala Pro Pro

Gly Ala Val Gln Gly His Trp Ala Arg Glu

Ala Pro Gly Ala Trp Asp Cys Ser Val Glu

Asn Gly Gly Cys Glu His Ala Cys Asn Ala

Ile Pro Gly Ala Pro Arg Cys Gln Cys Pro

Ala Gly Ala Ala Leu Gln Ala Asp Gly Arg

Ser Cys Thr Ala Ser Ala Thr Gln Ser Cys

Asn Asp Leu Cys Glu His Phe Cys Val Pro

Asn Pro Asp Gln Pro Gly Ser Tyr Ser Cys

Met Cys Glu Thr Gly Tyr Arg Leu Ala Ala

Asp Gln His Arg Cys Glu Asp Val Asp Asp

Cys Ile Leu Glu Pro Ser Pro Cys Pro Gln

Arg Cys Val Asn Thr Gln Gly Gly Phe Glu

Cys His Cys Tyr Pro Asn Tyr Asp Leu Val

Asp Gly Glu Cys Val Glu Pro Val Asp Pro

Cys Phe Arg Ala Asn Cys Glu Tyr Gln Cys

Gln Pro Leu Asn Gln Thr Ser Tyr Leu Cys

Val Cys Ala Glu Gly Phe Ala Pro Ile Pro

His Glu Pro His Arg Cys Gln Met Phe Cys

Asn Gln Thr Ala Cys Pro Ala Asp Cys Asp

Pro Asn Thr Gln Ala Ser Cys Glu Cys Pro

Glu Gly Tyr Ile Leu Asp Asp Gly Phe Ile

Cys Thr Asp Ile Asp Glu Cys Glu Asn Gly

Gly Phe Cys Ser Gly Val Cys His Asn Leu

Pro Gly Thr Phe Glu Cys Ile Cys Gly Pro

Asp Ser Ala Leu Val Arg His Ile Gly Thr

Asp Cys Asp Ser Gly Lys Val Asp Gly Gly

Asp Ser Gly Ser Gly Glu Pro Pro Pro Ser

Pro Thr Pro Gly Ser Thr Leu Thr Pro Pro

Ala Val Gly Leu Val His Ser Gly.
```

15. A pharmaceutical composition comprising:

an effective amount for exhibiting anticoagulant, platelet aggregation-inhibiting or thrombolytic activities of a peptide having the ability to promote the activation of protein C by thrombin, said peptide comprising an amino acid sequence represented by the following formula (I):

```
Val Glu Pro Val Asp Pro Cys Phe Arg Ala    (I)

Asn Cys Glu Tyr Gln Cys Gln Pro Leu Asn

Gln Thr Ser Tyr Leu Cys Val Cys Ala Glu

Gly Phe Ala Pro Ile Pro His Glu Pro His

Arg Cys Gln Met Phe Cys Asn Gln Thr Ala

Cys Pro Ala Asp Cys Asp Pro Asn Thr Gln

Ala Ser Cys Glu Cys Pro Glu Gly Tyr Ile

Leu Asp Asp Gly Phe Ile Cys Thr Asp Ile

Asp Glu Cys Glu Asn Gly Gly Phe Cys Ser

Gly Val Cys His Asn Leu Pro Gly Thr Phe

Glu Cys Ile Cys Gly Pro Asp Ser Ala Leu

Val Arg His Ile Gly Thr Asp Cys,
``` and not containing an amino acid sequence represented by the formula:

```
Leu Leu Ile Gly Ile Ser Ile Ala Ser Leu

Cys Leu Val Val Ala Leu Leu Ala Leu Leu

Cys His Leu Arg Lys Lys Gln Gly Ala Ala

Arg Ala Lys Met Glu Tyr Lys Cys Ala Ala

Pro Ser Lys Glu Val Val Leu Gln His Val

Arg Thr Glu Arg Thr Pro Gln Arg Leu;
``` and at least one pharmaceutically acceptable carrier, diluent or excipient.

16. The pharmaceutical composition according to claim 15, wherein said peptide consists of a part or whole of an amino acid sequence represented by the formula:

```
Ala Pro Ala Glu Pro Gln Pro Gly Gly Ser

Gln Cys Val Glu His Asp Cys Phe Ala Leu

Tyr Pro Gly Pro Ala Thr Phe Leu Asn Ala

Ser Gln Ile Cys Asp Gly Leu Arg Gly His

Leu Met Thr Val Arg Ser Ser Val Ala Ala

Asp Val Ile Ser Leu Leu Leu Asn Gly Asp

Gly Gly Val Gly Arg Arg Arg Leu Trp Ile

Gly Leu Gln Leu Pro Pro Gly Cys Gly Asp

Pro Lys Arg Leu Gly Pro Leu Arg Gly Phe

Gln Trp Val Thr Gly Asp Asn Asn Thr Ser

Tyr Ser Arg Trp Ala Arg Leu Asp Leu Asn

Gly Ala Pro Leu Cys Gly Pro Leu Cys Val

Ala Val Ser Ala Ala Glu Ala Thr Val Pro

Ser Glu Pro Ile Trp Glu Glu Gln Gln Cys

Glu Val Lys Ala Asp Gly Phe Leu Cys Glu

Phe His Phe Pro Ala Thr Cys Arg Pro Leu

Ala Val Glu Pro Gly Ala Ala Ala Ala Ala

Val Ser Ile Thr Tyr Gly Thr Pro Phe Ala

Ala Arg Gly Ala Asp Phe Gln Ala Leu Pro

Val Gly Ser Ser Ala Ala Val Ala Pro Leu

Gly Leu Gln Leu Met Cys Thr Ala Pro Pro

Gly Ala Val Gln Gly His Trp Ala Arg Glu
```

Ala Pro Gly Ala Trp Asp Cys Ser Val Glu

Asn Gly Gly Cys Glu His Ala Cys Asn Ala

Ile Pro Gly Ala Pro Arg Cys Gln Cys Pro

Ala Gly Ala Ala Leu Gln Ala Asp Gly Arg

Ser Cys Thr Ala Ser Ala Thr Gln Ser Cys

Asn Asp Leu Vys Glu His Phe Cys Val Pro

Asn Pro Asp Gln Pro Gly Ser Tyr Ser Cys

Met Cys Glu Thr Gly Tyr Arg Leu Ala Ala

Asp Gln His Arg Cys Glu Asp Val Asp Asp

Cys Ile Leu Glu Pro Ser Pro Cys Pro Gln

Arg Cys Val Asn Thr Gln Gly Gly Phe Glu

Cys His Cys Tyr Pro Asn Tyr Asp Leu Val

Asp Gly Glu Cys Val Glu Pro Val Asp Pro

Cys Phe Arg Ala Asn Cys Glu Tyr Gln Cys

Gln Pro Leu Asn Gln Thr Ser Tyr Leu Cys

Val Cys Ala Glu Gly Phe Ala Pro Ile Pro

His Glu Pro His Arg Cys Gln Met Phe Cys

Asn Gln Thr Ala Cys Pro Ala Asp Cys Asp

Pro Asn Thr Gln ALa Ser Cys Glu Cys Pro

Glu Gly Tyr Ile Leu Asp Asp Gly Phe Ile

Cys Thr Asp Ile Asp Glu Cys Glu Asn Gly

Gly Phe Cys Ser Gly Val Cys His Asn Leu

Pro Gly Thr Phe Glu Cys Ile Cys Gly Pro

Asp Ser Ala Leu Val Arg His Ile Gly Thr

Asp Vys Asp Ser Gly Lys Val Asp Gly Gly

Asp Ser Gly Ser Gly Glu Pro Pro Pro Ser

Pro Thr Pro Gly Ser Thr Leu Thr Pro Pro

Ala Val Gly Leu Val His Ser Gly, said part comprising an amino acid sequence represented by the following formula (I):

Val Glu Pro Val Asp Pro Cys Phe Arg Ala (I)

Asn Cys Glu Tyr Gln Cys Gln Pro Leu Asn

Gln Thr Ser Tyr Leu Cys Val Cys Ala Glu

Gly Phe Ala Pro Ile Pro His Glu Pro His

Arg Cys Gln Met Phe Cys Asn Gln Thr Ala

Cys Pro Ala Asp Cys Asp Pro Asn Thr Gln

Ala Ser Cys Glu Cys Pro Glu Gly Tyr Ile

Leu Asp Asp Gly Phe Ile Cys Thr Asp Ile

Asp Glu Cys Glu Asn Gly Gly Phe Cys Ser

Gly Val Cys His Asn Leu Pro Gly Thr Phe

Glu Cys Ile Cys Gly Pro Asp Ser Ala Leu

Val Arg His Ile Gly Thr Asp Cys.

17. The pharmaceutical composition according to claim 16, wherein said peptide consists of the whole of an amino acid sequence represented by the formula:

Ala Pro Ala Glu Pro Gln Pro Gly Gly Ser

Gln Cys Val Glu His Asp Cys Phe Ala Leu

Tyr Pro Gly Pro Ala Thr Phe Leu Asn Ala

Ser Gln Ile Cys Asp Gly Leu Arg Gly His

Leu Met Thr Val Arg Ser Ser Val Ala Ala

Asp Val Ile Ser Leu Leu Leu Asn Gly Asp

Gly Gly Val Gly Arg Arg Arg Leu Trp Ile

Gly Leu Gln Leu Pro Pro Gly Cys Gly Asp

Pro Lys Arg Leu Gly Pro Leu Arg Gly Phe

Gln Trp Val Thr Gly Asp Asn Asn Thr Ser

Tyr Ser Arg Trp Ala Arg Leu Asp Leu Asn

Gly Ala Pro Leu Cys Gly Pro Leu Cys Val

Ala Val Ser Ala Ala Glu Ala Thr Val Pro

Ser Glu Pro Ile Trp Glu Gln Gln Cys

Glu Val Lys Ala Asp Gly Phe Leu Cys Glu

Phe His Phe Pro Ala Thr Cys Arg Pro Leu

Ala Val Glu Pro Gly Ala Ala Ala Ala Ala

Val Ser Ile Thr Tyr Gly Thr Pro Phe Ala

Ala Arg Gly Ala Asp Phe Gln Ala Leu Pro

Val Gly Ser Ser Ala Ala Val Ala Pro Leu

Gly Leu Gln Leu Met Cys Thr Ala Pro Pro

Gly Ala Val Gln Gly His Trp Ala Arg Glu

Ala Pro Gly Ala Trp Asp Cys Ser Val Glu

Asn Gly Gly Cys Glu His Ala Cys Asn Ala

Ile Pro Gly Ala Pro Arg Cys Gln Cys Pro

Ala Gly Ala Ala Leu Gln Ala Asp Gly Arg

Ser Cys Thr Ala Ser Ala Thr Gln Ser Cys

Asn Asp Leu Cys Glu His Phe Cys Val Pro

Asn Pro Asp Gln Pro GLy Ser Tyr Ser Cys

Met Cys Glu Thr Gly Tyr Arg Leu Ala Ala

Asp Gln His Arg Cys Glu Asp Val Asp Asp

Cys Ile Leu Glu Pro Ser Pro Cys Pro Gln

Arg Cys Val Asn Thr Gln Gly Gly Phe Glu

Cys His Cys Tyr Pro Asn Tyr Asp Leu Val

Asp Gly Glu Cys Val Glu Pro Val Asp Pro

Cys Phe Arg Ala Asn Cys Glu Tyr Gln Cys

Glu Cys Ile Cys Gly Pro Asp Ser Ala Leu

Val Arg His Ile Gly Thr Asp Cys.

-continued

Gln Pro Leu Asn Gln Thr Ser Tyr Leu Cys

Val Cys Ala Glu Gly Phe Ala Pro Ile Pro

His Glu Pro His Arg Cys Gln Met Phe Cys

Asn Gln Thr Ala Cys Pro Ala Asp Cys Asp

Pro Asn Thr Gln Ala Ser Cys Glu Cys Pro

Glu Gly Tyr Ile Leu Asp Asp Gly Phe Ile

Cys Thr Asp Ile Asp Glu Cys Glu Asn Gly

Gly Phe Cys Ser Gly Val Cys His Asn Leu

-continued

Pro Gly Thr Phe Glu Cys Ile Cys Gly Pro

Asp Ser Ala Leu Val Arg His Ile Gly Thr

Asp Cys Asp Ser Gly Lys Val Asp Gly Gly

Asp Ser Gly Ser Gly Glu Pro Pro Pro Ser

Pro Thr Pro Gly Ser Thr Leu Thr Pro Pro

Ala Val Gly Leu Val His Ser Gly.

\* \* \* \* \*